(12) United States Patent
Neurohr et al.

(10) Patent No.: US 9,901,360 B2
(45) Date of Patent: Feb. 27, 2018

(54) ULTRASONIC SURGICAL INSTRUMENT WITH RETRACTABLE INTEGRAL CLAMP ARM

(71) Applicant: Ethicon Endo-Surgery, Inc., Cincinnati, OH (US)

(72) Inventors: Mark A. Neurohr, Newport, KY (US); Matthew C. Miller, Cincinnati, OH (US); Kevin L. Houser, Springboro, OH (US); Joyce A. Duell, Loveland, OH (US); David A. Witt, Maineville, OH (US); Galen C. Robertson, Apex, NC (US)

(73) Assignee: Ethicon LLC, Guaynabo, PR (US)

( * ) Notice: Subject to any disclaimer, the term of this patent is extended or adjusted under 35 U.S.C. 154(b) by 497 days.

(21) Appl. No.: 14/488,454

(22) Filed: Sep. 17, 2014

(65) Prior Publication Data

US 2016/0074061 A1 Mar. 17, 2016

(51) Int. Cl.
*A61B 17/32* (2006.01)
*A61B 18/14* (2006.01)

(52) U.S. Cl.
CPC ...... *A61B 17/320092* (2013.01); *A61B 18/14* (2013.01); *A61B 2017/320078* (2017.08); *A61B 2018/1412* (2013.01)

(58) Field of Classification Search
CPC .... A61B 2017/2926; A61B 2017/2927; A61B 2017/2947; A61B 17/295;
(Continued)

(56) References Cited

U.S. PATENT DOCUMENTS 3,053,124 A * 9/1962 Balamuth ............ B23K 20/106
228/110.1
4,655,216 A * 4/1987 Tischer .............. A61B 18/1445
600/564

(Continued)

FOREIGN PATENT DOCUMENTS

WO WO 2005/084250 A2 9/2005

OTHER PUBLICATIONS

International Search Report and Written Opinion dated Jan. 5, 2016 for Application No. PCT/US2015/050188, 13 pgs.

*Primary Examiner* — David C Eastwood
(74) *Attorney, Agent, or Firm* — Frost Brown Todd LLC

(57) ABSTRACT

An ultrasonic instrument comprises a handle assembly configured to receive an ultrasonic transducer, a shaft assembly having an acoustic waveguide and an ultrasonic blade, and a retractable clamp arm. The ultrasonic blade is in acoustic communication with the acoustic waveguide such that the ultrasonic transducer is operable to drive the ultrasonic blade to vibrate ultrasonically via the acoustic waveguide. The clamp arm is configured to selectively translate between an inoperative position and an operative position. The clamp arm is positioned generally proximal to the ultrasonic blade when the clamp arm is in the inoperative position. The clamp arm is positioned lateral to the ultrasonic blade when the clamp arm is in the operative position. When in the operative position, the clamp arm is operable to move toward and away from the ultrasonic blade so as to capture and compress tissue between the clamp arm and the ultrasonic blade.

17 Claims, 53 Drawing Sheets

(58) Field of Classification Search
CPC ...... A61B 2017/291; A61B 2017/2901; A61B 2017/2902; A61B 17/28; A61B 17/29; A61B 17/320068; A61B 18/1442; A61B 18/1445; A61B 2018/145; A61B 2018/1452; A61B 2017/1455

See application file for complete search history.

(56) References Cited

U.S. PATENT DOCUMENTS

| | | | |
|---|---|---|---|
| 5,322,055 | A | 6/1994 | Davison et al. |
| 5,324,299 | A | 6/1994 | Davison et al. |
| 5,873,873 | A | 2/1999 | Smith et al. |
| 5,980,510 | A | 11/1999 | Tsonton et al. |
| 6,110,171 | A * | 8/2000 | Rydell ............... A61B 18/1442 606/48 |
| 6,129,735 | A * | 10/2000 | Okada ............... A61B 17/32006 606/169 |
| 6,139,561 | A * | 10/2000 | Shibata ............ A61B 17/32006 606/169 |
| 6,283,981 | B1 | 9/2001 | Beaupre |
| 6,309,400 | B2 | 10/2001 | Beaupre |
| 6,325,811 | B1 | 12/2001 | Messerly |
| 6,423,082 | B1 | 7/2002 | Houser et al. |
| 6,436,114 | B1 * | 8/2002 | Novak ............... A61B 17/32009 606/169 |
| 6,773,444 | B2 | 8/2004 | Messerly |
| 6,783,524 | B2 | 8/2004 | Anderson et al. |
| 8,057,498 | B2 | 11/2011 | Robertson |
| 8,152,825 | B2 | 4/2012 | Madan et al. |
| 8,461,744 | B2 * | 6/2013 | Wiener ............ A61B 17/32009 310/323.01 |
| 8,591,536 | B2 | 11/2013 | Robertson |
| 8,623,027 | B2 | 1/2014 | Price et al. |
| 8,911,460 | B2 | 12/2014 | Neurohr et al. |
| 2004/0064151 | A1 * | 4/2004 | Mollenauer ...... A61B 17/32009 606/205 |
| 2004/0193199 | A1 * | 9/2004 | Hashiguchi ...... A61B 17/32009 606/169 |
| 2005/0171531 | A1 * | 8/2005 | Eliachar ........... A61B 17/32002 606/46 |
| 2005/0187512 | A1 * | 8/2005 | Isola ................ A61B 17/32006 604/22 |
| 2006/0079874 | A1 | 4/2006 | Faller et al. |
| 2006/0259054 | A1 * | 11/2006 | Masuda ................ A61B 17/29 606/169 |
| 2007/0191713 | A1 * | 8/2007 | Eichmann .......... A61B 17/1606 600/471 |
| 2007/0282333 | A1 | 12/2007 | Fortson et al. |
| 2008/0200940 | A1 | 8/2008 | Eichmann et al. |
| 2008/0234711 | A1 * | 9/2008 | Houser ............ A61B 17/32006 606/169 |
| 2009/0030311 | A1 * | 1/2009 | Stulen ............. A61B 17/32009 600/439 |
| 2010/0069940 | A1 * | 3/2010 | Miller ............. A61B 17/32006 606/169 |
| 2010/0331873 | A1 * | 12/2010 | Dannaher ........ A61B 17/32009 606/169 |
| 2011/0087212 | A1 | 4/2011 | Aldridge et al. |
| 2011/0238067 | A1 * | 9/2011 | Moses ................ A61B 18/1442 606/52 |
| 2012/0112687 | A1 | 5/2012 | Houser et al. |
| 2012/0116265 | A1 | 5/2012 | Houser et al. |
| 2012/0245582 | A1 * | 9/2012 | Kimball ........... A61B 17/32009 606/41 |
| 2013/0110155 | A1 * | 5/2013 | Tsuchiya ................ A61B 17/28 606/205 |
| 2014/0005701 | A1 | 1/2014 | Olson et al. |
| 2014/0114334 | A1 | 4/2014 | Olson et al. |
| 2015/0080924 | A1 | 3/2015 | Stulen et al. |
| 2015/0080925 | A1 | 3/2015 | Schulte et al. |
| 2015/0265305 | A1 * | 9/2015 | Stulen ............. A61B 17/32006 606/169 |

* cited by examiner

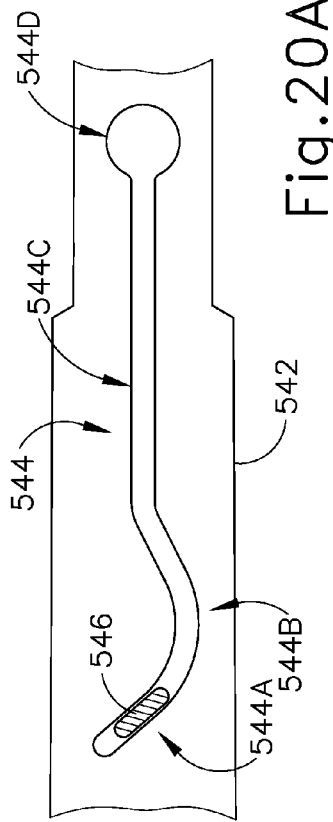
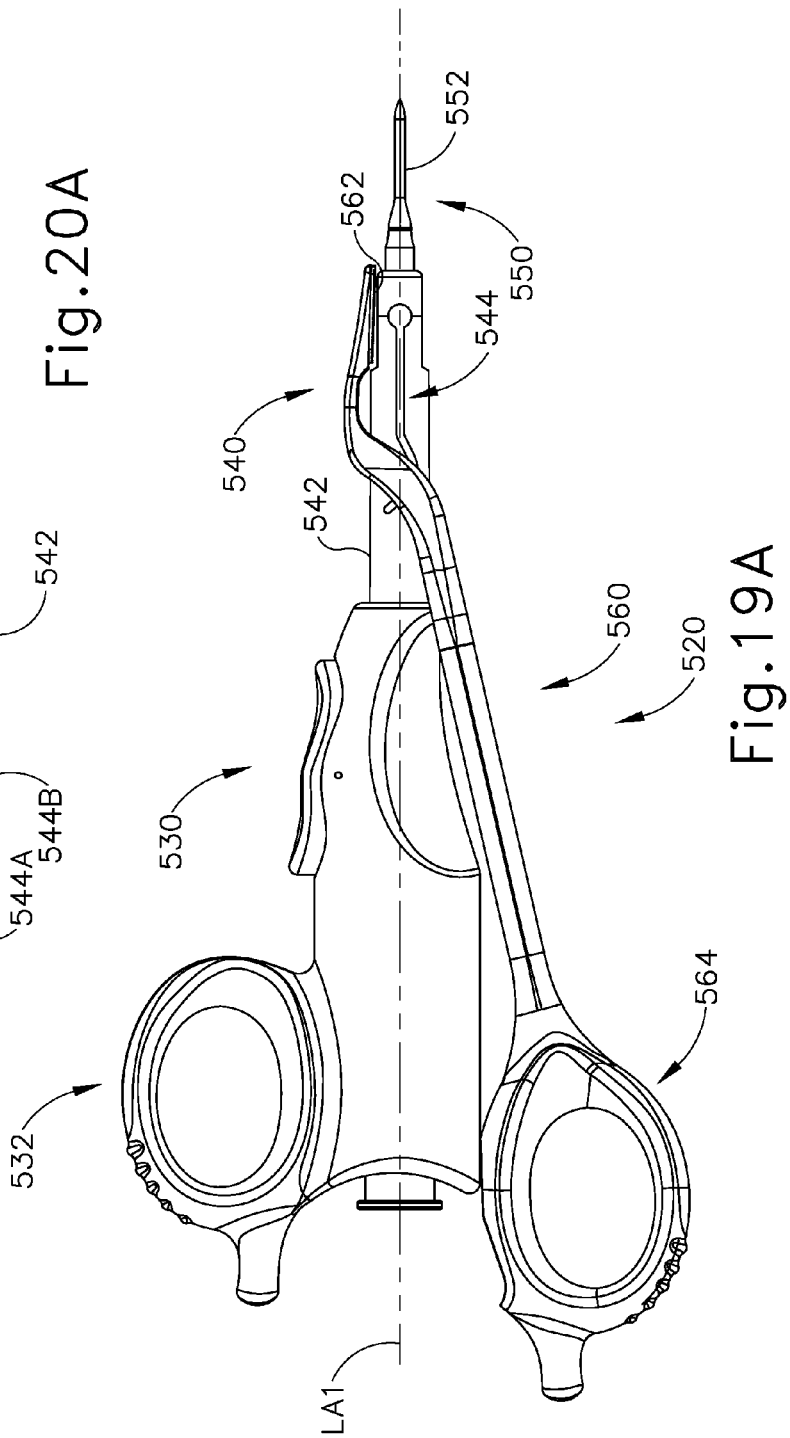

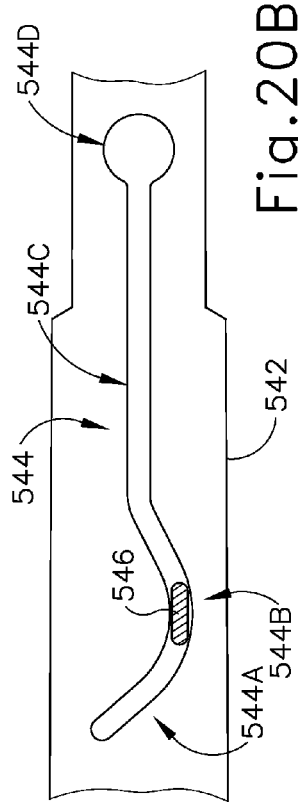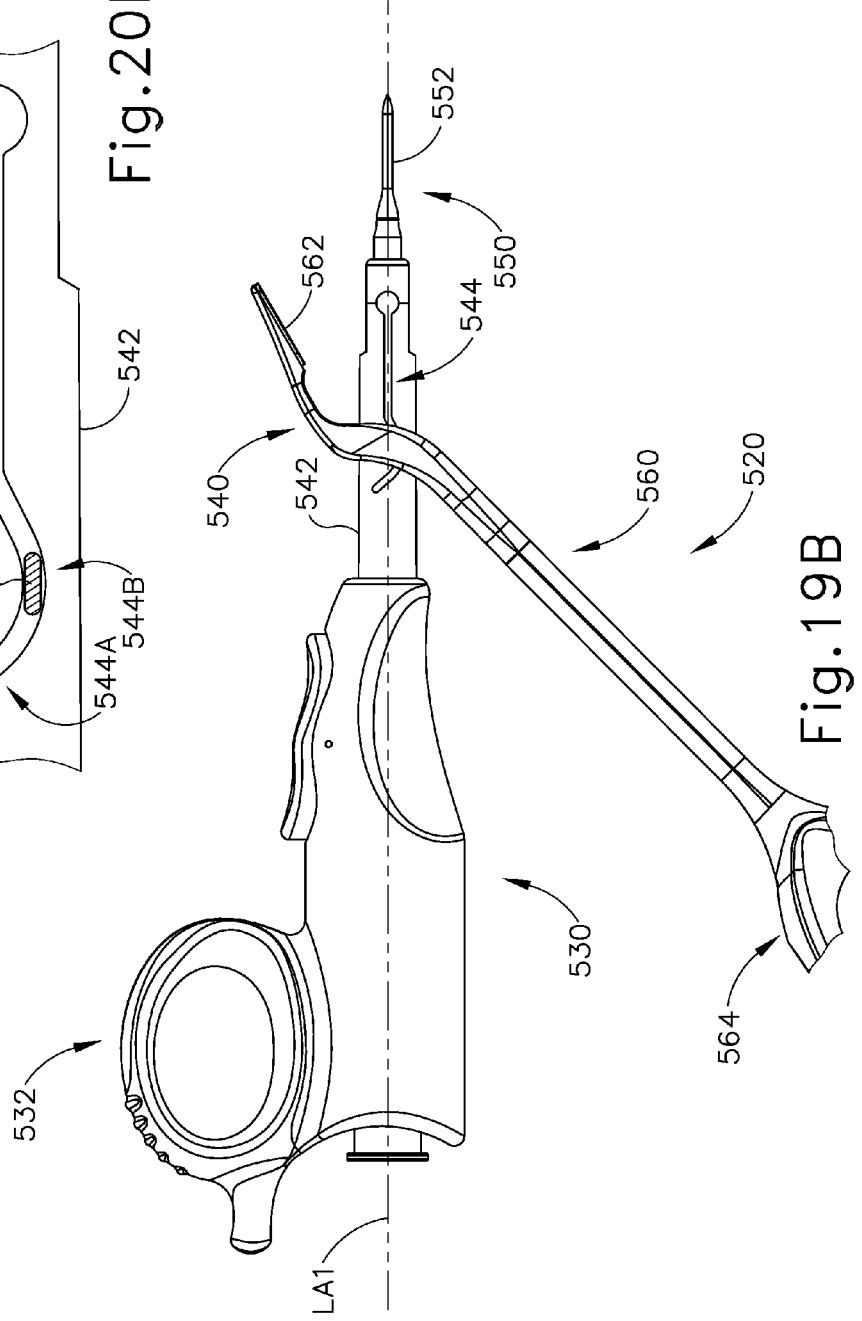

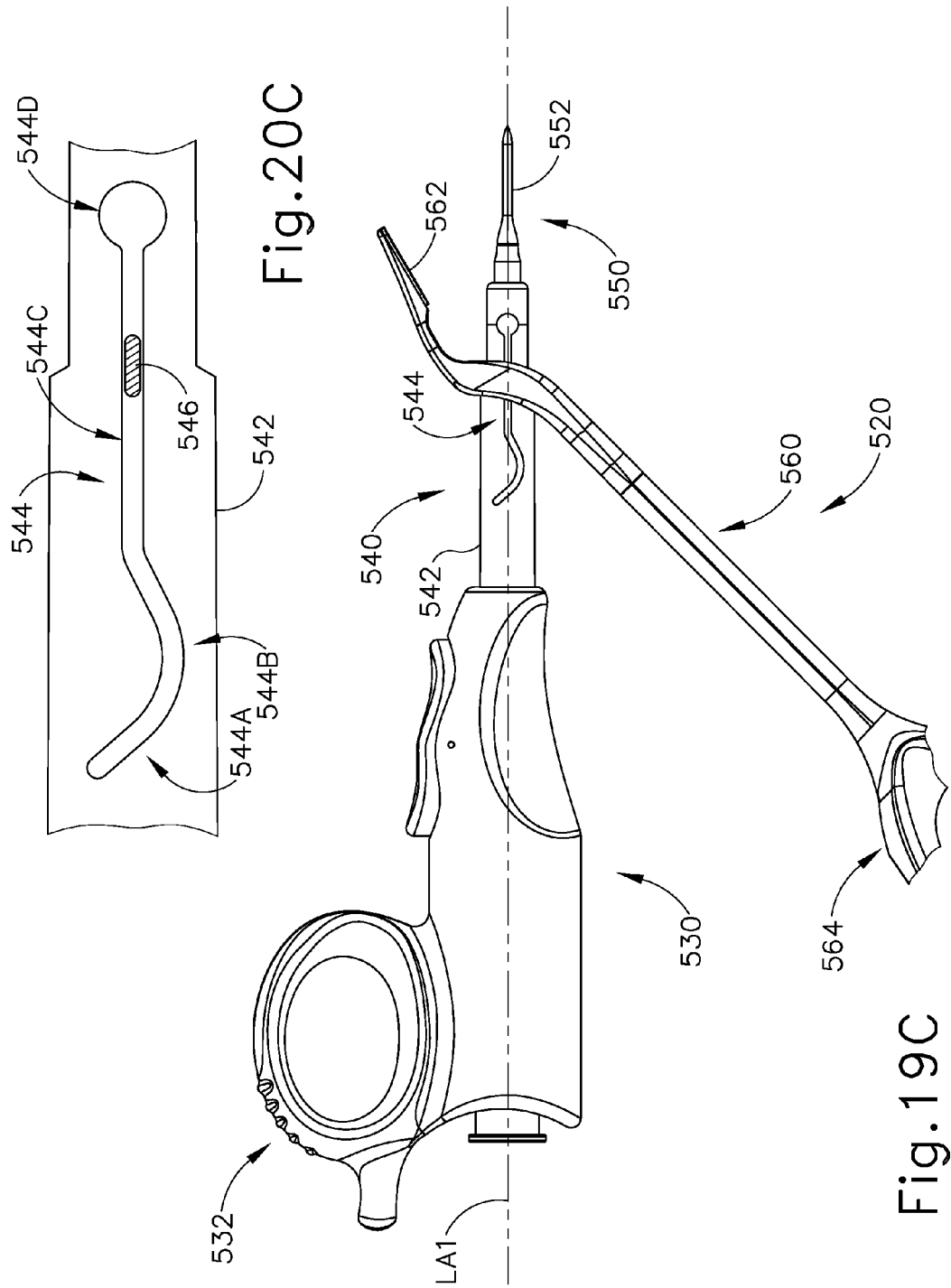

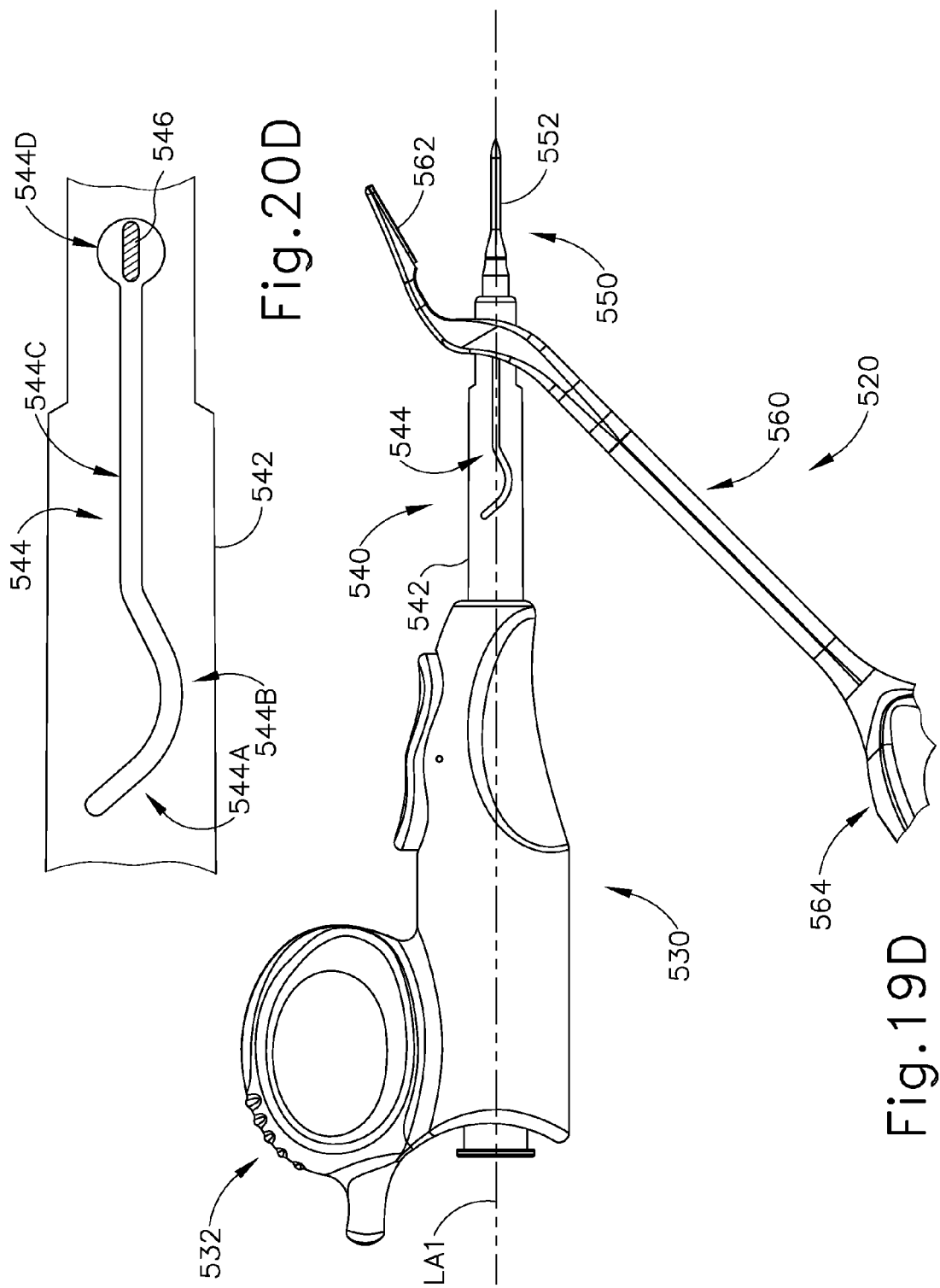

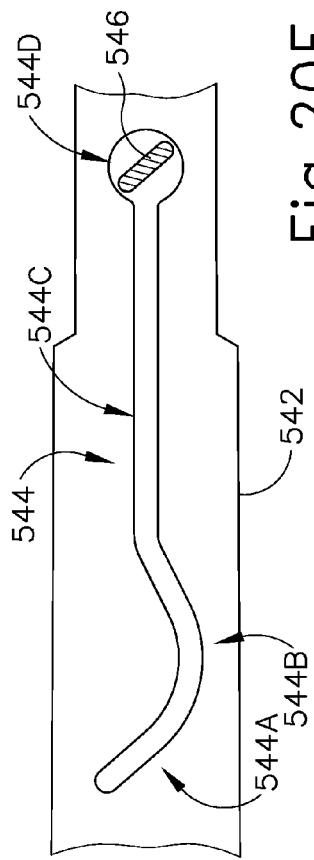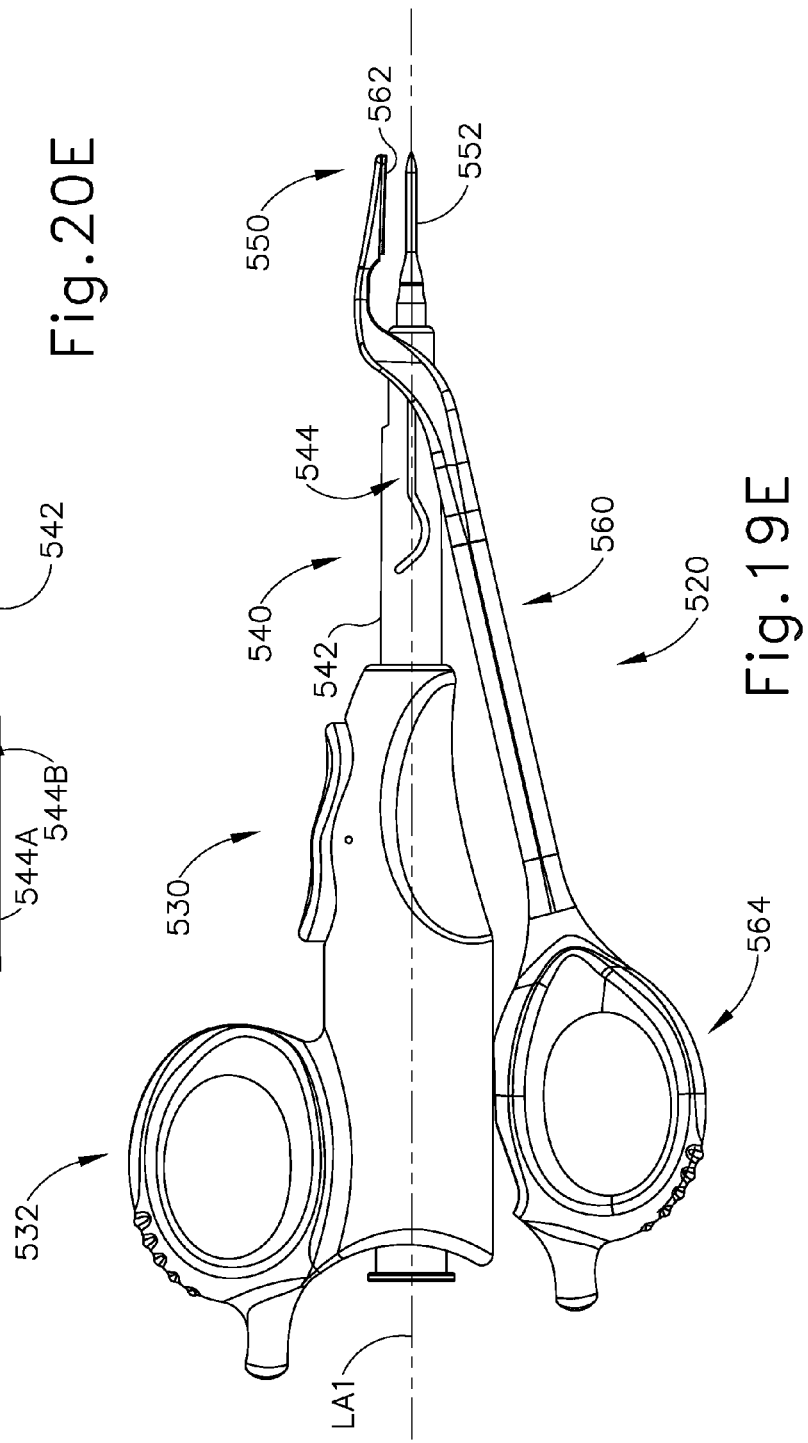

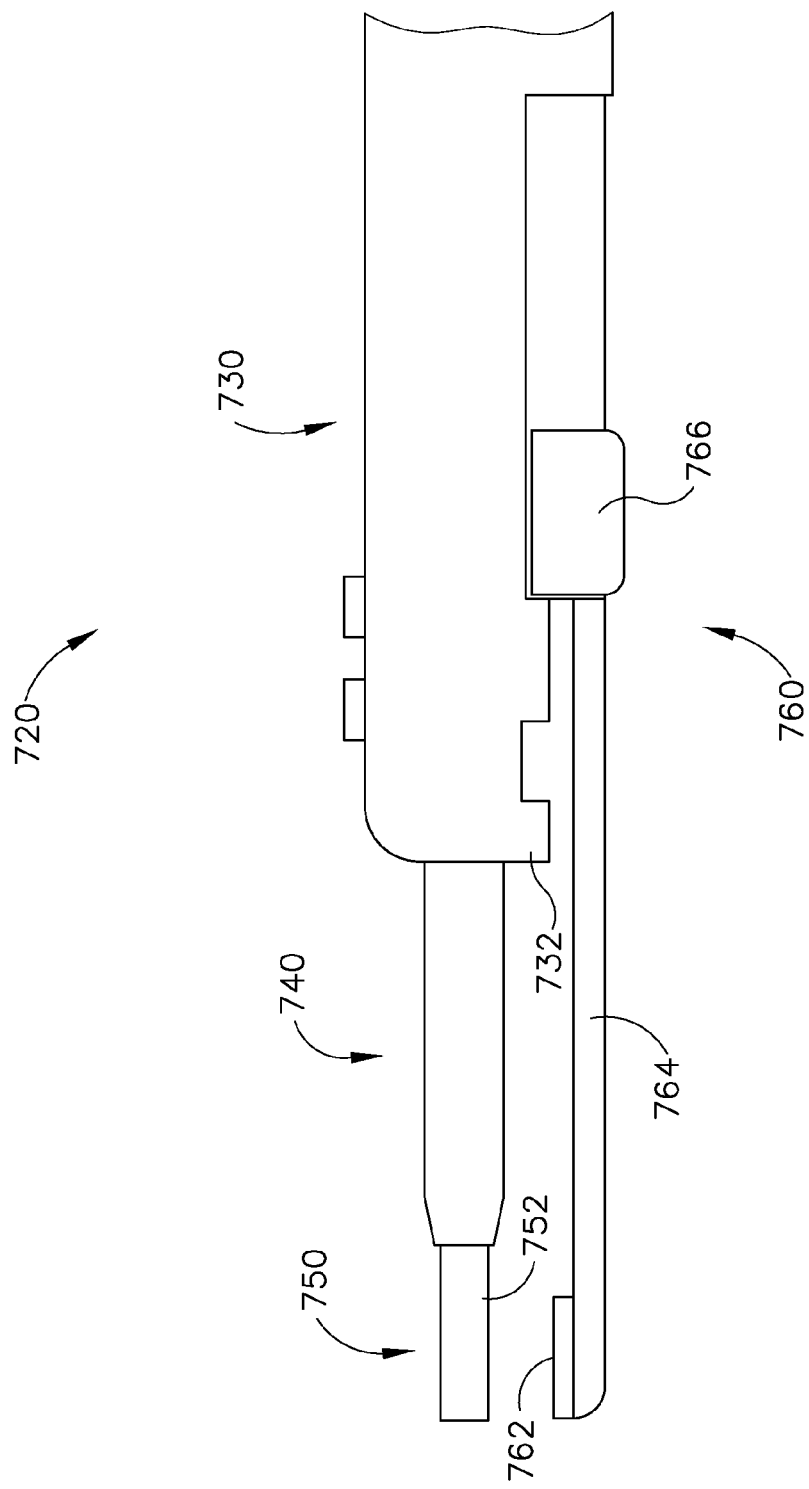

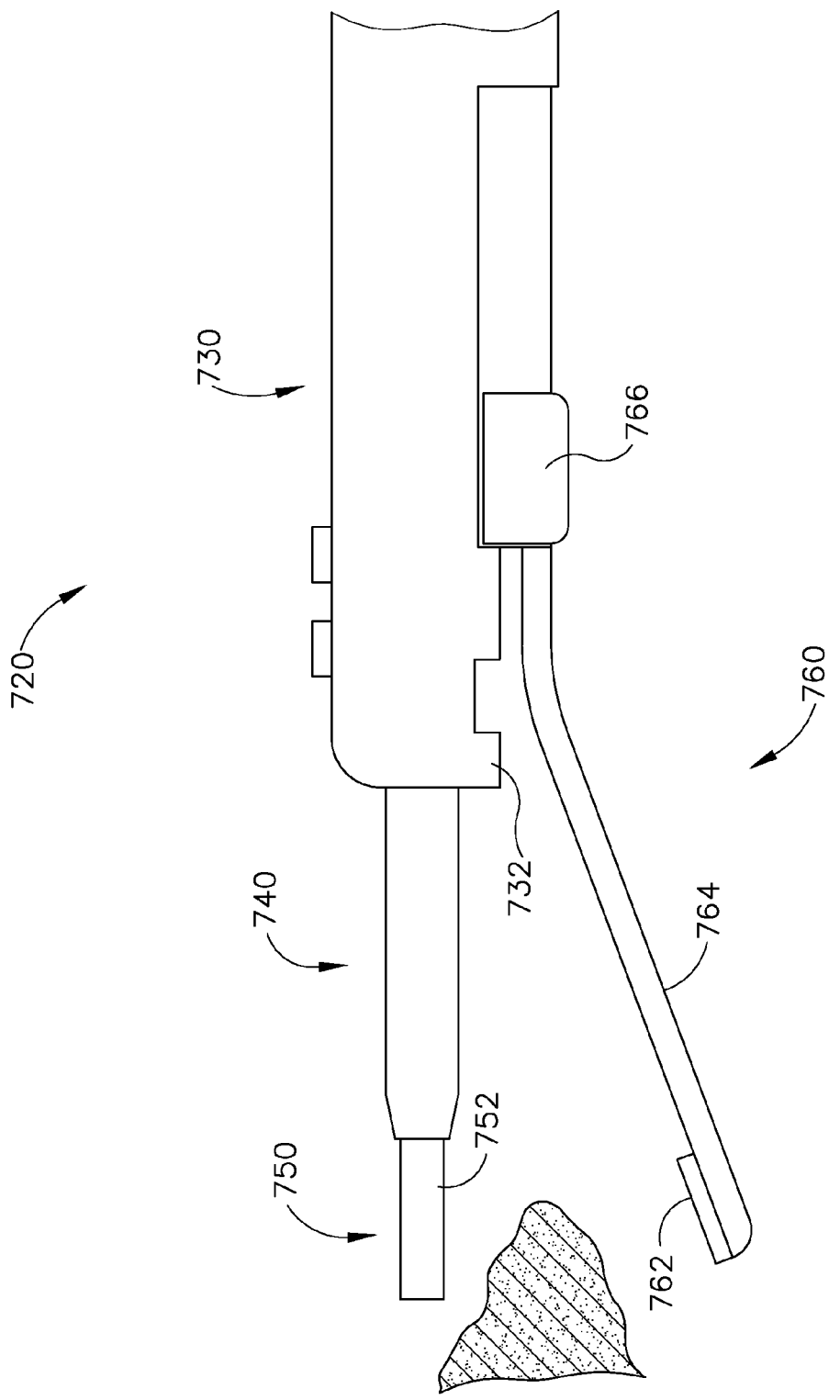

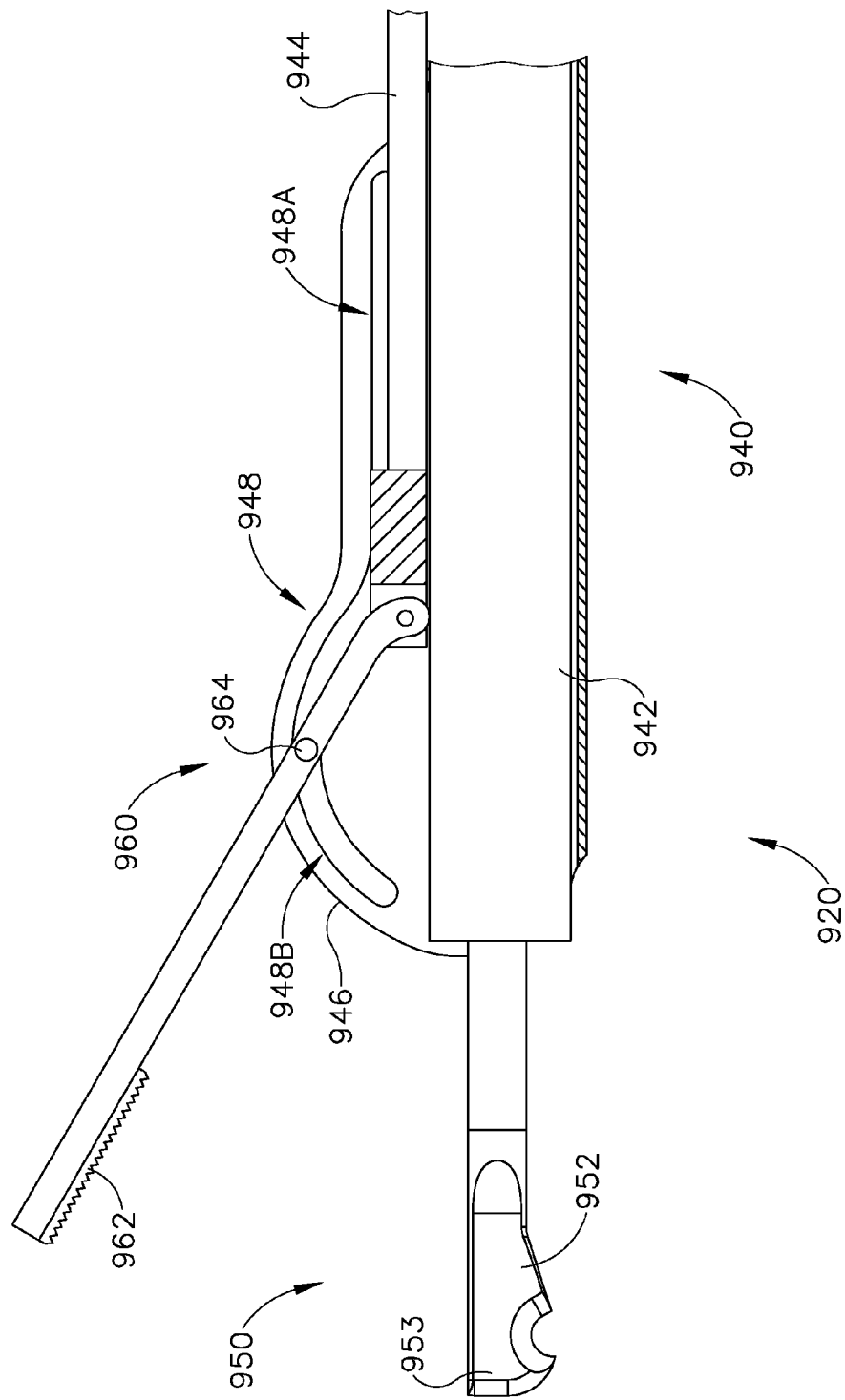

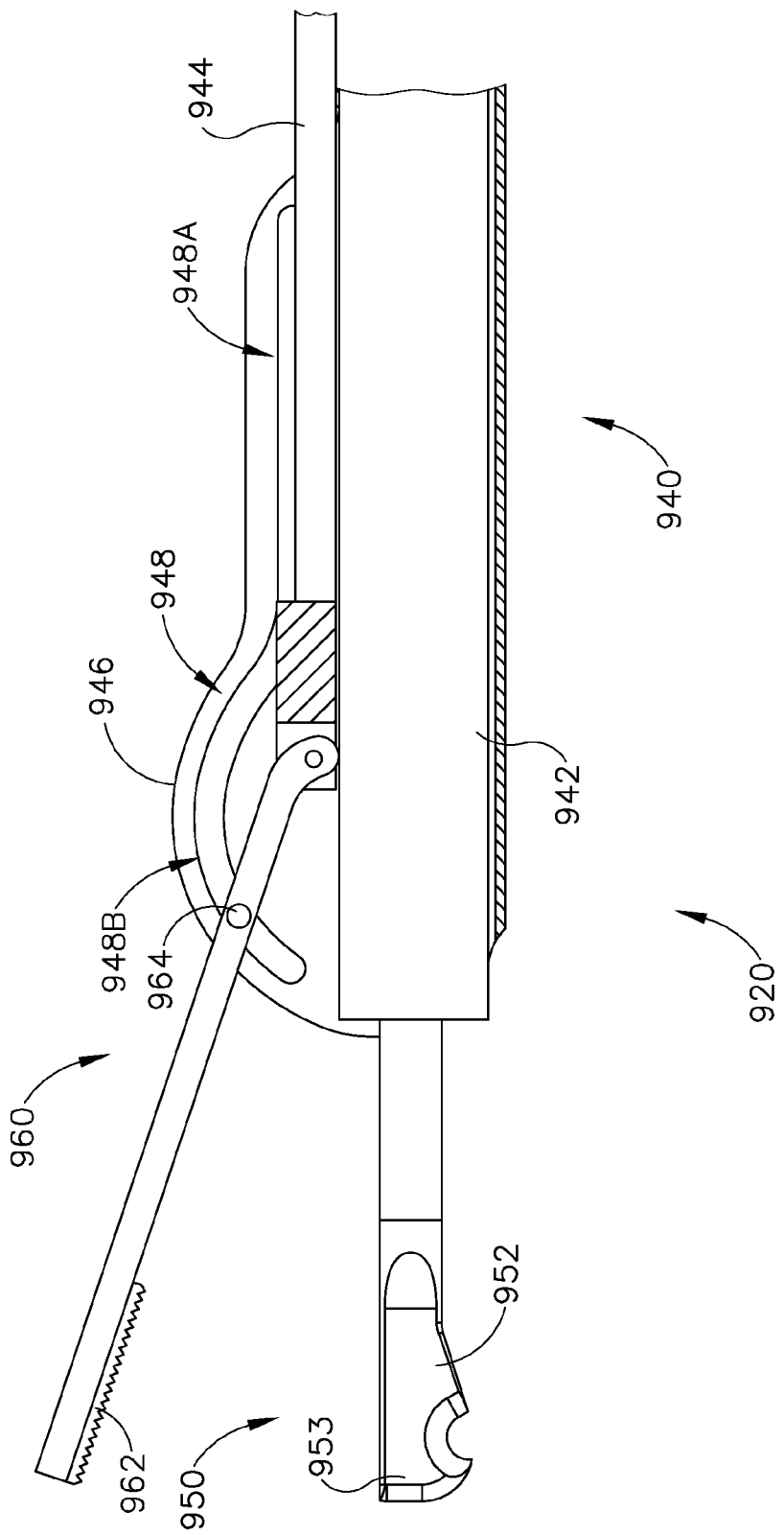

ULTRASONIC SURGICAL INSTRUMENT WITH RETRACTABLE INTEGRAL CLAMP ARM

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2008/0234710, entitled "Ultrasonic Surgical Instruments," published Sep. 25, 2008, now U.S. Pat. No. 8,911,460, issued Dec. 16, 2014, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," now U.S. Pat. No. 9,393,037, issued Jul. 19, 2016, the disclosure of which is incorporated by reference herein; and U.S. Pub. No. 2014/0114334, published Apr. 24, 2014, entitled "Flexible Harmonic Waveguides/Blades for Surgical Instruments," now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 19A depicts a side elevational view of the instrument of FIG. 16, with the clamp arm of FIG. 17 in a proximal position;

FIG. 19B depicts a side elevational view of the instrument of FIG. 16, with the clamp arm of FIG. 17 longitudinally translated and rotated into a first intermediate position;

FIG. 19C depicts a side elevational view of the instrument of FIG. 16, with the clamp arm of FIG. 17 longitudinally translated and rotated into a second intermediate position;

FIG. 19D depicts a side elevational view of the instrument of FIG. 16, with the clamp arm of FIG. 17 longitudinally translated into a distal position;

FIG. 19E depicts a side elevational view of the instrument of FIG. 16, with the clamp arm of FIG. 17 longitudinally translated to the distal position, and with the clamp arm further pivoted to a partially closed position;

FIG. 20A depicts a side elevational view of the clamp arm of FIG. 17, with a tab of the clamp arm shown in cross-section, engaged with the slot of FIG. 16 in the proximal position;

FIG. 20B depicts a side elevational view of the clamp arm of FIG. 17, with a tab of the clamp arm shown in cross-section, engaged with the slot of FIG. 16 in the first intermediate position;

FIG. 20C depicts a side elevational view of the clamp arm of FIG. 17, with a tab of the clamp arm shown in cross-section, engaged with the slot of FIG. 16 in the second intermediate position;

FIG. 20D depicts a side elevational view of the clamp arm of FIG. 17, with a tab of the clamp arm shown in cross-section, engaged with the slot of FIG. 16 in the distal position;

FIG. 20E depicts a side elevational view of the clamp arm of FIG. 17, with a tab of the clamp arm shown in cross-section, engaged with the slot of FIG. 16 in the distal position and further rotated from the position shown in FIG. 20D;

FIG. 21B depicts a side elevational view of the distal end of the instrument of FIG. 21A with the clamp arm longitudinally translated into a distal position;

FIG. 21C depicts a side elevational view of the distal end of the instrument of FIG. 21A with the clamp arm in the distal position and flexed into an open position;

FIG. 26D depicts a cross-sectional side elevational view of the instrument of FIG. 24 with the clamp arm longitudinally translated and rotated into a third intermediate position;

FIG. 26E depicts a cross-sectional side elevational view of the instrument of FIG. 24 with the clamp arm longitudinally translated and rotated into a fourth intermediate position;

Figure 1:
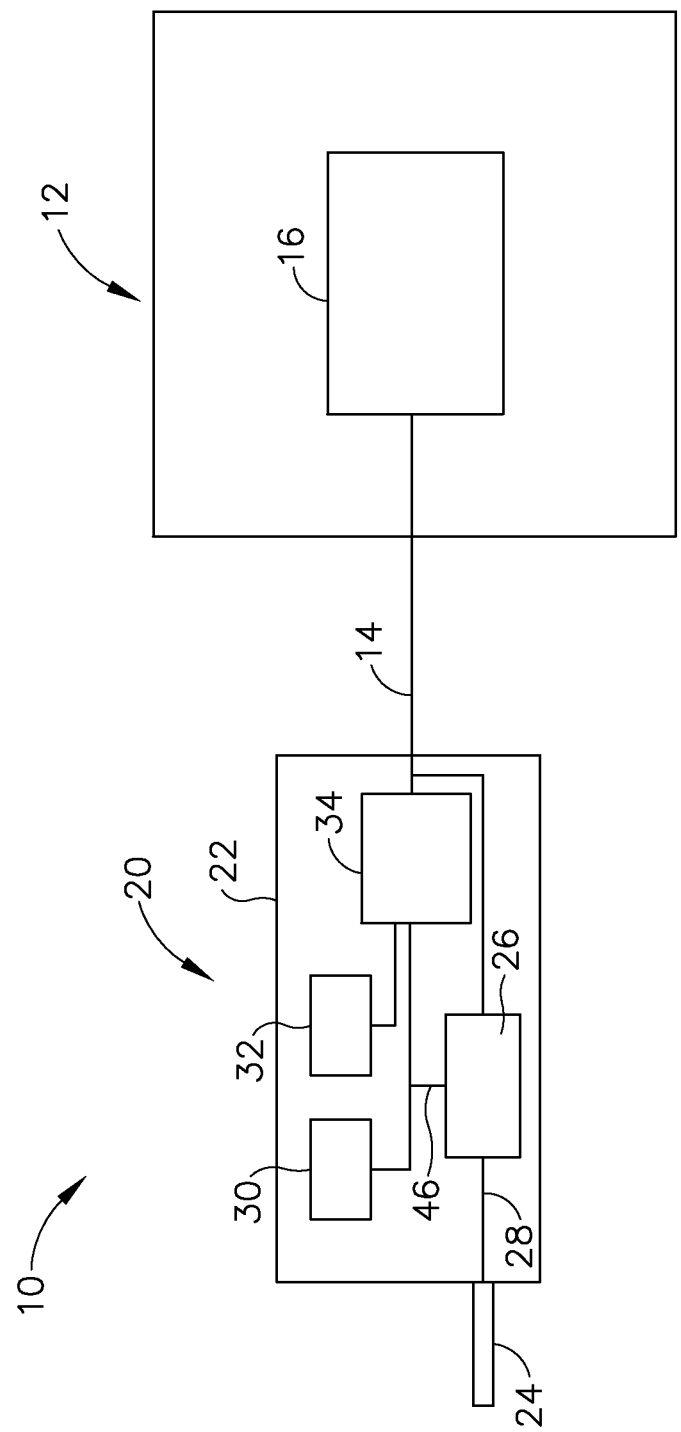
FIG. 1 depicts a block schematic view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths (n$\lambda$/2). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instruments

The following discussion relates to various exemplary components and configurations for instrument (20) and components thereof. It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 1-54 illustrate exemplary ultrasonic surgical instruments (120, 220, 320, 420, 520, 620, 720, 820, 920, 1020, 1120). At least part of each instrument (120, 220, 320, 420, 520, 620, 720, 820, 920, 1020, 1120) may be constructed and operable in accordance with at least some of the teachings of U.S. Pat. Nos. 5,322,055; 5,873,873; 5,980,510; 6,325,811; 6,773,444; 6,783,524; 8,461,744; U.S. Pub. No. 2009/0105750, now U.S. Pat. No. 8,623,027, issued on Jan. 7, 2014; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071; U.S. Pub. No. 2012/0112687, now U.S. Pat. No. 9,381,058; U.S. Pub. No. 2012/0116265; U.S. Pub. No. 2014/0005701, now U.S. Pat. No. 9,393,037; U.S. Pat. Pub. No. 2014/0114334, now U.S. Pat. No. 9,095,367; U.S. patent application Ser. No. 14/028,717, now U.S. Pub. No. 2015/0080924, published Mar. 19, 2015; and/or U.S. Pat. App. No. 61/410,603. The disclosures of each of the foregoing patents, publications, and applications are incorporated by reference herein. As described therein and as will be described in greater detail below, each instrument (120, 220, 320, 420, 520, 620, 720, 820, 920, 1020, 1120) is operable to cut tissue and seal or weld tissue (e.g., a blood vessel, etc.) substantially simultaneously. It should also be understood that instruments (120, 220, 320, 420, 520, 620, 720, 820, 920, 1020, 1120) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instruments (120, 220, 320, 420, 520, 620, 720, 820, 920, 1020, 1120) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instruments (120, 220, 320, 420, 520, 620, 720, 820, 920, 1020, 1120), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

III. Exemplary Ultrasonic Scalpel Instrument

Figure 2:
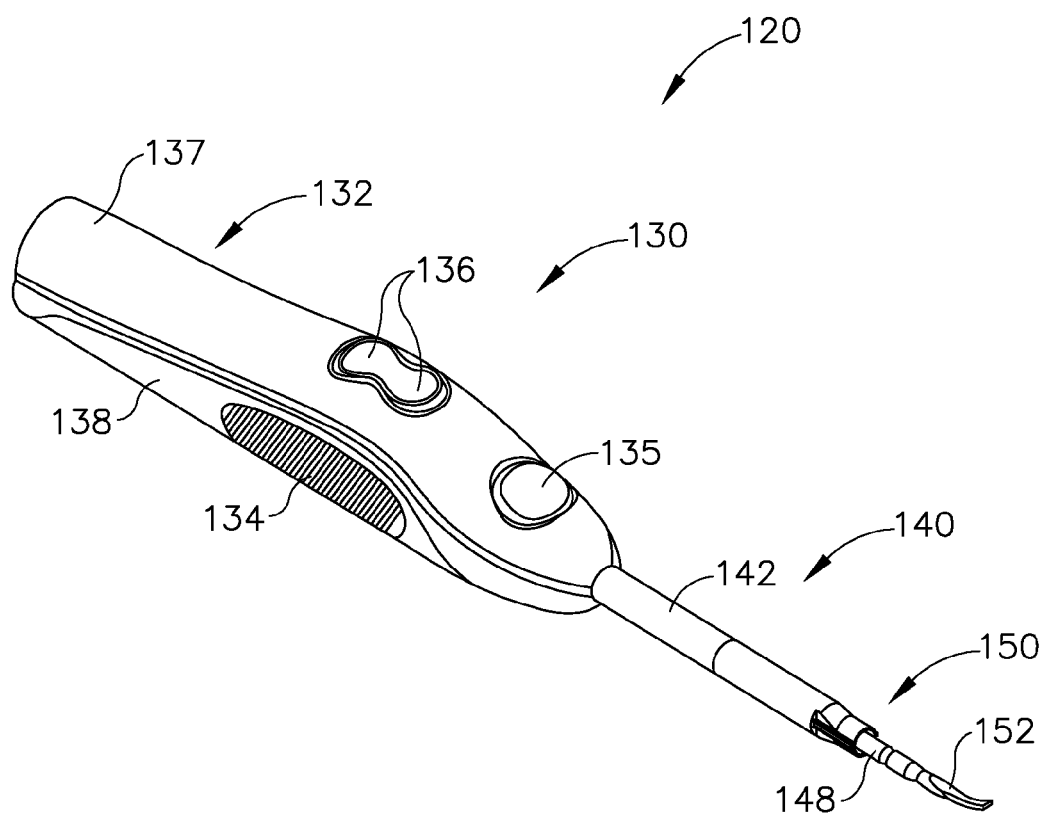
FIG. 2 depicts a perspective view of an exemplary alternative surgical instrument.
Figure 3:
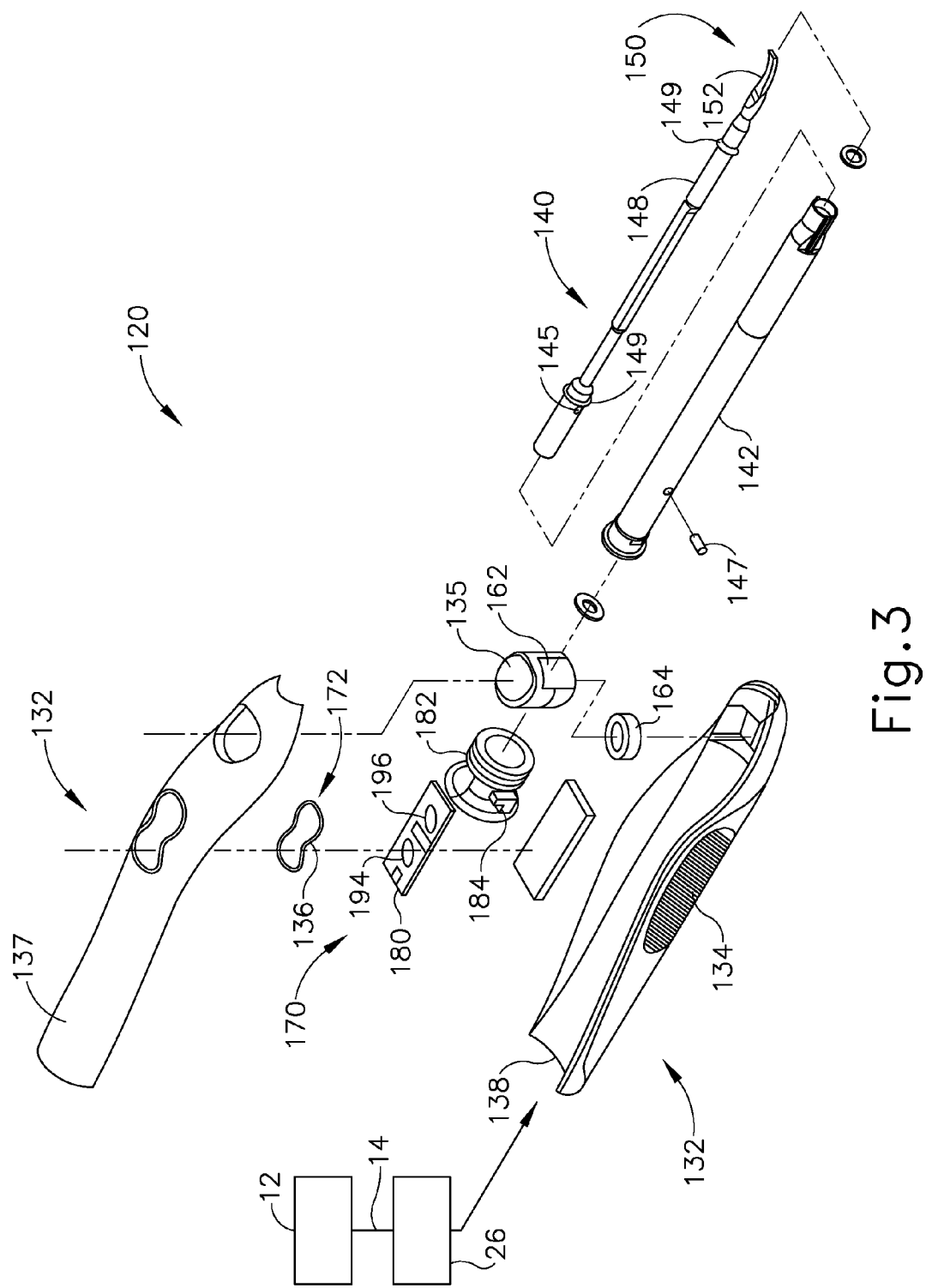
FIG. 3 depicts an exploded perspective view of the instrument of FIG. 2.

FIGS. 2 and 3 illustrate an exemplary ultrasonic surgical instrument (120) that is configured to be used as a scalpel (e.g., in facial plastic surgery, etc.). Instrument (120) may be used in conjunction with ultrasonic surgical system (10) which includes ultrasonic transducer (26) coupled with ultrasonic generator (12) via cable (14). Instrument (120) of this example comprises a handle assembly (130), a shaft assembly (140), and an end effector (150). In some versions, handle assembly (130) may receive ultrasonic transducer (26) which may couple to a waveguide (148) in shaft assembly (140) by a threaded connection, though any other suitable type of coupling may be used. Handle assembly (130) comprises a tubular elongate body (132) including a grip portion (134) and a plurality of buttons (135, 136). Handle assembly (130) omits any clamp arm, and instrument (120) is merely used as an ultrasonic scalpel for simultaneously slicing and cauterizing tissue. Thus, handle assembly (130) includes grip portion (134) which is configured to permit a user to grip handle assembly (130) from a variety of positions. By way of example only, handle assembly (130) may be shaped to be grasped and manipulated in a pencil-like arrangement. Handle assembly (130) of the present example comprises mating housing portions (137) and (138). While a multi-piece handle assembly (130) is illustrated, handle assembly (130) may alternatively comprise a single or unitary component. Handle assembly (130) may be constructed from a durable plastic, such as polycarbonate or a liquid crystal polymer. It is also contemplated that handle assembly (130) may alternatively be made from a variety of materials or combinations of materials, including but not limited to other plastics, ceramics, and/or metals, etc. In some versions, the proximal end of instrument (120) receives and is fitted with ultrasonic transducer (26) by insertion of ultrasonic transducer (26) into handle assembly (130). Instrument (120) may be attached to and removed from ultrasonic transducer (26) as a unit.

As shown in FIG. 3, shaft assembly (140) comprises an outer sheath (142), and a waveguide (148) disposed within outer sheath (142). Waveguide (148), which is configured to transmit ultrasonic energy from transducer (26) to an ultrasonic blade (152), may be flexible, semi-flexible or rigid. Waveguide (148) may also be configured to amplify the mechanical vibrations transmitted through waveguide (148) to blade (152). Waveguide (148) may further include at least one bore (145) extending therethrough, substantially perpendicular to the longitudinal axis of waveguide (148). Bore (145) is located at a longitudinal position corresponding to a node associated with ultrasonic vibrations communicated along waveguide (148). Bore (145) is configured to receive a connector pin (147), which connects ultrasonic waveguide (148) to outer sheath (142).

As mentioned above, end effector (150) omits any clamp arm. Instead, end effector (150) merely consists of ultrasonic blade (152) which may be used for simultaneously slicing and cauterizing tissue. In some alternative versions, including but not limited to those described below, end effector (150) may include a clamp arm. Blade (152) may be integral with ultrasonic waveguide (148) and formed as a single unit. In some versions, blade (152) may be connected to waveguide (148) by a threaded connection, a welded joint, and/or some other coupling feature(s). The distal end of blade (152) is disposed at or near a longitudinal position corresponding to an anti-node associated with ultrasonic vibrations communicated along waveguide (148) and blade (152) in order to tune the acoustic assembly to a preferred resonant frequency $f_o$ when the acoustic assembly is not loaded by tissue. When transducer (26) is energized, the distal end of blade (152) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (152) may also vibrate in the y-axis at about 1 to about 10 percent of the motion in the x-axis. Of course, movement of blade (152) may alternatively have any other suitable characteristics.

Waveguide (148) is positioned within outer sheath (142) and held in place via pin (147). Pin (147) may be made of any compatible metal, such as stainless steel or titanium or a durable plastic, such as polycarbonate or a liquid crystal polymer. Alternatively, any other suitable material or combination of materials may be used. In some versions, pin (147) is partially coated with an elastomeric material, such as silicon, etc., for the portion of pin (147) that extends through ultrasonic waveguide (148). Elastomeric material may provide insulation from the vibrating blade throughout the length of bore (145). In some settings, this may enable high efficiency operation whereby minimal overheating is generated and maximum ultrasonic output power is available at the distal end of blade (152) for cutting and coagulation, etc. Of course, such elastomeric material is merely optional.

As can be seen in FIG. 3, waveguide (148) has a plurality of acoustic isolators (149) positioned along the longitudinal length of waveguide (148). Isolators (149) may provide structural support to waveguide (148); and/or acoustic isolation between waveguide (148) and other portions of shaft assembly (140). Isolators (149) generally have a circular or ovular cross-section and extend circumferentially around the diameter of waveguide (148). The inner diameter of each isolator (149) is generally sized slightly smaller than the outer diameter of waveguide (148) to create a slight interference fit, thus securing each isolator (149) to waveguide (148). In some examples, waveguide (148) may include annular, recessed channels that are configured to receive each isolator (149) to further aid in securing each isolator (149) along the longitudinal length of waveguide (148). In the present example, each isolator (149) is positioned at or near to an acoustic node along the longitudinal length of waveguide (148) (i.e., a longitudinal position corresponding to a node associated with resonant ultrasonic vibrations communicated through waveguide (148)). Such positioning may reduce the vibrations transferred to isolators (149) (and to other components in contact with isolators (149)) via waveguide (148).

Outer sheath (142) passes through an aperture (162) of release button (135). A spring (164) is positioned below button (135) and resiliently biases button (135) upwardly. The upward force imposed by spring (164) causes the perimeter of aperture (162) to firmly assert pressure against outer sheath (142), and thereby selectively prevents outer sheath (142), waveguide (148), and ultrasonic blade (152) from either rotating within handle assembly (130) or axially translating with respect to handle assembly (130). When the operator exerts a downward force on button (135), spring (164) is compressed and it no longer asserts a holding force on outer sheath (142). The operator may then axially translate outer sheath (142), waveguide (148), and blade (152) relative to handle assembly (130) and/or rotate outer sheath (142), waveguide (148), and blade (152) relative to handle assembly (130). Accordingly, it should be understood that the longitudinal and/or rotational position of blade (152) relative to handle assembly (130) may be selectively adjusted by the operator while depressing button (135), while still allowing blade (152) to vibrate ultrasonically at such selected positions, allowing blade (152) to be used in various surgical procedures at such selected positions. To initiate such ultrasonic action of blade (152), the operator may operate a footswitch (not shown), activate pair of buttons (136) as described below, activate a button on generator (12), or perform some other act on some component of system (10).

In the present example, body (132) of handle assembly (130) includes a proximal end, a distal end, and a cavity (139) extending longitudinally therein. Cavity (139) is configured to accept a switch assembly (170) and at least a portion of ultrasonic transducer assembly (26). In some versions, the distal end of transducer (26) threadably attaches to the proximal end of waveguide (148), though any other suitable type of coupling may be used. Electrical contacts of transducer (26) also interface with switch assembly (170) to provide the operator with finger-activated controls on surgical instrument (120). Transducer (26) of the present example includes two conductive rings (not shown) which are securely disposed within the body of transducer (26). Merely exemplary transducers having such conductive rings are also described in U.S. Pub. No. 8,152,825, entitled "Medical Ultrasound System and Handpiece and Methods for Making and Tuning," issued Apr. 10, 2012, the disclosure of which is incorporated by reference herein. Switch assembly (170) of the present example comprises a pushbutton assembly (172), a circuit assembly (180), a switch housing (182), a first pin conductor (184), and a second pin conductor (not shown). Switch housing (182) is annular-shaped and is supported within handle assembly (130) by way of corresponding supporting mounts on switch housing (182) and body (132).

Pushbutton assembly (172) of the present example comprises pair of buttons (136). Circuit assembly (180) provides for the electro-mechanical interface between pair of buttons (136) and generator (12) via transducer (26). Circuit assembly (180) comprises two dome switches (194, 196) that are mechanically actuated by depressing each button of pair of buttons (136). Dome switches (194, 196) are electrical contact switches, that when depressed provide an electrical signal to generator (12). In particular, various components of circuit assembly (180) interface with transducer (26) via the ring conductors of transducer (26), which are in turn connected to conductors in cable (14) that connects to generator (12). In an exemplary operation, when the operator depresses one button of the pair of buttons (136), generator (12) may respond with a certain energy level, such as a maximum ("max") power setting. When the operator depresses another button of the pair of buttons (136), generator (12) may respond with a certain energy level, such as a minimum ("min") power setting, which conforms to accepted industry practice for pushbutton location and the corresponding power setting. Instrument (120) may further be configured and operable in accordance with the teachings of U.S. Pub. No. 2008/0200940, entitled "Ultrasonic Energy Device for Cutting and Coagulating," published Aug. 21, 2008, the disclosure of which is incorporated by reference herein. Alternatively, instrument (120) may be provided with a variety of other components, configurations, and/or types of operability as will be apparent to those of ordinary skill in the art in view of the teachings herein.

In addition to or in lieu of being constructed in accordance with the above teachings, at least part of instrument (120) may be constructed and operable in accordance with at least some of the teachings of U.S. Pat. Nos. 5,322,055; 5,873,873; 5,980,510; 6,283,981; 6,309,400; 6,325,811; 6,423,082; 6,783,524; 8,057,498; 8,461,744; U.S. Pub. No. 2006/0079874; U.S. Pub. No. 2007/0191713; U.S. Pub. No. 2007/0282333; U.S. Pub. No. 2008/0200940; U.S. Pub. No. 2008/0234710, now U.S. Pat. No. 8,911,460; U.S. Pub. No. 2010/0069940, now U.S. Pat. No. 9,023,071; U.S. Pub. No. 2012/0112687, now U.S. Pat. No. 9,381,058; U.S. Pub. No. 2012/0116265; U.S. Pub. No. 2014/0005701, now U.S. Pat. No. 9,393,037; U.S. Pub. No. 2014/0114334, now U.S. Pat. No. 9,095,367; and/or U.S. Pat. App. No. 61/410,603. The disclosures of each of the foregoing patents, publications, and applications are incorporated by reference herein. Additional merely illustrative variations for instrument (120) will be apparent to those of ordinary skill in the art in view of the teachings herein. It should be understood that the below described variations may be readily applied to instrument (120) described above and any of the instruments referred to in any of the references that are cited herein, among others.

IV. Exemplary Modified Ultrasonic Scalpel Instrument with Retractable Clamp Arm

It will be appreciated by those of ordinary skill in the art that it may be desirable in some versions of instrument (120) to provide instrument (120) with a clamp arm. A clamp arm may be used to compress tissue against ultrasonic blade (152) before and/or during ultrasonic activation of ultrasonic blade (152). Such compression may promote hemostasis in tissue and/or cutting of tissue more quickly and/or more effectively than hemostasis and/or cutting that could otherwise be achieved by ultrasonic blade (152) without a clamp arm. For instance, such a clamp arm may be desirable to enable instrument (120) to achieve large vessel hemostasis, e.g. vessels larger than 1 mm-2 mm in diameter. It may further be desirable to provide such a clamp arm and/or instrument (120) with features which allow such a clamp arm to be easily advanced and/or retracted relative to end effector (150) of instrument (120), i.e. a "retractable" clamp arm. This may enable instrument (120) to selectively transition between two operational modes (one mode with clamp arm deployed and another mode with clamp arm retracted). The operator may thus chose whether to deploy or retract the clamp arm based on whether a clamp arm would be useful in a particular clinical setting. The operator may further switch between these modes within the same surgical procedure, if desired. By way of example only, an operator may choose to operate instrument with the clamp arm retracted to an inoperative position when the operator wishes to use instrument (120) to primarily cut tissue; and operate instrument with the clamp arm advanced to an operative position when the operator wishes to use instrument (120) to primarily coaptate tissue and/or coagulate tissue.

As will be described in more detail below, FIGS. 4-28C show examples of such exemplary ultrasonic scalpel instruments having retractable, integral clamp arms. Various examples of such clamp arms will be described in greater detail below; while other examples will be apparent to those of ordinary skill in the art according to the teachings herein. It should be understood that the instruments described below are configured to function substantially similar to instrument (120) described above except for the differences described below. In particular, the instruments described below may be used to cut tissue and seal or weld tissue (e.g., a blood vessel, etc.) substantially simultaneously.

In the examples described below, the operator manually drives the features that transition the clamp arm from an inoperative position to an operative position. In some variations, a resilient member (e.g., spring, etc.), a motorized feature, and/or other feature(s) is/are included to assist in driving the clamp arm from an inoperative position to an operative position. For instance, an instrument may include a pushbutton that triggers a clamp arm drive assembly, such that actuating the pushbutton releases a spring that drives a clamp arm from an inoperative position to an operative position. Other suitable ways in which a clamp arm may be assisted in the transition from an inoperative position to an operative position will be apparent to those of ordinary skill in the art in view of the teachings herein.

While the following examples are provided in the context of harmonic surgical instruments, it should be understood that the below teachings may also be readily incorporated into RF electrosurgical instruments. The clamp pad may be configured to include an RF return electrode. By way of example only, an RF electrosurgical instrument may be used with the clamp arm retracted to an inoperative position when the operator wishes to use the instrument in a monopolar mode; and the instrument may be used with the clamp arm advanced to an operative position when the operator wishes to use the instrument in a bipolar mode. Other suitable ways in which the teachings herein may be modified for incorporation into an RF electrosurgical context will be apparent to those of ordinary skill in the art in view of the teachings herein. Of course, the teachings herein may also be applied to instruments that provide both RF electrosurgical functionality and ultrasonic surgical functionality.

A. Exemplary Ultrasonic Scalpel with Hinged Clamp Arm

FIGS. 4-7C illustrate an exemplary alternative ultrasonic surgical instrument (220) configured to be used as a scalpel. Instrument (220) may be used in conjunction with ultrasonic surgical system (10) which includes ultrasonic transducer (26) coupled with ultrasonic generator (12) via cable (14). Instrument (220) of this example comprises a handle assembly (230), a shaft assembly (240), and an end effector (250). Instrument (220) is configured to operate substantially similar to instrument (120) discussed above except for the differences discussed below. In particular, instrument (220) may be used to cut tissue and seal or weld tissue (e.g., a blood vessel, etc.) substantially simultaneously. Unlike instrument (120) discussed above, however, instrument (220) of the present example comprises a retractable clamp arm (260). As will be discussed in more detail below, clamp arm (260) is configured to be pivoted between an "inoperative position" (FIGS. 5 and 7A), when a user does not wish to use clamp arm (260), and an "operative position" (FIGS. 4, 6, and 7B-7C), when the user desires to use clamp arm (260).

Figure 5:
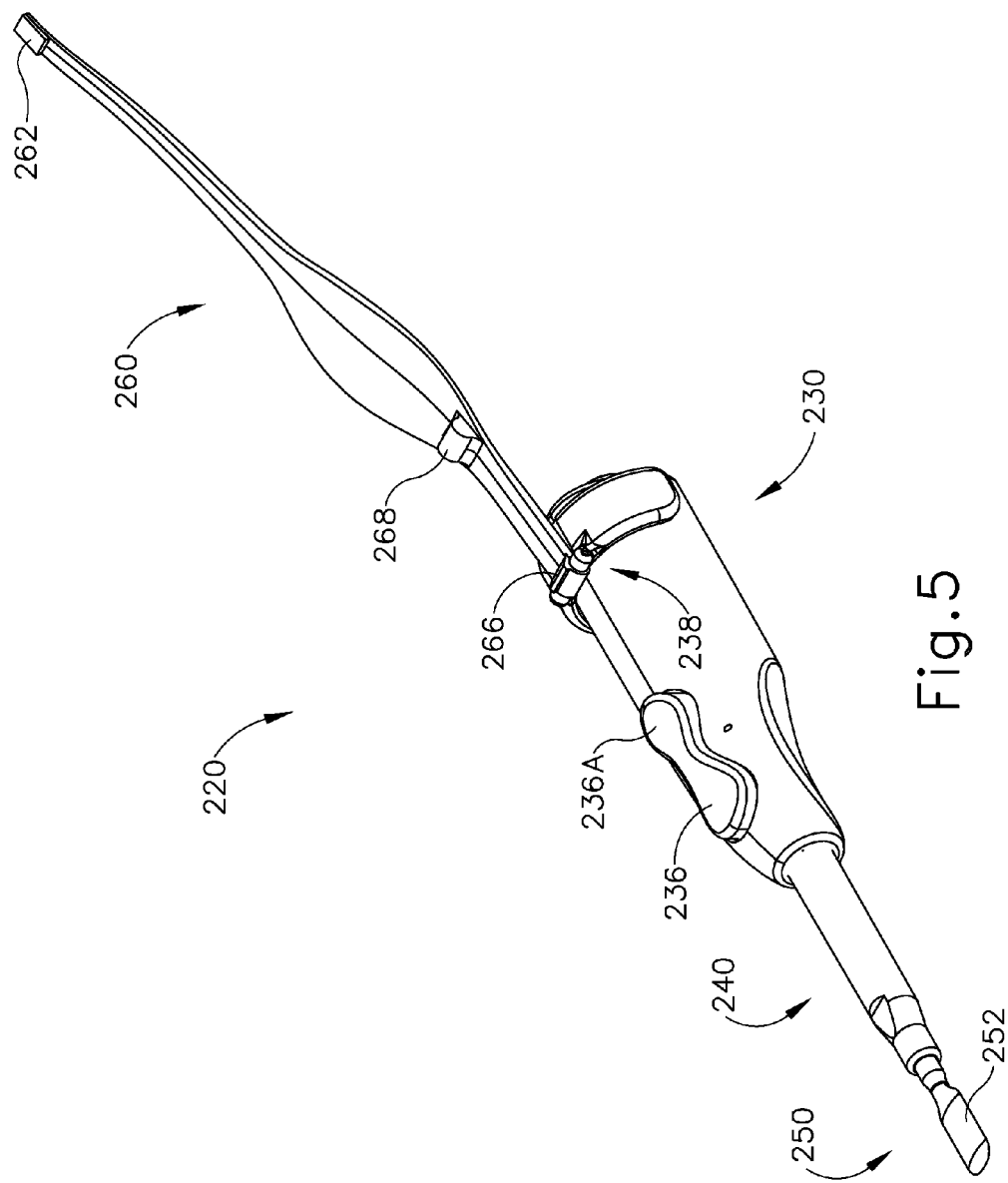
FIG. 5 depicts a perspective view of the instrument of FIG. 4 with the clamp arm in a proximal position.
Figure 7A:
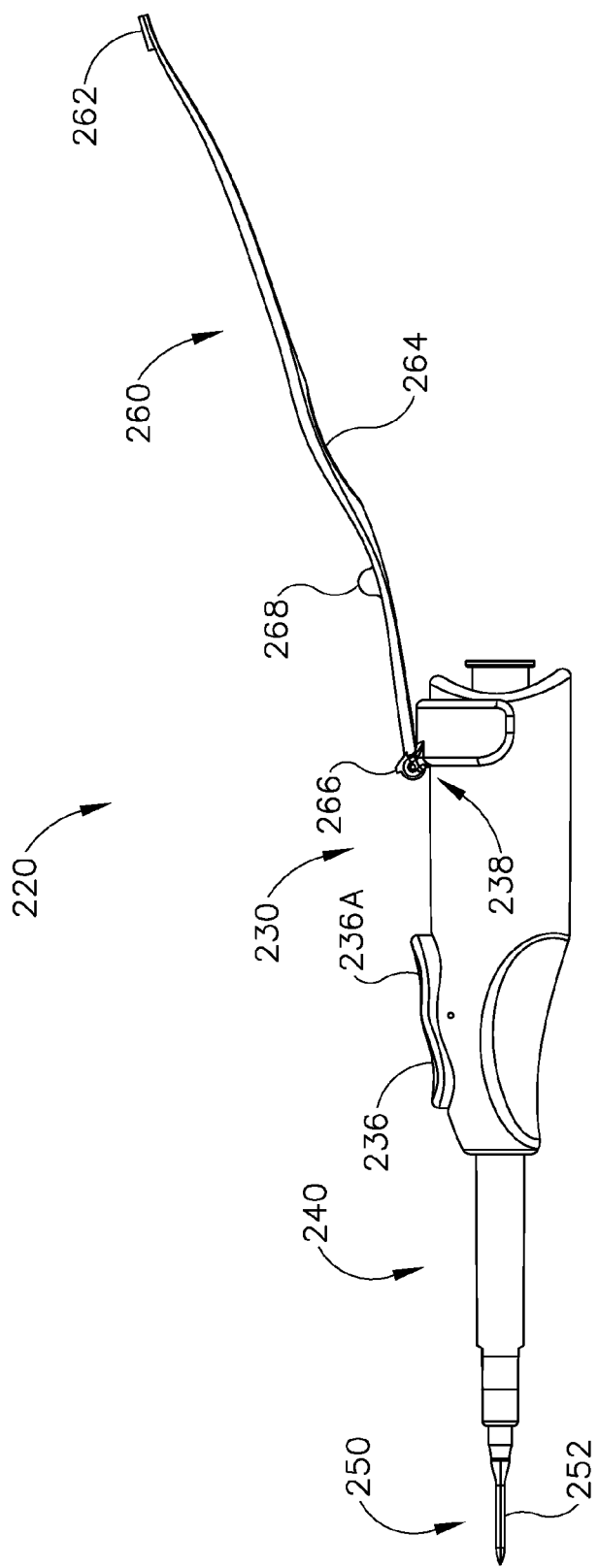
FIG. 7A depicts a side elevational view of the instrument of FIG. 4 with the clamp arm in the proximal position.
Figure 7B:
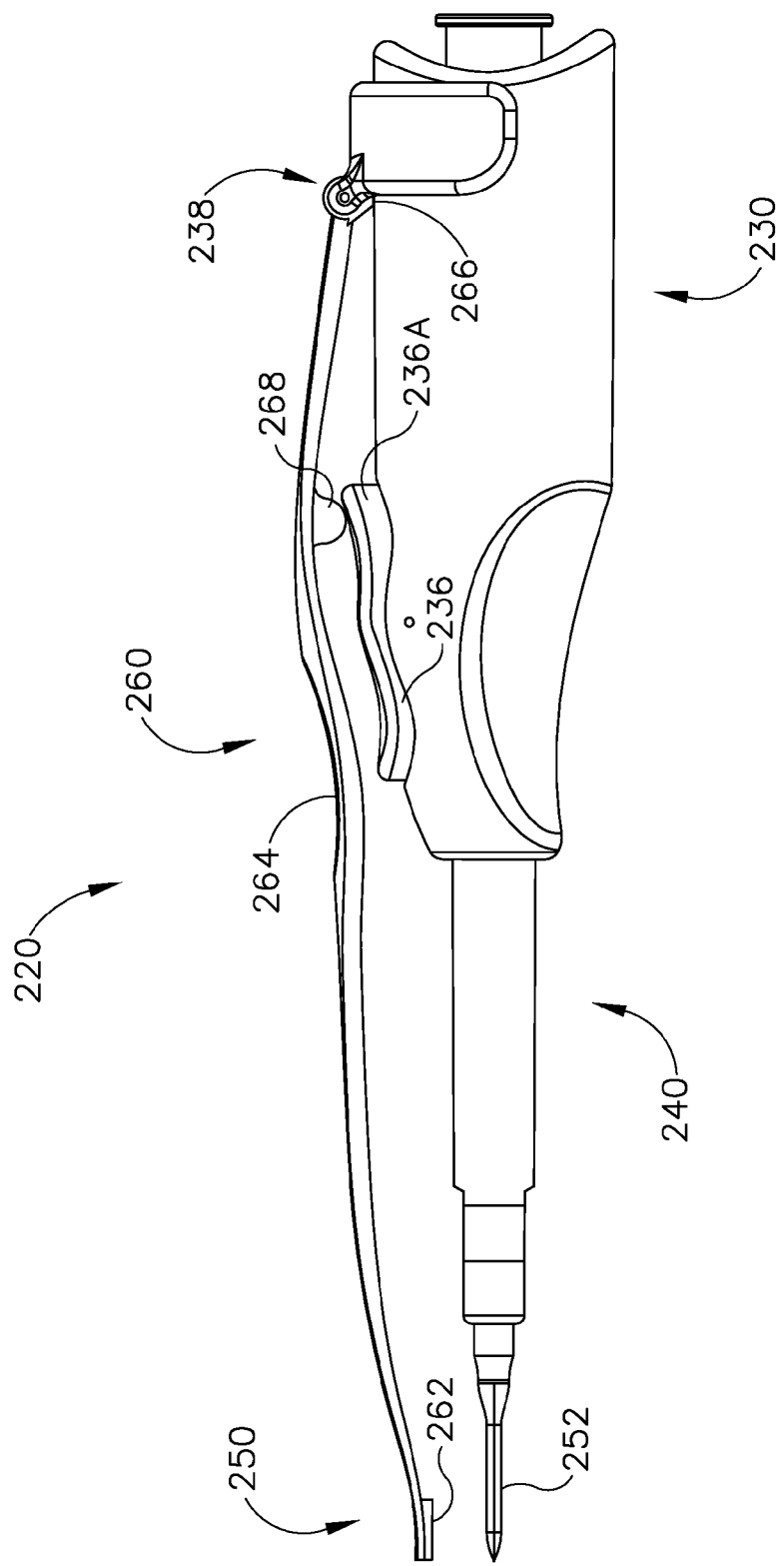
FIG. 7B depicts a side elevational view of the instrument of FIG. 4 with the clamp arm pivoted into the distal position such that a post of the clamp arm engages a button of the instrument.
Figure 7C:
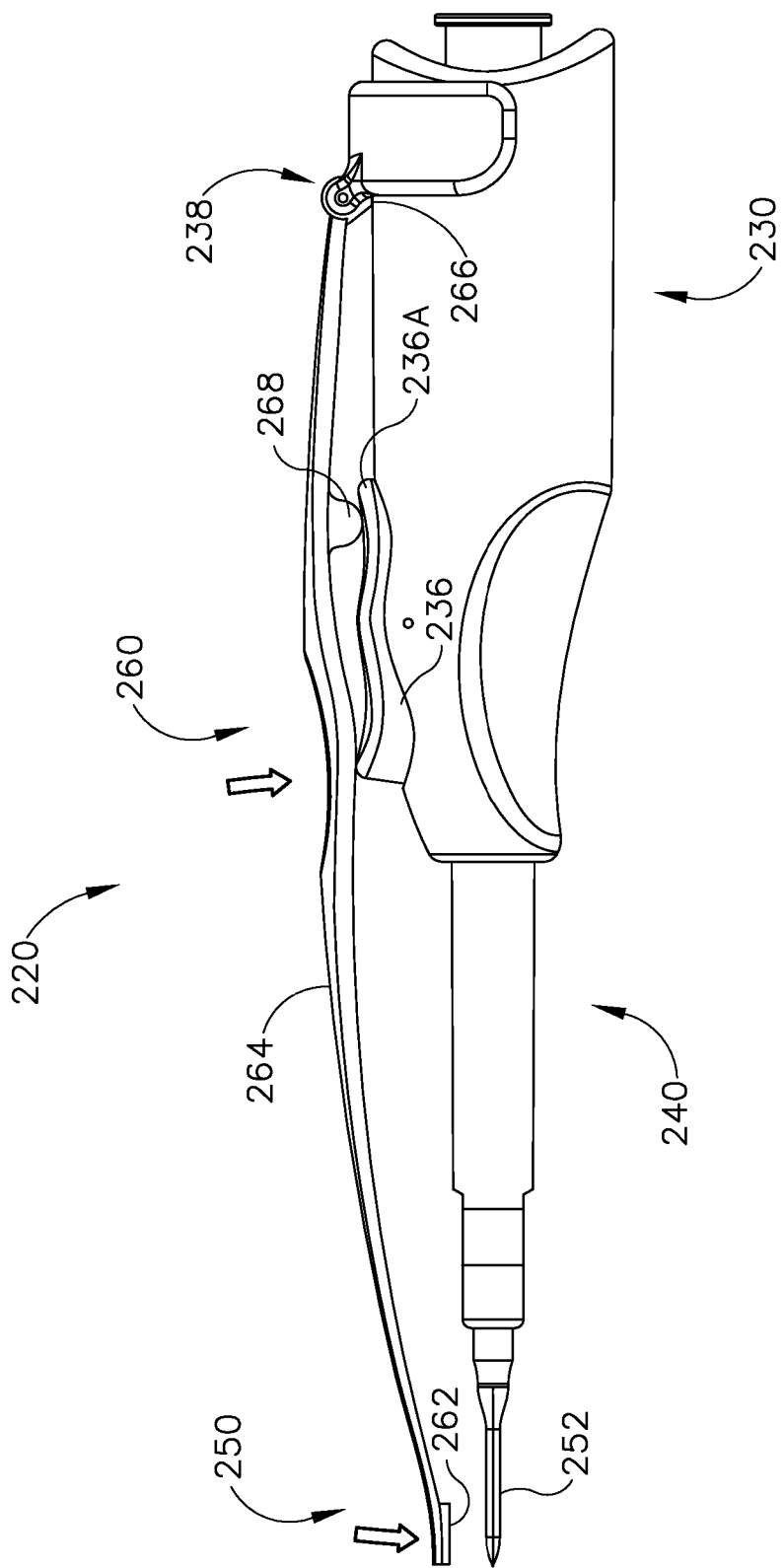
FIG. 7C depicts a side elevational view of the instrument of FIG. 4 with the clamp arm flexed toward the instrument such that the post of the clamp arm depresses the button of the instrument.
Figure 8:
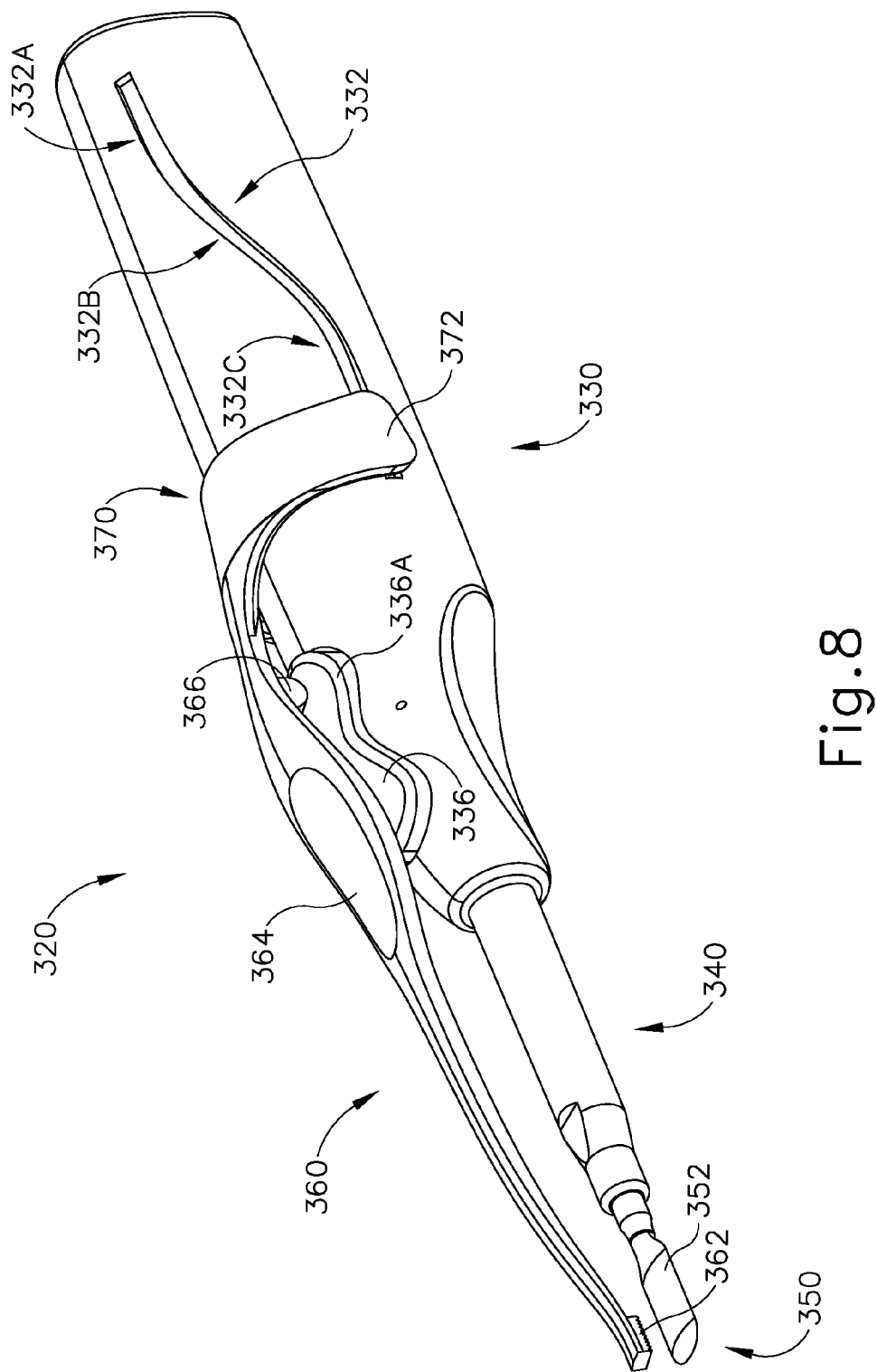
FIG. 8 depicts a perspective view of yet another exemplary alternative surgical instrument having a slidable and rotatable clamp arm in a distal position.
Figure 9:
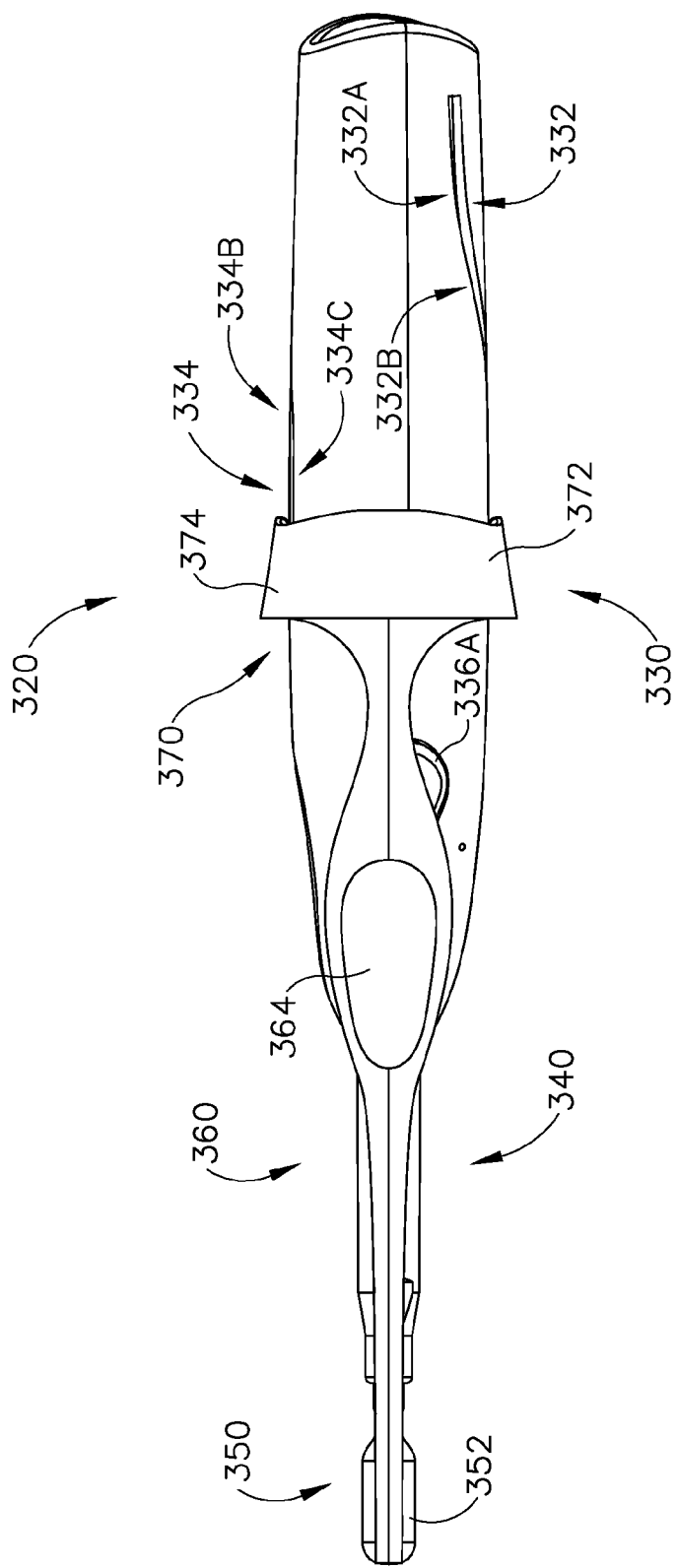
FIG. 9 depicts a top view of the instrument of FIG. 8 with the clamp arm in the distal position.

A proximal end of clamp arm (260) is pivotably coupled with a proximal portion of handle assembly (230) via a hinge (238) such that clamp arm (260) may be pivoted toward and away from handle assembly (230) between the "inoperative position" (FIG. 7A) and the "operative position" (FIG. 7B). As best seen in FIG. 5, a projection (266) extends laterally from a proximal end of clamp arm (260). As best seen in FIG. 7B, projection (266) is configured to engage a top surface of handle assembly (230) when clamp arm (260) is in the "operative position" so as to prevent further pivoting of clamp arm (260) at hinge (238) toward handle assembly (230). As will be discussed in more detail below, however, although clamp arm (260) is prevented from pivoting toward handle assembly (230) via hinge (238) when clamp arm (260) is in the "operative position," clamp arm (260) is nevertheless configured to flex toward handle assembly (230).

Figure 4:
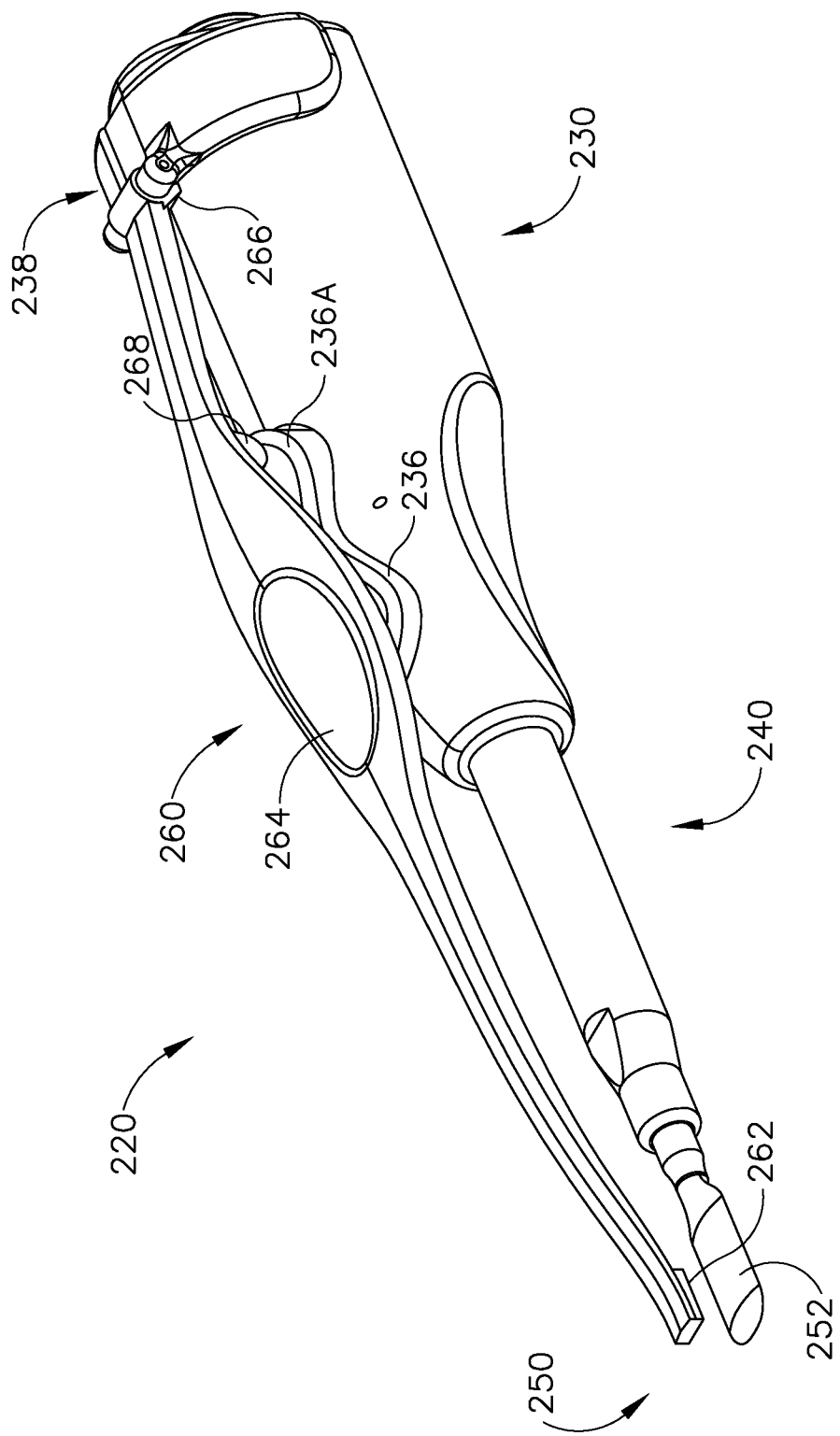
FIG. 4 depicts a perspective view of another exemplary alternative surgical instrument having a pivotable clamp arm in a distal position.

A distal end of clamp arm (260) comprises a clamp pad (262). In some versions, clamp pad (262) comprises polytetrafluoroethylene (PTFE). Alternatively, clamp pad (262) may comprise any other suitable material(s) as will be apparent to those of ordinary skill in the art in view of the teachings herein. With clamp arm (260) in the "operative position," clamp pad (262) is positioned directly above an ultrasonic blade (252) of end effector (250) as shown in FIGS. 4 and 7B. In the present example, a vertical gap exists between a bottom surface of clamp pad (262) and ultrasonic blade (252) clamp arm (260) is in the operative position. Tissue may be positioned within this gap. The operator may then force clamp arm (260) to flex downwardly into the position shown in FIG. 7C so as to capture the tissue between the bottom surface of clamp pad (262) and blade (252). For instance, the operator may use his or her index finger to force clamp arm (260) to flex downwardly, thereby compressing tissue between clamp pad (262) and ultrasonic blade (252). Clamp arm (260) comprises a post (268) extending from a bottom surface of clamp arm (260). As clamp arm (260) is flexed downwardly, post (268) bears against a button (236A) of a pair of buttons (236) of instrument (220), thereby depressing button (236A) and activating blade (252) as discussed above with reference to instrument (120). It should be appreciated that depression of button (236A) may correlate to generator (12) producing a "max" power setting, a "min" power setting, or any other setting. Thus, it should be understood that clamp arm (260) is configured to flex downwardly into the position shown in FIG. 7C to thereby simultaneously activate blade (252) and compress tissue between the bottom surface of clamp pad (262) and blade (252). It should also be understood that clamp arm (260) may be configured such that post (268) does not actuate button (236A) until tissue is significantly compressed between clamp pad (262) and blade (252). In other words, post (268) may not necessarily actuate button (236A) until there is no longer a gap between clamp pad (262) and blade (252). Clamp arm (260) may thus flex inwardly along the intermediate region of the length of clamp arm (260), at a location between hinge (238) and clamp pad (262), relative to hinge (238) and clamp pad (262).

Figure 6:
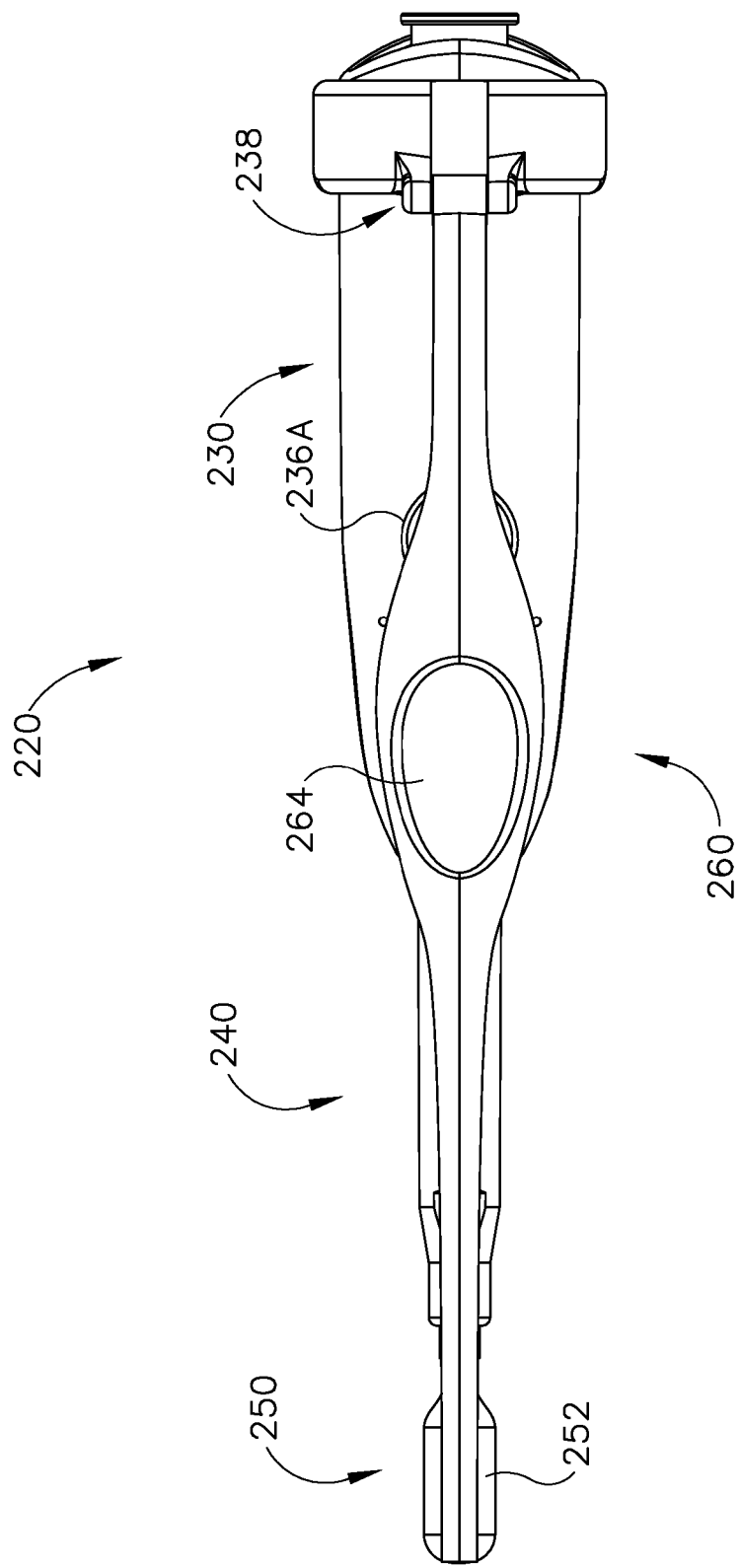
FIG. 6 depicts a top view of the instrument of FIG. 4 with the clamp arm in the distal position.

As best seen in FIGS. 4-6, blade (252) of the present example comprises a broad top surface so as to provide a broad surface for compression of tissue between blade (252) and clamp pad (262). The side surfaces of blade (252), on the other hand, are relatively thin such that the side surfaces of blade (252) may be used for cutting tissue without the assistance of clamp pad (262). It should be understood, however, that blade (252) may have any other suitable shape, including but not limited to any other ultrasonic blade shapes shown or described herein and/or shown or described in any of the references cited herein.

Clamp arm (260) comprises a finger pad (264). Finger pad (264) may provide for comfort and/or non-visual positioning of the operator's finger along clamp arm (260). For instance, finger pad (264) may comprise a recessed or raised portion or a material which contrasts with a material of clamp arm (260) such that finger pad (264) may be tactilely sensed by the operator. Finger pad (264) may also include ridges, knurling, elastomeric material, and/or other features that prevent the operator's finger from sliding along clamp arm (260) as the operator presses clamp arm (260) toward handle assembly (230).

In an exemplary use, the operator may readily transition instrument (220) between two modes of operation by pivoting clamp arm (260) between the operative position and the inoperative position. For instance, the operator may perform at least part of a surgical procedure with clamp arm (260) in the inoperative position, such that the operator uses ultrasonic blade (252) like a scalpel. The operator may thus grip and use instrument (220) in a manner similar to a grip and use of instrument (120) when clamp arm (260) is in the inoperative position. Within the same surgical procedure (or in a different surgical procedure), the operator may pivot clamp arm (260) to the operative position, then compress tissue between clamp pad (262) and ultrasonic blade (252) as described above. The operator may transition between these two modes as many times as desired within a given surgical procedure. Other suitable ways in which instrument (220) may be used will be apparent to those of ordinary skill in the art in view of the teachings herein.

B. Exemplary Ultrasonic Scalpel with Track-Guided Clamp Arm

FIGS. 8-14B illustrate another exemplary alternative ultrasonic surgical instrument (320) configured to be used as a scalpel. Instrument (320) may be used in conjunction with ultrasonic surgical system (10) which includes ultrasonic transducer (26) coupled with ultrasonic generator (12) via cable (14). Instrument (320) of this example comprises a handle assembly (330), a shaft assembly (340), and an end effector (350). Instrument (320) is configured to operate substantially similar to instrument (120) discussed above except for the differences discussed below. In particular, instrument (320) may be used to cut tissue and seal or weld tissue (e.g., a blood vessel, etc.) substantially simultaneously. Unlike instrument (120) discussed above, however, instrument (320) of the present example comprises a retractable clamp arm (360). As will be discussed in more detail below, clamp arm (360) is configured to be translated longitudinally and rotated between an "inoperative position" (FIGS. 13A and 14A), when a user does not wish to use clamp arm (360), and an "operative position" (FIGS. 8-11, 13B, and 14B), when the user desires to use clamp arm (360).

Figure 10:
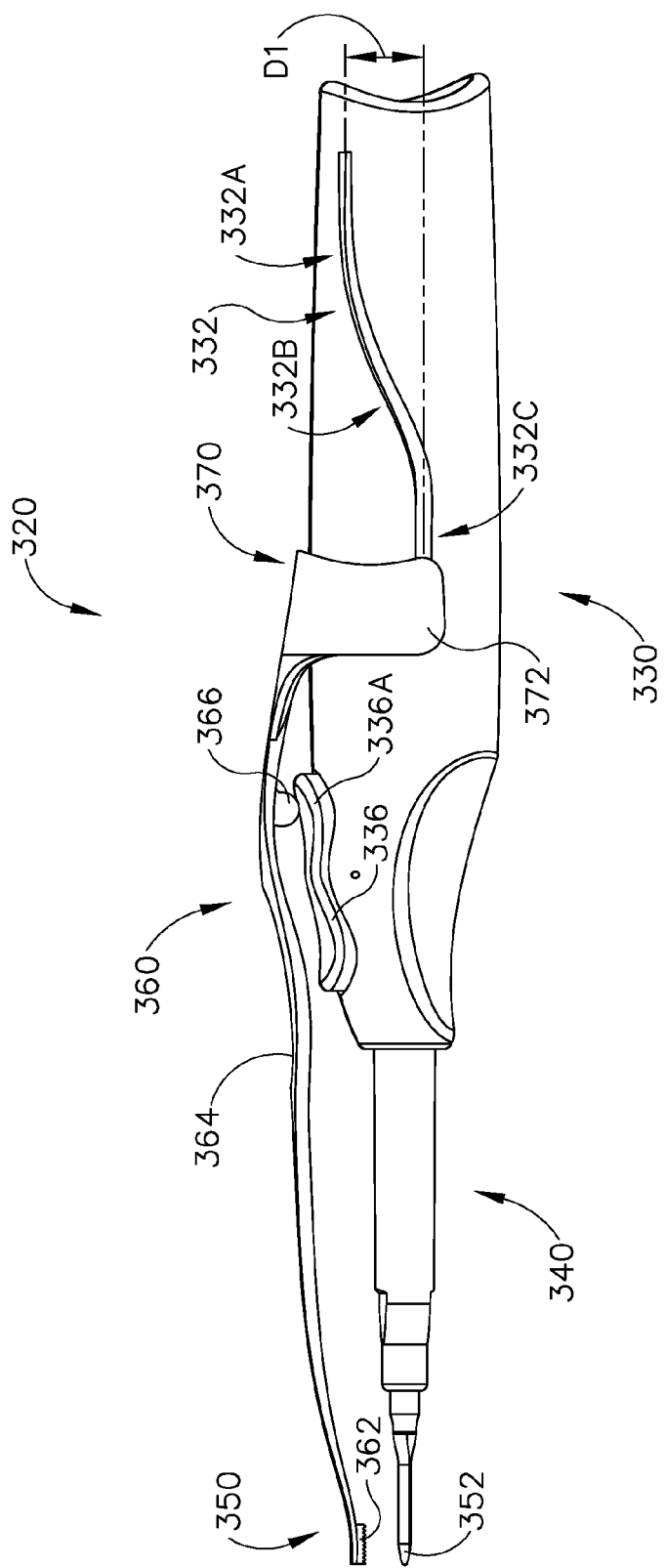
FIG. 10 depicts a side elevational view of the instrument of FIG. 8 with the clamp arm in the distal position.
Figure 11:
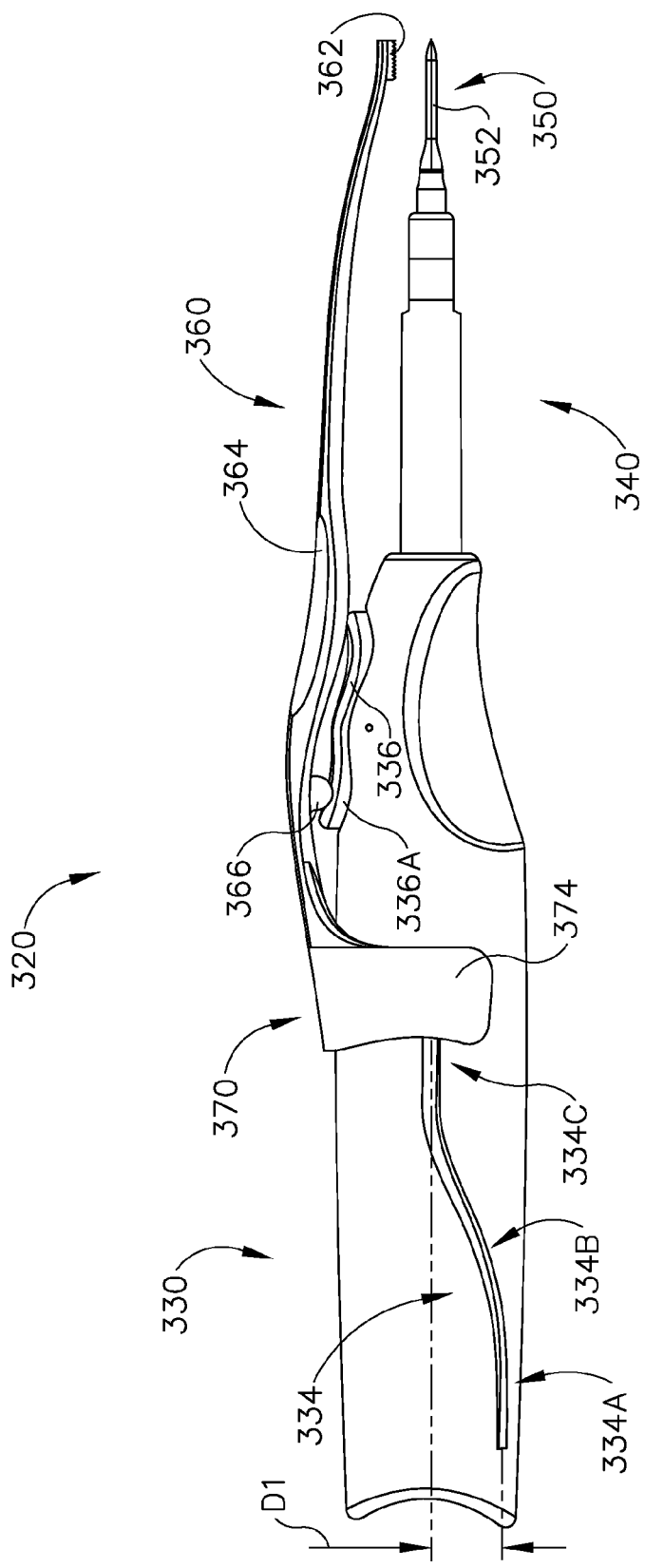
FIG. 11 depicts another side elevational view of the instrument of FIG. 8 with the clamp arm in the distal position.

As best seen in FIGS. 10 and 11, handle assembly (330) comprises a pair of curved tracks (332, 334) formed in opposing sides of an exterior surface of handle assembly (330). As shown in FIG. 10, track (332) comprises a proximal portion (332A) and a distal portion (332C). Proximal portion (332A) and distal portion (332C) are substantially straight and horizontal, such that portions (332A, 332C) each extend along paths that are substantially parallel to the longitudinal axis defined by handle assembly (330). Proximal portion (332A) and distal portion (332C) are, however, separated by a vertical distance (D1), with proximal portion (332A) at a position higher than distal portion (332C). An intermediate portion (332B) connects proximal portion (332A) and distal portion (332C). Intermediate portion (332B) is curved and provides for a vertical transition between proximal portion (332A) and distal portion (332C). As shown in FIG. 11, track (334) comprises a proximal portion (334A) and a distal portion (334C). Proximal portion (334A) and distal portion (334C) are substantially straight and horizontal, such that portions (334A, 334C) each extend along paths that are substantially parallel to the longitudinal axis defined by handle assembly (330). Proximal portion (334A) and distal portion (334C) are, however, separated by vertical distance (D1), with proximal portion (334A) at a position lower than distal portion (334C). An intermediate portion (334B) connects proximal portion (334A) and distal portion (334C). Intermediate portion (334B) is curved and provides for a vertical transition between proximal portion (334A) and distal portion (334C). It should be appreciated that, although they are formed on opposing sides of handle assembly (330), the longitudinal positioning and shapes of tracks (332, 334) correspond to one another. In particular, as best seen in FIGS. 10-11, tracks (332, 334) are mirror images of each other about a horizontal plane (horizontal in the views shown in FIGS. 10-11) that extends along the longitudinal axis of handle assembly (330).

Figure 12:
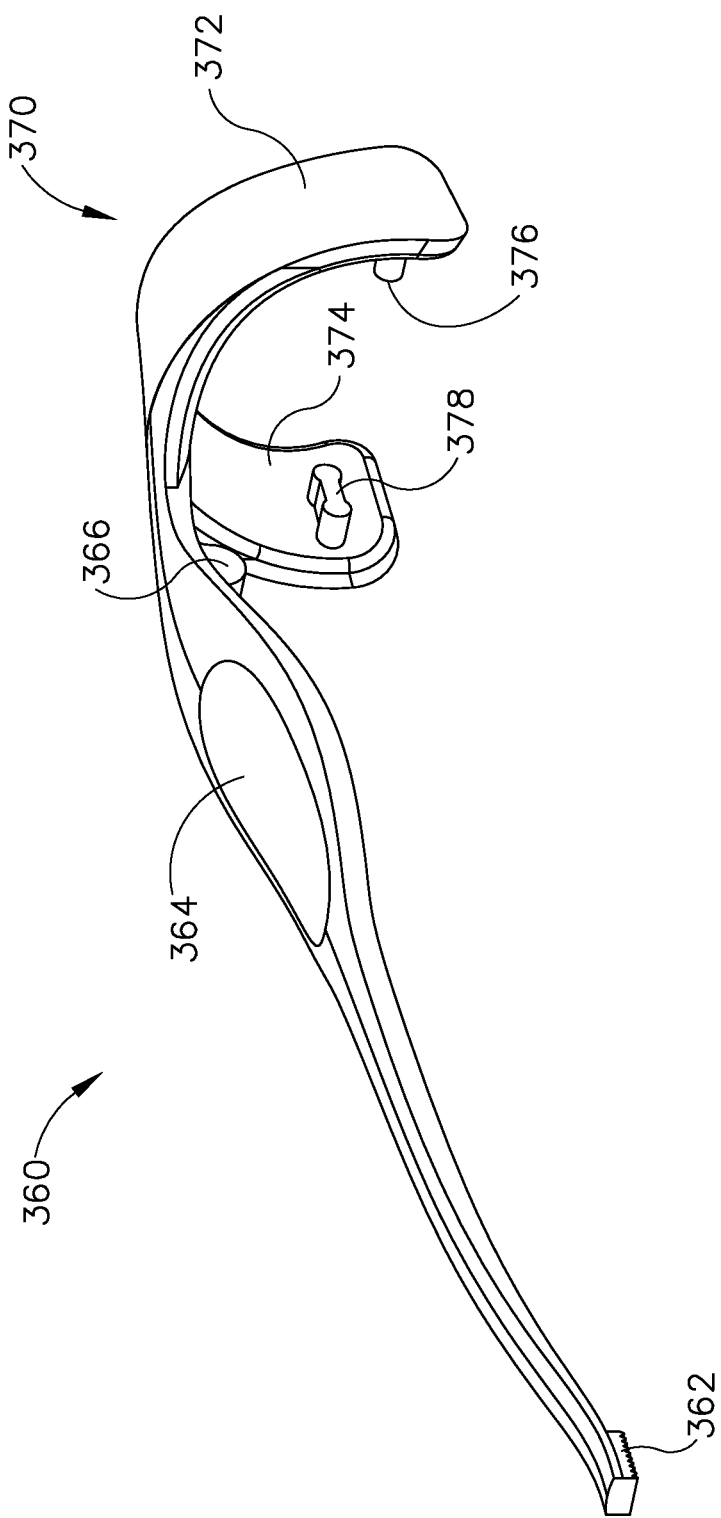
FIG. 12 depicts a perspective view of the clamp arm of FIG. 8.

A distal end of clamp arm (360) comprises a clamp pad (362). In some versions, clamp pad (362) comprises polytetrafluoroethylene (PTFE). Alternatively, clamp pad (362) may comprise any other suitable material(s) as will be apparent to those of ordinary skill in the art in view of the teachings herein. As best seen in FIG. 12, a proximal end of clamp arm (360) comprises a semicircular member (370) having a pair of arcuate limbs (372, 374). Semicircular member (370) comprises a pair of tabs (376, 378) extending inwardly from opposing interior surfaces of limbs (372, 374). Tracks (332, 334) are configured to slidably receive tabs (376, 378) of semicircular member (370) such that clamp arm (360) is operable to slide within tracks (332, 334) between the "inoperative position" (FIGS. 13A and 14A) and the "operative position" (FIGS. 13B and 14B). As will be discussed in more detail below, the corresponding substantially horizontal shapes of proximal portions (332A, 334A) and distal portions (332C, 334C) permit clamp arm (360) to translate longitudinally relative to handle assembly (330); and the curved shapes of intermediate portions (332B, 334B) permit clamp arm (360) to simultaneously translate longitudinally relative to handle assembly (330) and rotate about handle assembly (330). Thus, from the discussion below, it will be appreciated that tracks (332, 334) serve as cam paths and that tabs (376, 378) serve as cam followers, such that tracks (332, 334) and tabs (376, 378) provide for rotation of clamp arm (360) about the longitudinal axis of handle assembly (330) as clamp arm (360) translates relative to the longitudinal axis of the handle assembly (330). In some other versions, tracks (332, 334) are simply straight, such that clamp arm (360) simply translates longitudinally relative to the longitudinal axis of the handle assembly (330) without also rotating about the longitudinal axis of the handle assembly (330).

Figure 13A:
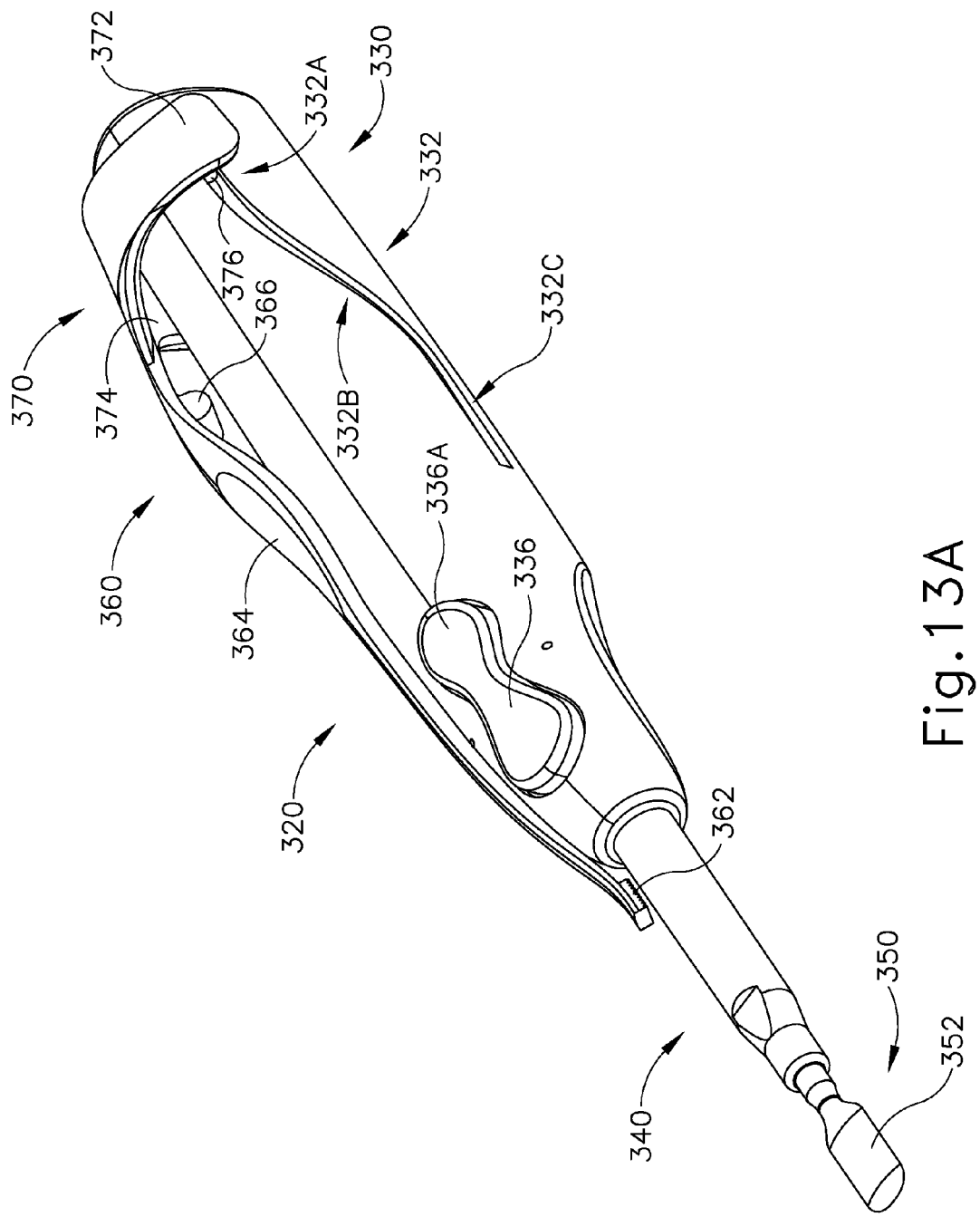
FIG. 13A depicts a perspective view of the instrument of FIG. 8 with the clamp arm in a proximal position.
Figure 13B:
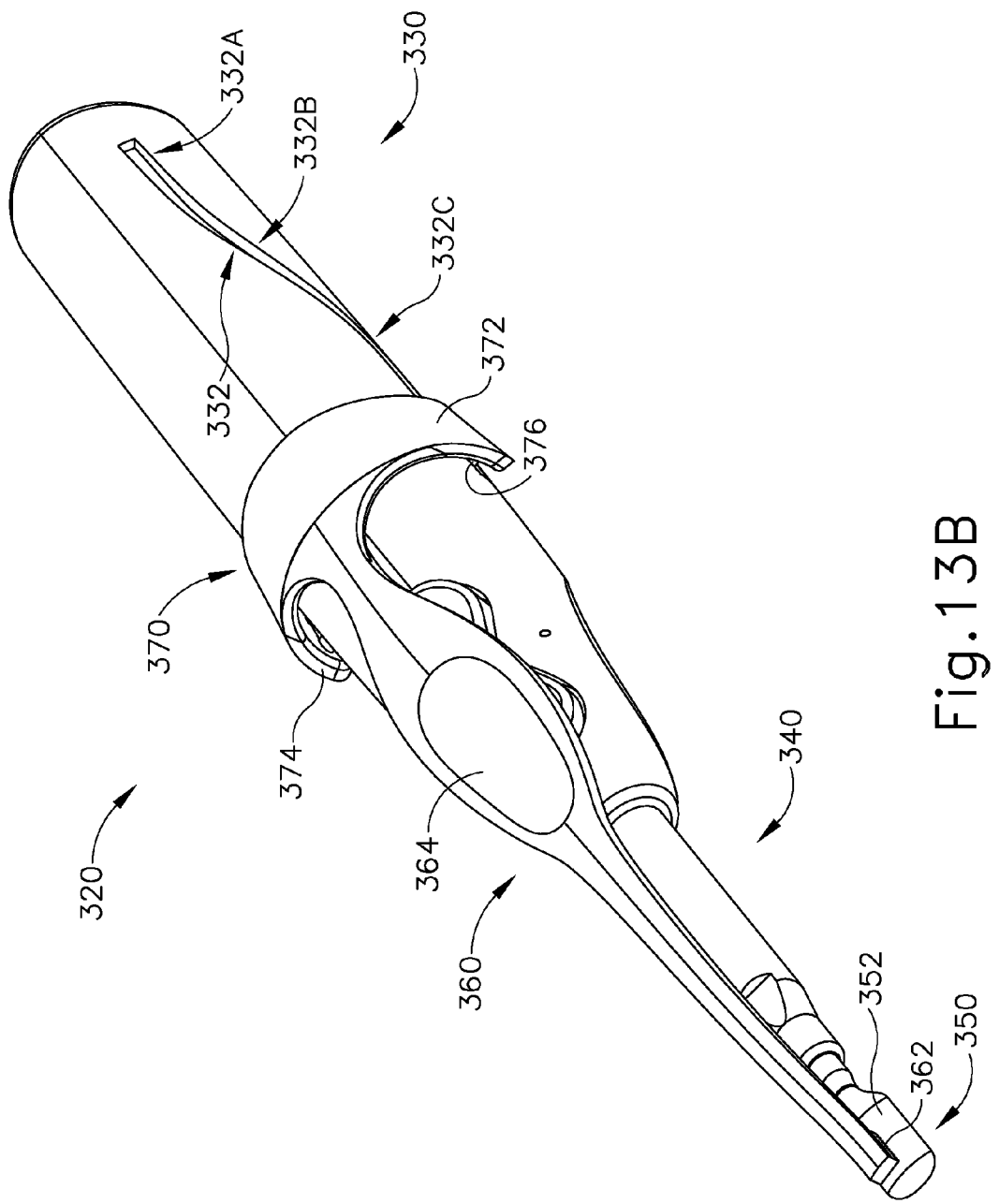
FIG. 13B depicts a perspective view of the instrument of FIG. 8 with the clamp arm longitudinally translated and rotated into the distal position.
Figure 14A:
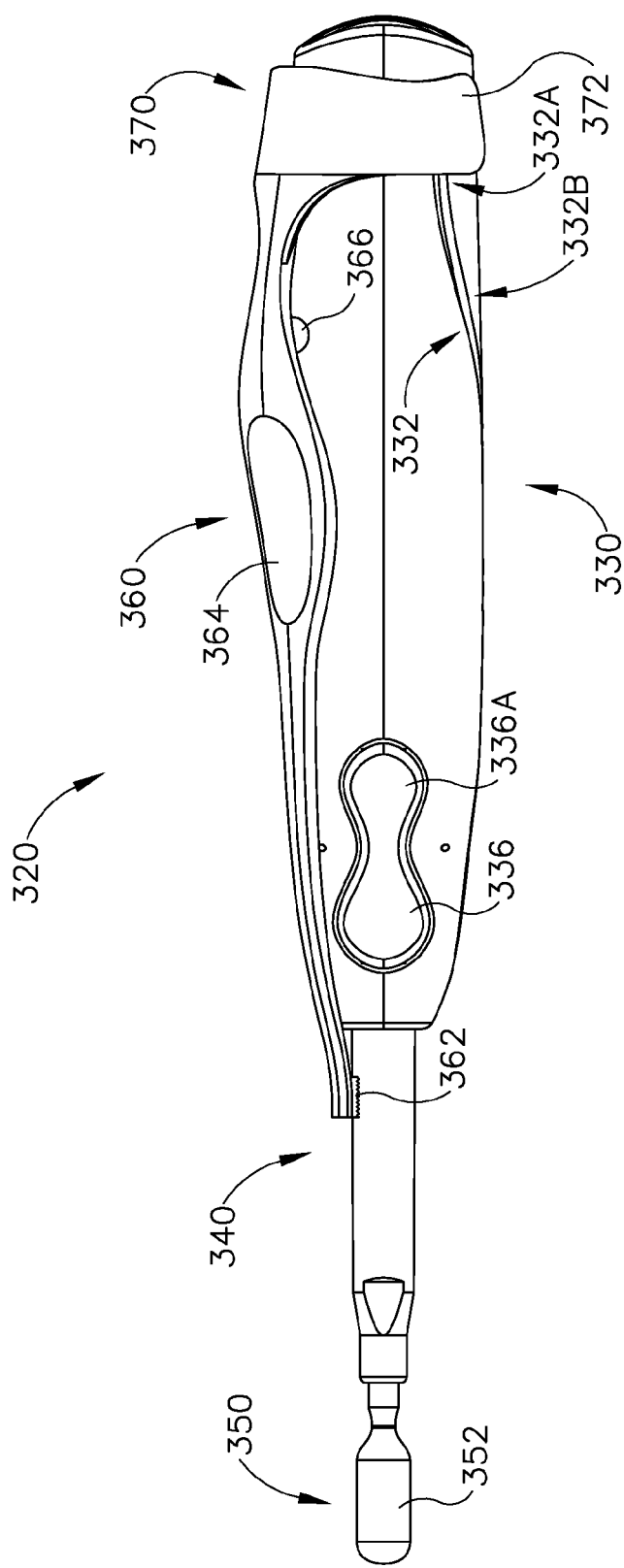
FIG. 14A depicts a top view of the instrument of FIG. 8 with the clamp arm in the proximal position.
Figure 14B:
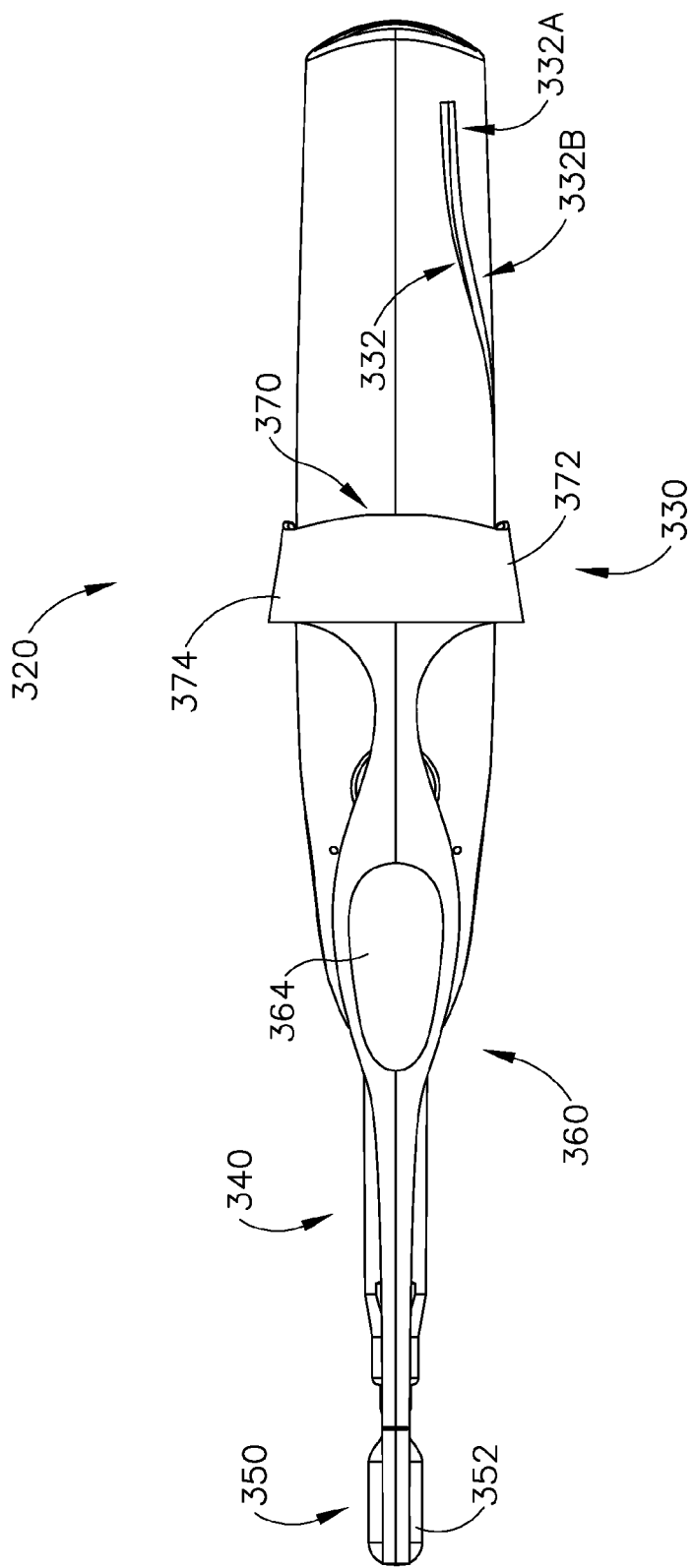
FIG. 14B depicts a top view of the instrument of FIG. 8 with the clamp arm longitudinally translated and rotated into the distal position.

FIGS. 13A and 14A show clamp arm (360) in the "inoperative position." In the "inoperative position," tabs (376, 378) of semicircular member (370) are disposed within proximal portions (332A, 334A) of tracks (332, 334) such that a clamp pad (362) of clamp arm (360) is positioned proximally of end effector (350) and such that clamp arm (360) is in a first rotational position alongside handle assembly (330). In this first rotational position, a pair of buttons (336) is not covered by clamp arm (360). Buttons (336) are thus exposed for direct contact and actuation by an operator's finger. FIGS. 13B and 14B show clamp arm (360) having been translated within tracks (332, 334) into the "operative position." In the "operative position," tabs (376, 378) of semicircular member (370) are disposed within distal portions (332C, 334C) of tracks (332, 334) such that clamp pad (362) of clamp arm (360) is positioned directly above an ultrasonic blade (352) of end effector (350) and such that clamp arm (360) is rotated into a second rotational position atop handle assembly (330) via translation of clamp arm (360) within intermediate portions (332B, 334B). In the present example, clamp arm (360) rotates approximately 90° about the longitudinal axis of handle assembly (330) during the transition from the "inoperative" position to the "operative" position. In other version, clamp arm (360) rotates about longitudinal axis of handle assembly (330) through some other angular range during the transition from the "inoperative" position to the "operative" position.

As best seen in FIGS. 10 and 11, with clamp arm (360) in the "operative position," a vertical gap exists between a bottom surface of clamp pad (362) and ultrasonic blade (352). Tissue may be positioned within this gap. The operator may then force clamp arm (360) to flex downwardly so as to capture the tissue between the bottom surface of clamp pad (362) and blade (352). For instance, the operator may use his or her index finger to force clamp arm (360) to flex downwardly, thereby compressing tissue between clamp pad (362) and ultrasonic blade (352). Clamp arm (360) comprises a post (366) extending from a bottom surface of clamp arm (360). As clamp arm (360) is flexed downwardly, post (366) bears against a button (336A) of pair of buttons (336) of instrument (320), thereby depressing button (336A) and activating blade (352) as discussed above with reference to instrument (120). It should be appreciated that depression of button (336A) may correlate to generator (12) producing a "max" power setting, a "min" power setting, or any other power setting. Thus, it should be understood that forcing clamp arm (360) to flex downwardly will simultaneously activate blade (352) and compress tissue between the bottom surface of clamp pad (363) and blade (352).

As with blade (252) discussed above, blade (352) of the present example comprises a broad top surface so as to provide a broad surface for compression of tissue between blade (352) and clamp pad (362). The side surfaces of blade (352), on the other hand, are relatively thin such that the side surfaces of blade (352) may be used for cutting tissue without the assistance of clamp pad (362). It should be understood, however, that blade (352) may have any other suitable shape, including but not limited to any other ultrasonic blade shapes shown or described herein and/or shown or described in any of the references cited herein.

Clamp arm (360) comprises a finger pad (364). Finger pad (364) may provide for comfort and/or non-visual positioning of the operator's finger along clamp arm (360). For instance, finger pad (364) may comprise a recessed or raised portion or a material which contrasts with a material of clamp arm (360) such that finger pad (364) may be tactilely sensed by the operator. Finger pad (364) may also include ridges, knurling, elastomeric material, and/or other features that prevent the operator's finger from sliding along clamp arm (360) as the operator presses clamp arm (360) toward handle assembly (330).

In an exemplary use, the operator may readily transition instrument (320) between two modes of operation by translating and rotating clamp arm (360) between the operative position and the inoperative position. For instance, the operator may perform at least part of a surgical procedure with clamp arm (360) in the inoperative position, such that the operator uses ultrasonic blade (352) like a scalpel. The operator may thus grip and use instrument (320) in a manner similar to a grip and use of instrument (120) when clamp arm (360) is in the inoperative position. Within the same surgical procedure (or in a different surgical procedure), the operator may translate and rotate clamp arm (360) to the operative position, then compress tissue between clamp pad (362) and ultrasonic blade (352) as described above. The operator may transition between these two modes as many times as desired within a given surgical procedure. Other suitable ways in which instrument (320) may be used will be apparent to those of ordinary skill in the art in view of the teachings herein.

C. Exemplary Ultrasonic Forceps with Slot-Guided Clamp Arm

Figure 15A:
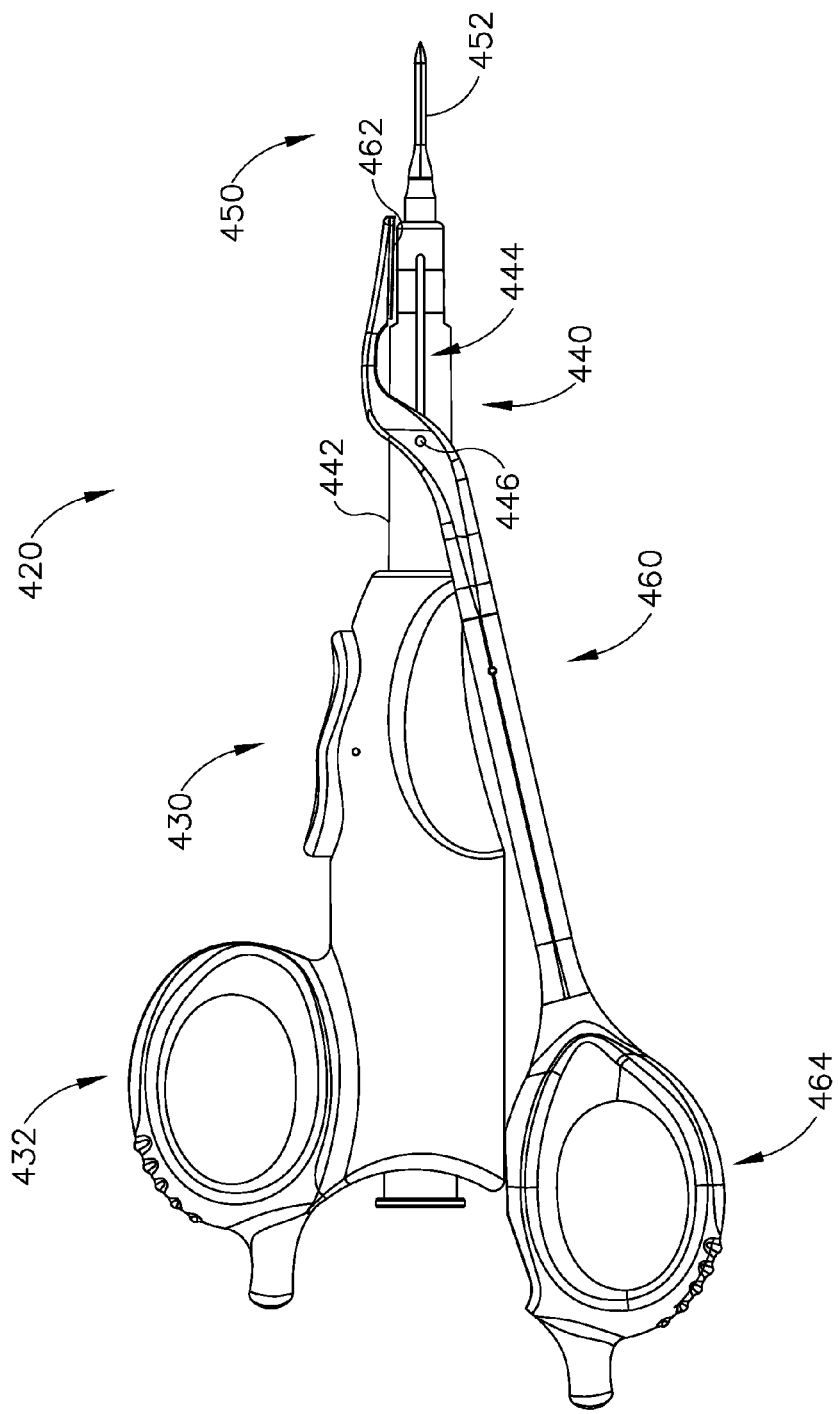
FIG. 15A depicts a side elevational view of yet another exemplary alternative surgical instrument having a slidable clamp arm in a proximal position.
Figure 15B:
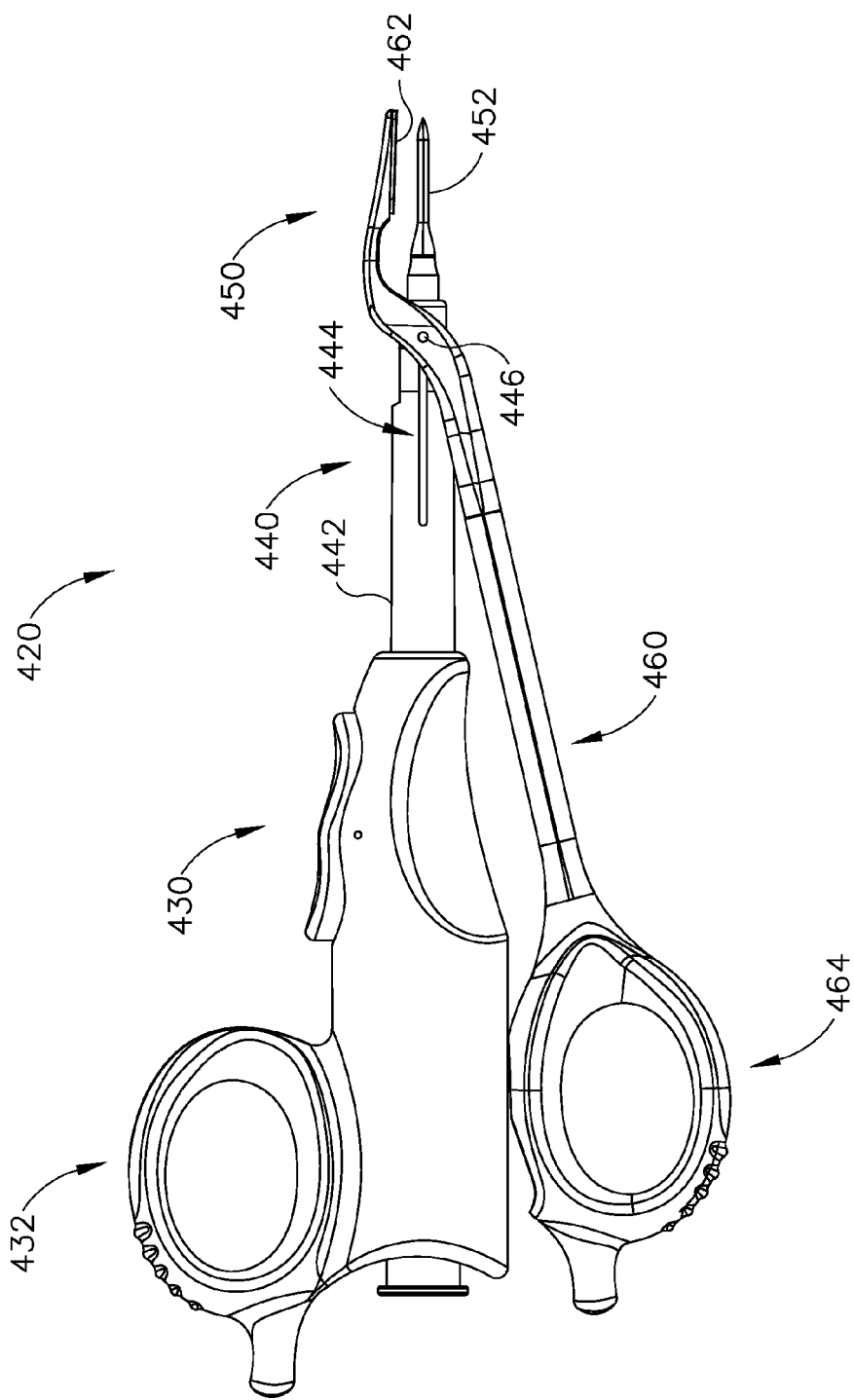
FIG. 15B depicts a side elevational view of the instrument of FIG. 15A with the clamp arm longitudinally translated into a distal position, and with the clamp arm pivoted to a partially closed position.
Figure 15C:
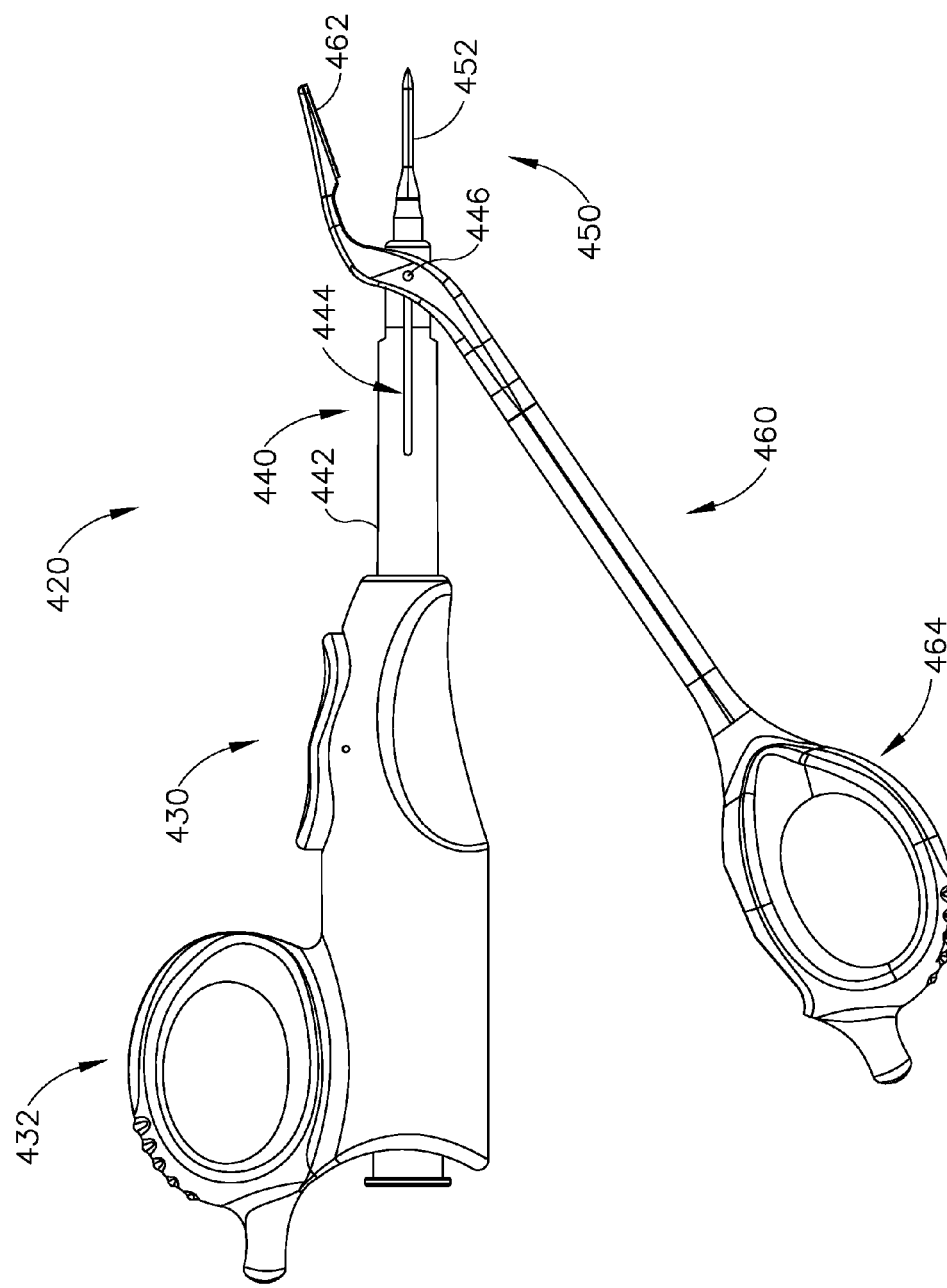
FIG. 15C depicts a side elevational view of the instrument of FIG. 15A with the clamp arm longitudinally translated to the distal position, and with the clamp arm further pivoted to an open position.

FIGS. 15A-15C illustrate yet another exemplary alternative ultrasonic surgical instrument (420) configured to be used as a scalpel. Instrument (420) may be used in conjunction with ultrasonic surgical system (10) which includes ultrasonic transducer (26) coupled with ultrasonic generator (12) via cable (14). Instrument (420) of this example comprises a handle assembly (430), a shaft assembly (440), and an end effector (450). Instrument (420) is configured to operate substantially similar to instrument (120) discussed above except for the differences discussed below. In particular, instrument (420) may be used to cut tissue and seal or weld tissue (e.g., a blood vessel, etc.) substantially simultaneously. Unlike instrument (120) discussed above, however, instrument (420) of the present example comprises a retractable clamp arm (460). As will be discussed in more detail below, clamp arm (460) is configured to be translated longitudinally between an "inoperative position" (FIG. 15A), when a user does not wish to use clamp arm (460), and an "operative position" (FIGS. 15B-15C), when the user desires to use clamp arm (460). Furthermore, unlike instrument (120) discussed above, handle assembly (430) of the present example comprises a finger grip (432) which, as will be discussed in more detail below, allows a user to use instrument (420) as he or she would a pair of surgical forceps with a scissor grip.

Clamp arm (460) comprises a clamp pad (462) at a distal end and a thumb grip (464) at a proximal end. In some versions, clamp pad (462) comprises polytetrafluoroethylene (PTFE). Alternatively, clamp pad (462) may comprise any other suitable material(s) as will be apparent to those of ordinary skill in the art in view of the teachings herein. Shaft assembly (440) comprises a pair of elongate slots (444) formed in opposing exterior side surfaces of an outer sheath (442) of shaft assembly (440). Slots (444) each extend along respective paths that are parallel to the longitudinal axis defined by shaft assembly (440). Clamp arm (460) is slidably and rotatably coupled within slots (444) via a pair of pins (446) such that clamp arm (460) is operable to translate longitudinally within slots (444) between the "inoperative position" (FIG. 15A) and the "operative position" shown (FIGS. 15B and 15C). Clamp arm (460) is further operable to rotate within slots (444) such that clamp pad (462) may be rotated toward and away from shaft assembly (440) and end effector (450), between the position shown in FIG. 15B and the position shown in FIG. 15C.

FIG. 15A shows clamp arm (460) in the "inoperative position." In the "inoperative position," pins (446) of clamp arm (460) are disposed within slots (444) at a proximal longitudinal position such that clamp pad (462) is positioned proximally of an ultrasonic blade (452) of end effector (450). Also in the "inoperative position," clamp arm (460) is in a first rotational position. In the first rotational position, clamp pad (462) is disposed substantially adjacent to outer sheath (442) of shaft assembly (440). It should be understood that instrument (420) may include features configured to prevent rotation of clamp arm (460) when in the "inoperative position" to thereby cause clamp arm (460) to remain in the first rotational position when in the "inoperative position." FIG. 15B shows clamp arm (460) having been translated distally within slots (444) into the "operative position." In the "operative position," pins (446) of clamp arm (460) are disposed within slots (444) at a distal longitudinal position. Also in the "operative position," clamp arm (460) may be rotated between the first rotational position (FIG. 15B) and a second rotational position (FIG. 15C) so as to rotate clamp pad (462) toward and away from blade (452) of end effector (450). It should therefore be understood that with clamp arm (460) in the "operative position," the user may use instrument (420) as he or she would a pair of surgical forceps by rotating clamp arm (460) between the first rotational position and the second rotational position using grips (432, 464) to thereby capture and compress tissue between the bottom surface of clamp pad (462) and blade (452) of end effector (450). In some versions, when clamp arm (460) is in the "operative position," instrument (420) is constructed and operable in accordance with at least some of the teachings of U.S. patent application Ser. No. 14/031,665, entitled "Alignment Features for Ultrasonic Surgical Instrument," filed Sep. 19, 2013, now U.S. Pub. No. 2015/0080925, published Mar. 19, 2015, the disclosure of which is incorporated by reference herein; and/or U.S. Pub. No. 2007/0191713, entitled "Ultrasonic Device for Cutting and Coagulating," published Aug. 16, 2007, the disclosure of which is incorporated by reference herein.

As with blades (252, 352) discussed above, blade (452) of the present example comprises a broad top surface so as to provide a broad surface for compression of tissue between blade (452) and clamp pad (462). The side surfaces of blade (452), on the other hand, are relatively thin such that the side surfaces of blade (452) may be used for cutting tissue without the assistance of clamp pad (462). It should be understood, however, that blade (452) may have any other suitable shape, including but not limited to any other ultrasonic blade shapes shown or described herein and/or shown or described in any of the references cited herein.

In an exemplary use, the operator may readily transition instrument (420) between two modes of operation by translating clamp arm (460) between the operative position and the inoperative position. For instance, the operator may perform at least part of a surgical procedure with clamp arm (460) in the inoperative position, such that the operator uses ultrasonic blade (452) like a scalpel. The operator may thus grip and use instrument (420) in a manner similar to a grip and use of instrument (120) when clamp arm (460) is in the inoperative position. Within the same surgical procedure (or in a different surgical procedure), the operator may translate clamp arm (460) to the operative position, then compress tissue between clamp pad (462) and ultrasonic blade (452) as described above, holding instrument (420) in a scissor grip. The operator may transition between these two modes as many times as desired within a given surgical procedure. Other suitable ways in which instrument (420) may be used will be apparent to those of ordinary skill in the art in view of the teachings herein.

D. Exemplary Ultrasonic Forceps with Slot-Guided Clamp Arm and Position-Guiding Slot FIGS. 16-20E illustrate yet another exemplary alternative ultrasonic surgical instrument (520) configured to be used as a scalpel. Instrument (520) may be used in conjunction with ultrasonic surgical system (10) which includes ultrasonic transducer (26) coupled with ultrasonic generator (12) via cable (14). Instrument (520) of this example comprises a handle assembly (530), a shaft assembly (540), and an end effector (550). Instrument (520) is configured to operate substantially similar to instrument (120) discussed above except for the differences discussed below. In particular, instrument (520) may be used to cut tissue and seal or weld tissue (e.g., a blood vessel, etc.) substantially simultaneously. Unlike instrument (120) discussed above, however, instrument (520) of the present example comprises a retractable clamp arm (560). As will be discussed in more detail below, clamp arm (560) is configured to be translated between an "inoperative position" (FIG. 19A), when a user does not wish to use clamp arm (560), and an "operative position" (FIGS. 19D-19E) when the user desires to use clamp arm (560). Furthermore, unlike instrument (120) discussed above, handle assembly (530) of the present example comprises a finger grip (532) which, as will be discussed in more detail below, allows a user to use instrument (520) as he or she would a pair of surgical forceps with a scissor grip.

Figure 16:
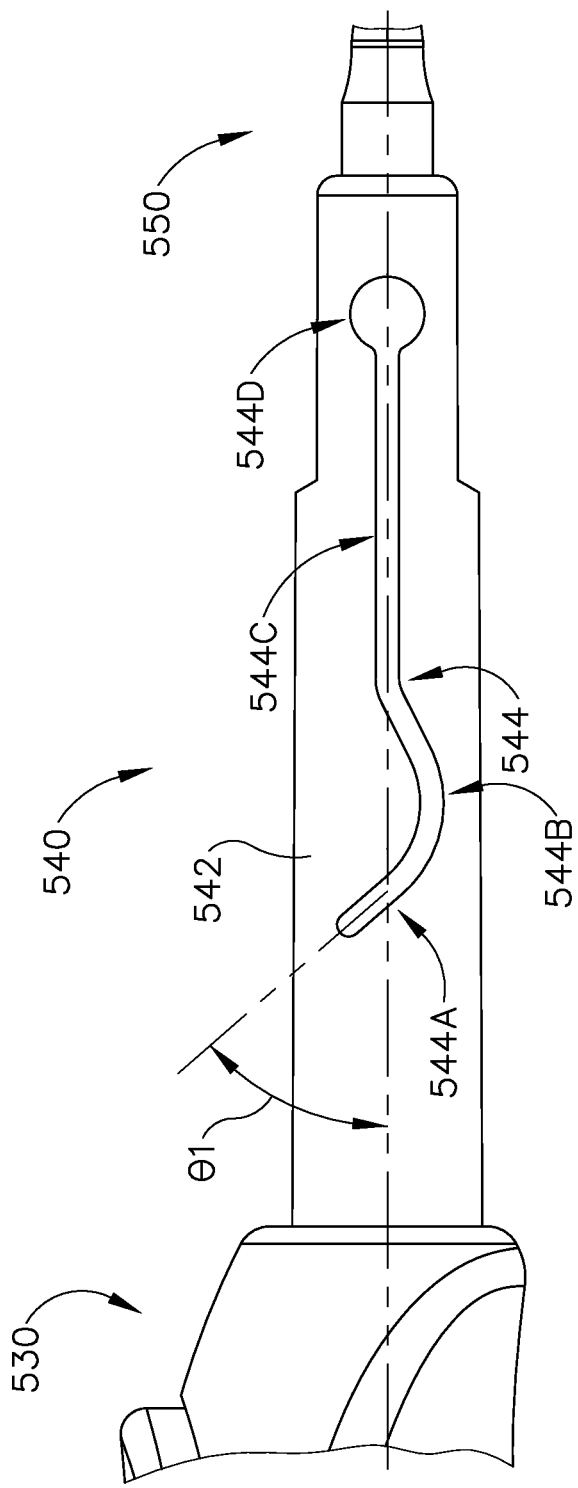
FIG. 16 depicts a side elevational view of a shaft assembly and slot of yet another exemplary alternative surgical instrument.

Shaft assembly (540) defines a longitudinal axis (LA1). Shaft assembly (540) comprises a pair of slots (544) formed in opposing exterior side surfaces of an outer sheath (542) of shaft assembly (540). Slots (544) each comprise a substantially straight proximal portion (544A) oriented obliquely relative to longitudinal axis (LA1) of shaft assembly (540). In particular, each substantially straight proximal portion (544A) is oriented at an angle ($\theta$1) relative to longitudinal axis (LA1) of shaft assembly (540). As best seen in FIG. 16, slots (544) each further comprise a substantially straight-horizontal intermediate portion (544C) and a bowed intermediate portion (544B) which provides for transition between the angular orientation of substantially straight proximal portion (544A) and the horizontal orientation of substantially horizontal intermediate portion (544C). Slots (544) each further comprise a distal circular portion (544D) which, as will be discussed in more detail below, allows for rotation of clamp arm (560).

Shaft assembly (540) is disposed within an opening (566) of clamp arm (560). Clamp arm (560) comprises a clamp pad (562) at a distal end and a thumb grip (564) at a proximal end. In some versions, clamp pad (562) comprises polytetrafluoroethylene (PTFE). Alternatively, clamp pad (562) may comprise any other suitable material(s) as will be apparent to those of ordinary skill in the art in view of the teachings herein. Clamp arm (560) is slidably and rotatably coupled within slots (544) via a pair of tabs (546) such that clamp arm (560) is operable to translate within slots (544) between the "inoperative position" (FIG. 19A) and the "operative position" (FIG. 19E). Tabs (546) of the present example each have an elongated pill-shaped cross-section.

Figure 17:
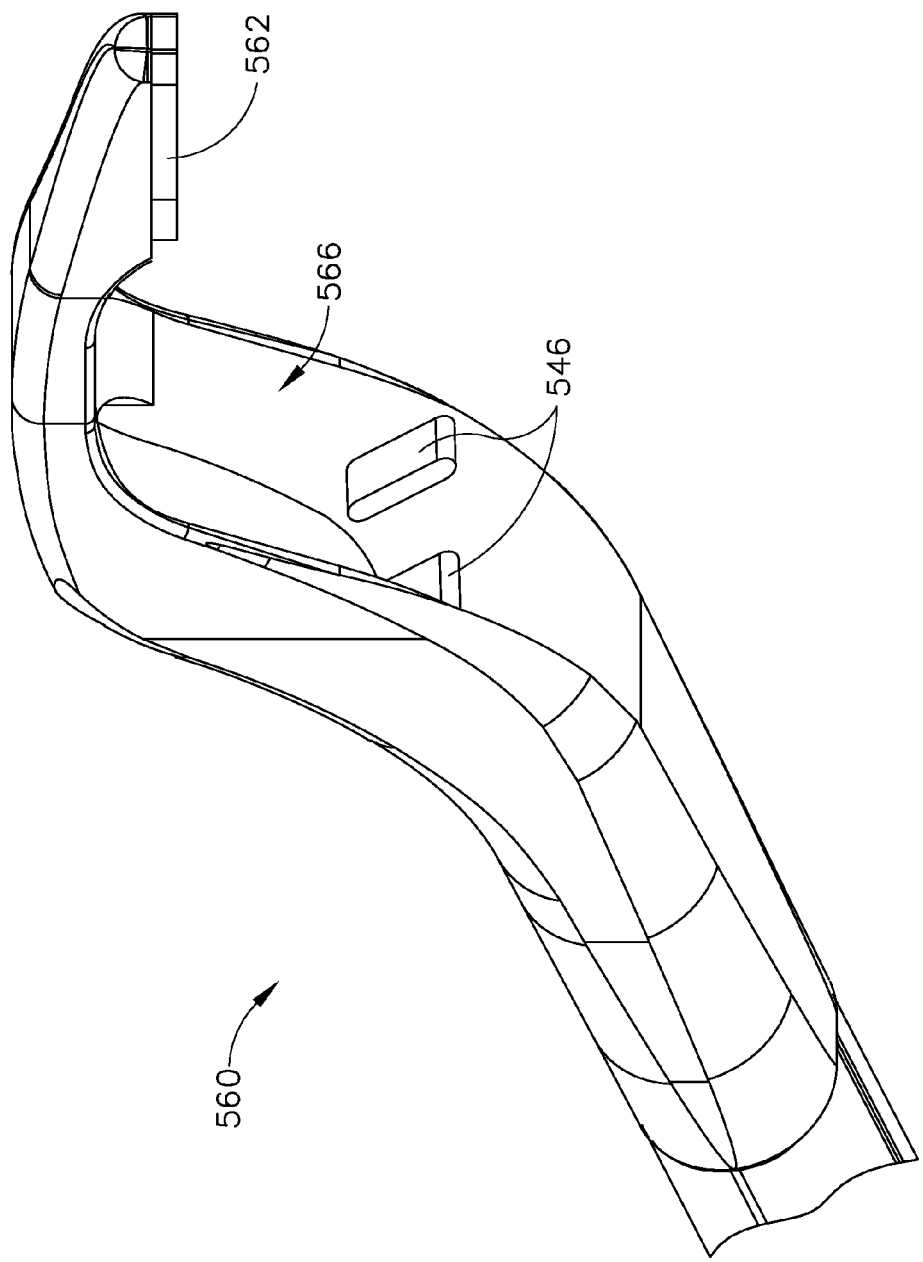
FIG. 17 depicts a perspective view of an exemplary clamp arm.
Figure 18:
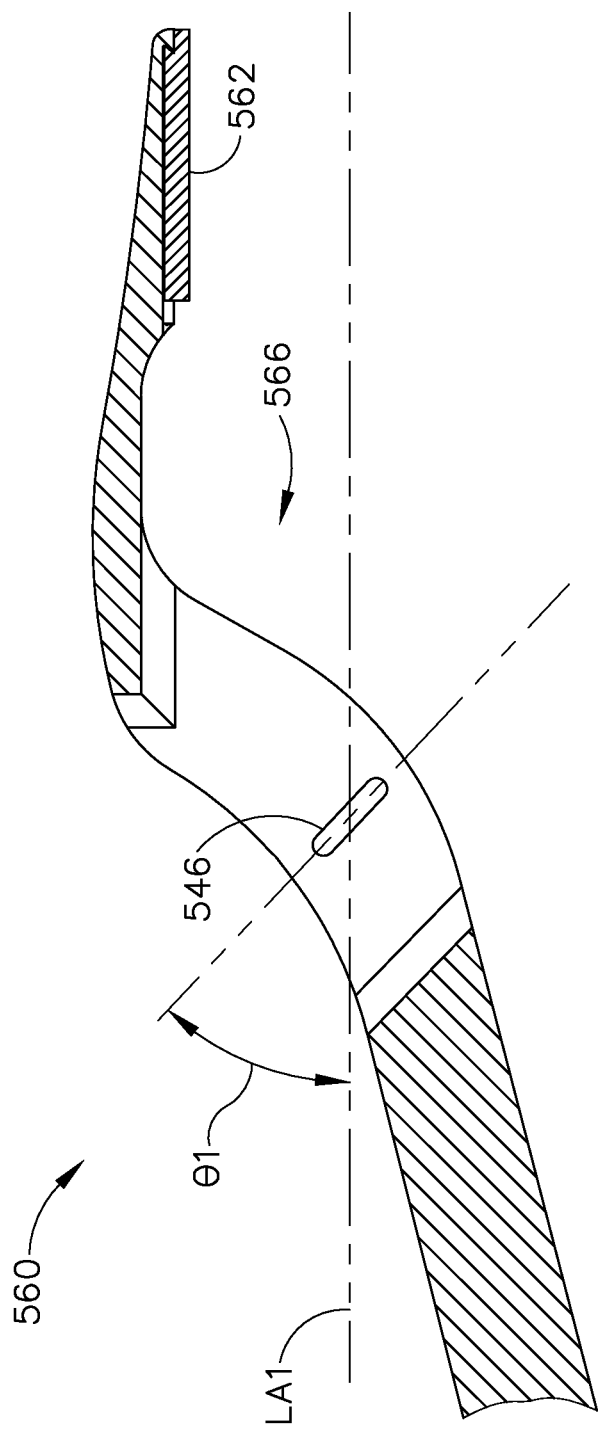
FIG. 18 depicts a cross-sectional side elevational view of the clamp arm of FIG. 17.

As best seen in FIG. 17, tabs (546) extend inwardly from an interior surface of opening (566). As best seen in FIG. 18, tabs (546) are oriented obliquely relative to longitudinal axis (LA1) of shaft assembly (540). In particular, tabs (546) are oriented at the same angle ($\theta$1) relative to longitudinal axis (LA1) of shaft assembly (540). The length of tabs (546) is substantially identical to the diameter of circular portion of slots (544). Thus, tabs (546) are operable to rotate within distal circular portion (544D) of slots (544) such that clamp pad (562) may be freely rotated toward and away from shaft assembly (540) and end effector (550). As will be discussed in more detail below, however, the elongate pill-shape of tabs (546) prevents rotation of clamp arm (560) within portions (544A, 544B, 544C) of slots (544) except for rotation that is driven by the curved shape of portions (544A, 544B, 544C) as clamp arm (560) is translated therein.

FIGS. 19A and 20A show clamp arm (560) in the "inoperative position." In the "inoperative position," tabs (546) of clamp arm (560) are disposed within substantially straight proximal portion (544A) of slots (544) such that clamp pad (562) is positioned proximally of an ultrasonic blade (552) of end effector (550). Also in the "inoperative position," clamp arm (560) is in a first rotational position. In the first rotational position, clamp pad (562) is disposed substantially adjacent to outer sheath (542) of shaft assembly (540) and parallel to longitudinal axis (LA1) of shaft assembly (540). FIGS. 19B and 20B show clamp arm (560) translated distally into a first intermediate position. In the first intermediate position, tabs (546) of clamp arm (560) are disposed within bowed intermediate portion (544B) of slots (544) such that clamp pad (562) remains positioned proximally of blade (552) of end effector (550). Also in the first intermediate position, clamp arm (560) is rotated into a second rotational position due to the shape of bowed intermediate portion (544B). In the second rotational position, clamp pad (562) is oriented obliquely to longitudinal axis (LA1) of shaft assembly (540) such that clamp arm (560) is in an open position. FIGS. 19C and 20C show clamp arm (560) translated further distally into a second intermediate position. In the second intermediate position, tabs (546) of clamp arm (560) are disposed within horizontal intermediate portion (544C) of slots (544) such that clamp pad (562) remains positioned proximally of blade (552) of end effector (550). Also in the second intermediate position, clamp arm (560) remains in the second rotational position due to the shape of horizontal intermediate portion (544C). As discussed above, in the second rotational position, clamp pad (562) is oriented obliquely to longitudinal axis (LA1) of shaft assembly (540) such that clamp arm (560) is in the open position.

FIGS. 19D and 20D show clamp arm (560) translated further distally into the "operative position." In the "operative position," tabs (546) of clamp arm (560) are disposed within distal circular portion (544D) of slots (544). Also in the "inoperative position," tabs (546) may be freely rotated within distal circular portion (544D), allowing clamp arm (560) to be pivoted toward and away from blade (552) of end effector (550) between the open position (FIG. 19D) and a closed position (FIG. 19E). It should therefore be understood that with clamp arm (560) in the "operative position," the user may use instrument (520) as he or she would a pair of surgical forceps by rotating clamp arm (560) between the open position and the closed position using grips (532, 564) to thereby capture and compress tissue between the bottom surface of clamp pad (562) and an ultrasonic blade (552) of end effector (550). In some versions, when clamp arm (560) is in the "operative position," instrument (520) is constructed and operable in accordance with at least some of the teachings of U.S. patent application Ser. No. 14/031,665, entitled "Alignment Features for Ultrasonic Surgical Instrument," filed Sep. 19, 2013, now U.S. Pub. No. 2015/0080925, published Mar. 19, 2015, the disclosure of which is incorporated by reference herein; and/or U.S. Pub. No. 2007/0191713, entitled "Ultrasonic Device for Cutting and Coagulating," published Aug. 16, 2007, the disclosure of which is incorporated by reference herein.

As with blades (252, 352, 452) discussed above, blade (552) of the present example comprises a broad top surface so as to provide a broad surface for compression of tissue between blade (552) and clamp pad (562). The side surfaces of blade (552), on the other hand, are relatively thin such that the side surfaces of blade (552) may be used for cutting tissue without the assistance of clamp pad (562). It should be understood, however, that blade (552) may have any other suitable shape, including but not limited to any other ultrasonic blade shapes shown or described herein and/or shown or described in any of the references cited herein.

In an exemplary use, the operator may readily transition instrument (520) between two modes of operation by translating clamp arm (560) between the operative position and the inoperative position. For instance, the operator may perform at least part of a surgical procedure with clamp arm (560) in the inoperative position, such that the operator uses ultrasonic blade (552) like a scalpel. The operator may thus grip and use instrument (520) in a manner similar to a grip and use of instrument (120) when clamp arm (560) is in the inoperative position. Within the same surgical procedure (or in a different surgical procedure), the operator may translate clamp arm (560) to the operative position, then compress tissue between clamp pad (562) and ultrasonic blade (552) as described above, holding instrument (520) in a scissor grip. The operator may transition between these two modes as many times as desired within a given surgical procedure. Other suitable ways in which instrument (520) may be used will be apparent to those of ordinary skill in the art in view of the teachings herein.

E. Exemplary Ultrasonic Scalpel with Slidable-Flexible Clamp Arm

Figure 21A:
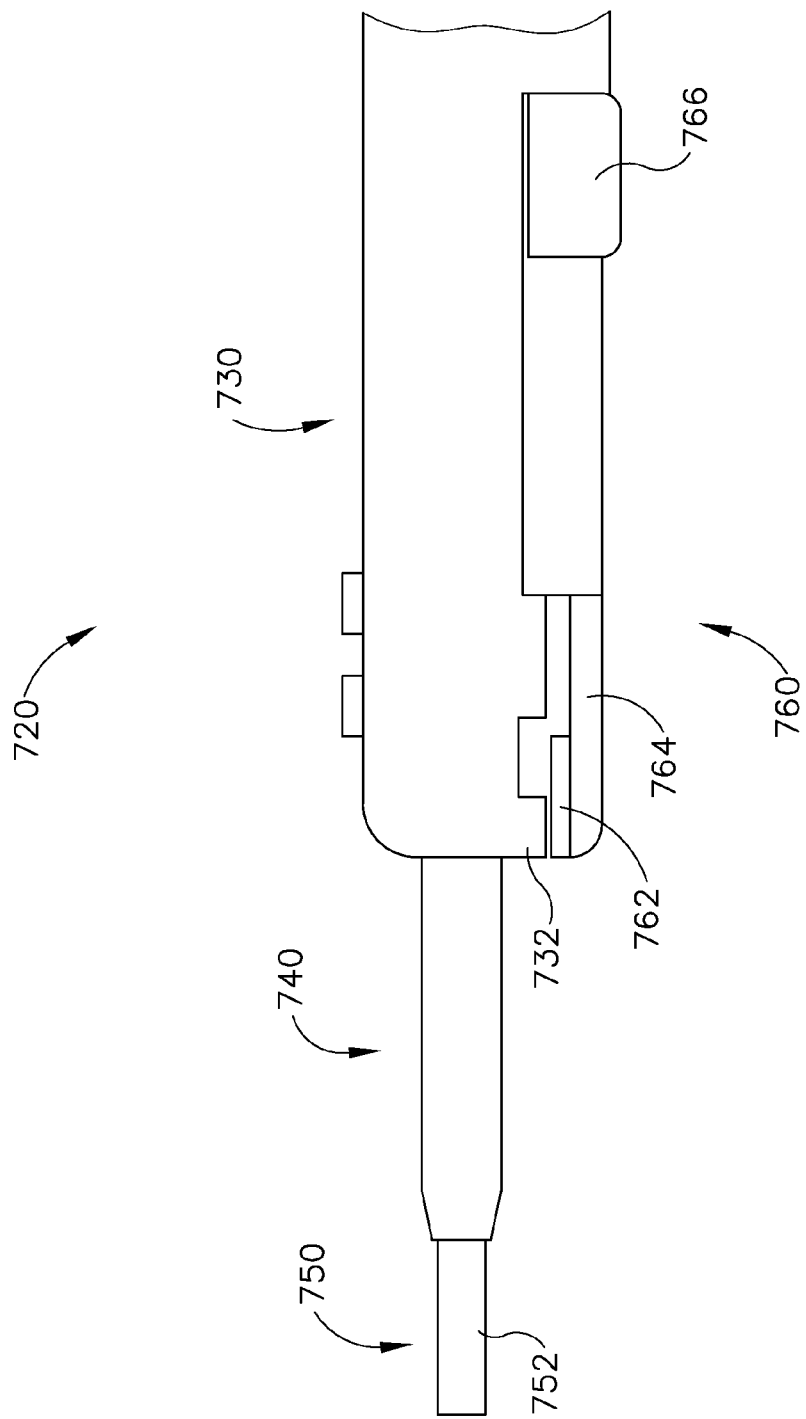
FIG. 21A depicts a side elevational view of a distal end of yet another exemplary alternative surgical instrument having a slidable clamp arm in a proximal position.
Figure 21D:
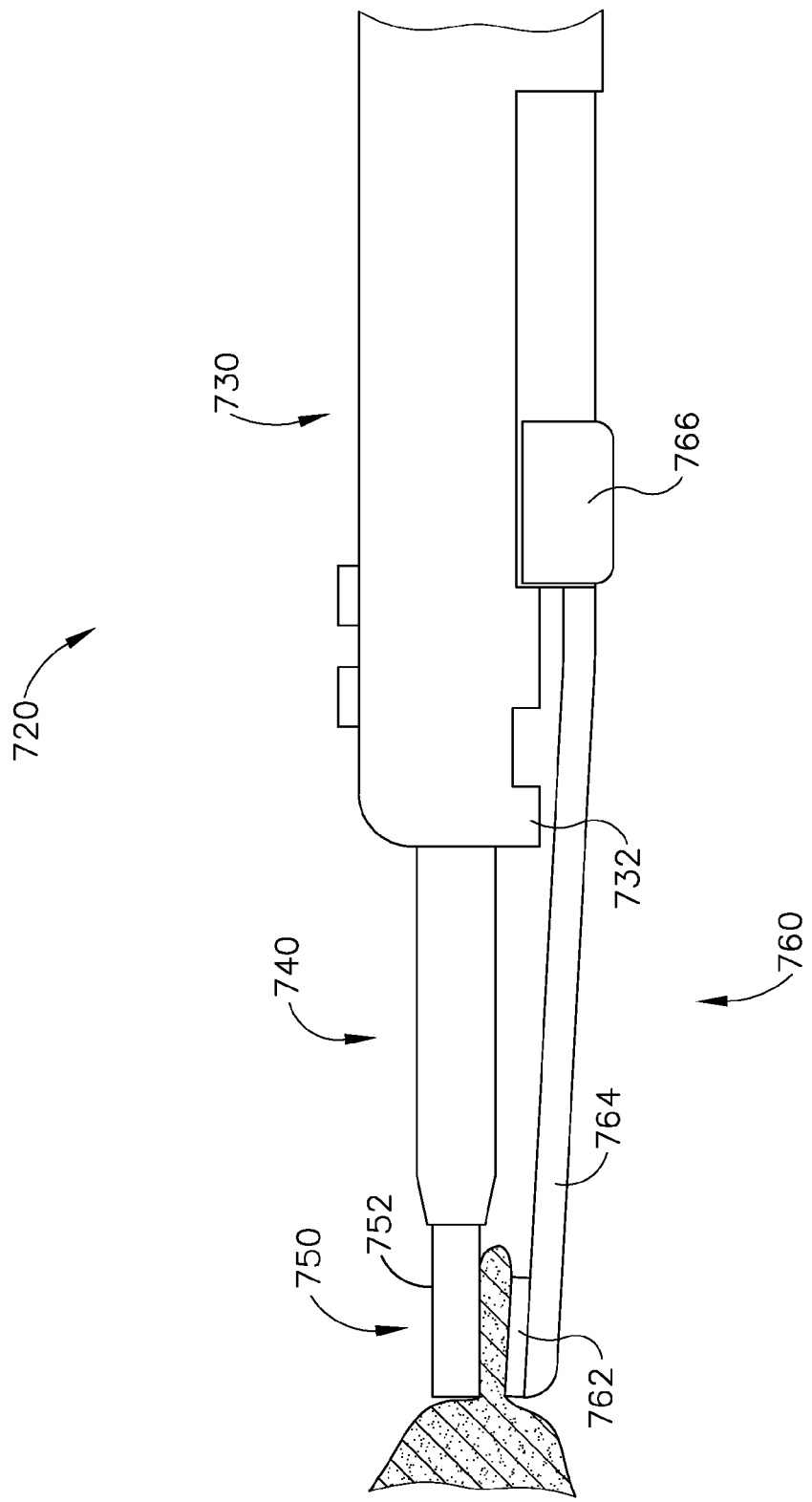
FIG. 21D depicts a side elevational view of the distal end of the instrument of FIG. 21A with the clamp arm in the distal position and flexed into a closed position.
Figure 22:
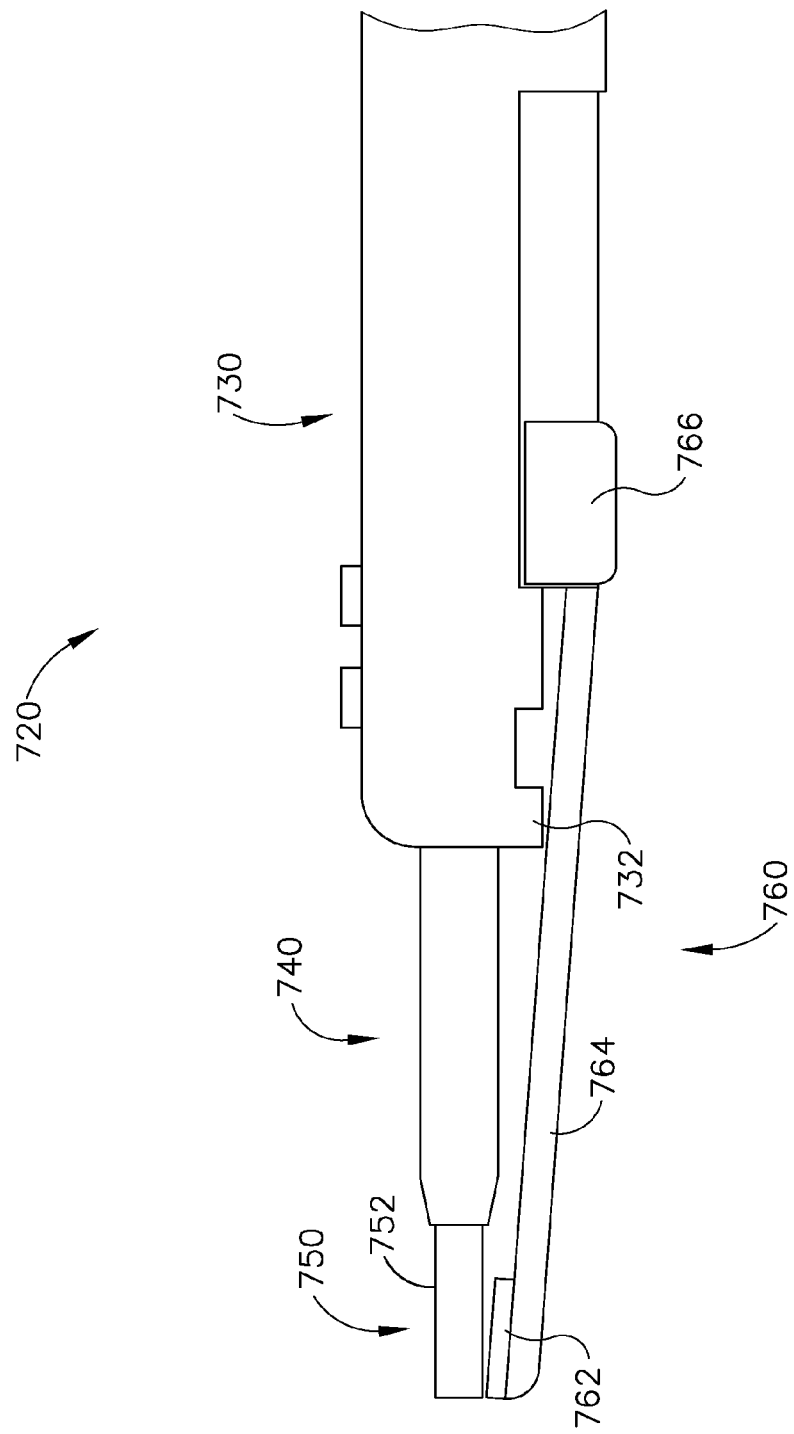
FIG. 22 depicts a side elevational view of the distal end of the instrument of FIG. 21A with the clamp arm in the distal position and flexed into a completely closed position.

FIGS. 21A-22 illustrate yet another exemplary alternative ultrasonic surgical instrument (720) configured to be used as a scalpel. Instrument (720) may be used in conjunction with ultrasonic surgical system (10) which includes ultrasonic transducer (26) coupled with ultrasonic generator (12) via cable (14). Instrument (720) of this example comprises a handle assembly (730), a shaft assembly (740), and an end effector (750). Instrument (720) is configured to operate substantially similar to instrument (120) discussed above except for the differences discussed below. In particular, instrument (720) may be used to cut tissue and seal or weld tissue (e.g., a blood vessel, etc.) substantially simultaneously. Unlike instrument (120) discussed above, however, instrument (720) of the present example comprises a retractable clamp arm (760). As will be discussed in more detail below, clamp arm (760) is configured to slide between an "inoperative position" (FIG. 21A) when a user does not wish to use clamp arm (760) and an "operative position" (FIGS. 21B-22) when the user desires to use clamp arm (760).

Clamp arm (760) comprises a flexible rod (764), a clamp pad (762), and an slider actuator (766). Flexible rod (764) is resiliently biased to assume a substantially straight-horizontal position as shown in FIGS. 21A and 21B. Flexible rod (764) is slidably disposed within a distal portion of handle assembly (730) and extends from handle assembly (730) such that a distal portion of clamp arm (760) is exposed. Clamp pad (762) is secured to a top surface of a distal end of flexible rod (764). In some versions, clamp pad (762) comprises polytetrafluoroethylene (PTFE). Alternatively, clamp pad (762) may comprise any other suitable material(s) as will be apparent to those of ordinary skill in the art in view of the teachings herein. Slider actuator (766) is coupled to a proximal end of flexible rod (764) and is exposed relative to handle assembly (730) such that a user may engage and cause translation of slider actuator (766) relative to handle assembly (730) to thereby cause concurrent translation of clamp arm (760) relative to handle assembly (730).

FIG. 21A shows clamp arm (760) in the "inoperative position." In the "inoperative position," clamp arm (760) is substantially disposed within handle assembly (730) such that only the distal portion of handle assembly (730) extends from a distal end of handle assembly (730) and such that the distal end of clamp arm (760) is adjacent with the distal end of handle assembly (730). Also in the "inoperative position," flexible rod (764) of clamp arm (760) is in the substantially horizontal position. FIG. 21B shows clamp arm (760) translated distally via slider actuator (766) into the "operative position." In the "operative position," clamp arm (760) is substantially exposed relative to handle assembly (730) such that a substantial portion of clamp arm (760) extends from a distal end of handle assembly (730) and a clamp pad (762) of clamp arm (760) is positioned directly below an ultrasonic blade (752) of end effector (750). Also in the "operative position," flexible rod (764) of clamp arm (760) may be flexed downwardly (FIG. 21C) and/or upwardly (FIG. 21D) but is resiliently biased to assume the substantially straight, horizontal position as shown in FIGS. 21A and 21B. Handle assembly (730) comprises a projection (732) extending downwardly from a distal end of handle assembly (730). Projection (732) is configured to engage flexible rod (764) of clamp arm (760) as clamp arm (760) is flexed upwardly to thereby limit the amount by which clamp pad (760) may be flexed upwardly. For instance, clamp arm (760) may be limited from flexing upwardly so as to prevent contact between clamp pad (762) and blade (752) as shown in FIG. 22. Projection (732) may also be configured to prevent clamp arm (760) from flexing upwardly at all when clamp arm (760) is retracted to the "inoperative position." It should also be understood that projection (732) and/or some other feature of handle assembly (730) may include a feature that prevents clamp arm (760) from flexing downwardly when clamp arm (760) is retracted to the "inoperative position."

As best seen in FIG. 21B, with clamp arm (760) in the "operative position," a vertical gap exists between a top surface of clamp pad (762) and ultrasonic blade (752). Tissue may be positioned within this gap. Additionally, an operator may force clamp arm (760) to flex downwardly to provide a larger gap between the top surface of clamp pad (762) and blade (752), then position tissue in this gap as shown in FIG. 21C. For instance, the operator may use his or her index finger to force clamp arm (760) downwardly. The operator may then force clamp arm (760) to flex upwardly so as to capture the tissue between the top surface of clamp pad (762) and blade (752) as shown in FIG. 21D. For instance, the operator may use his or her index finger to force clamp arm (760) to flex upwardly. The operator may further urge clamp arm (760) toward shaft assembly (740) to compress tissue between clamp pad (762) and ultrasonic blade (752).

Blade (752) of the present example has a cylindraceous shape. Blade (752) may thus provide the same performance characteristics regardless of the angular position at which tissue contact blades (752). It should be understood, however, that blade (752) may have any other suitable shape, including but not limited to any other ultrasonic blade shapes shown or described herein and/or shown or described in any of the references cited herein.

In an exemplary use, the operator may readily transition instrument (720) between two modes of operation by translating clamp arm (760) between the operative position and the inoperative position. For instance, the operator may perform at least part of a surgical procedure with clamp arm (760) in the inoperative position, such that the operator uses ultrasonic blade (752) like a scalpel. The operator may thus grip and use instrument (720) in a manner similar to a grip and use of instrument (120) when clamp arm (760) is in the inoperative position. Within the same surgical procedure (or in a different surgical procedure), the operator may translate clamp arm (760) to the operative position, then compress tissue between clamp pad (762) and ultrasonic blade (752) as described above. The operator may transition between these two modes as many times as desired within a given surgical procedure. Other suitable ways in which instrument (720) may be used will be apparent to those of ordinary skill in the art in view of the teachings herein.

F. Exemplary Ultrasonic Scalpel with Slidable-Pivotable Clamp Arm

FIGS. 23A-23D illustrate yet another exemplary alternative ultrasonic surgical instrument (820) configured to be used as a scalpel. Instrument (820) may be used in conjunction with ultrasonic surgical system (10) which includes ultrasonic transducer (26) coupled with ultrasonic generator (12) via cable (14). Instrument (820) of this example comprises a handle assembly (830), a shaft assembly (840), and an end effector (850). Instrument (820) is configured to operate substantially similar to instrument (120) discussed above except for the differences discussed below. In particular, instrument (820) may be used to cut tissue and seal or weld tissue (e.g., a blood vessel, etc.) substantially simultaneously. Unlike instrument (120) discussed above, however, instrument (820) of the present example comprises a retractable clamp arm (860). As will be discussed in more detail below, clamp arm (860) is configured to slide between an "inoperative position" (FIG. 23A), when a user does not wish to use clamp arm (860), and an "operative position" (FIGS. 23B-23D), when the user desires to use clamp arm (860).

Clamp arm (860) comprises a clamp pad (862) and an slider actuator (864). In some versions, clamp pad (862) comprises polytetrafluoroethylene (PTFE). Alternatively, clamp pad (862) may comprise any other suitable material(s) as will be apparent to those of ordinary skill in the art in view of the teachings herein. Shaft assembly (840) comprises an elongate slot (844) formed in an outer sheath (842) of shaft assembly (840). A lateral arm (868) of clamp arm (860) is slidably and pivotably coupled within slot (844) of shaft assembly (840) via a pin (866) such that clamp arm (860) is longitudinally translatable and pivotable between the "inoperative position" (FIG. 23A) and the "operative position" (FIGS. 23B-23D). As will be discussed in more detail below, in the "inoperative position," clamp arm (860) is configured to rest atop handle assembly (830), adjacent to a top surface of handle assembly (830) and proximally of shaft assembly (840) and end effector (850).

Figure 23A:
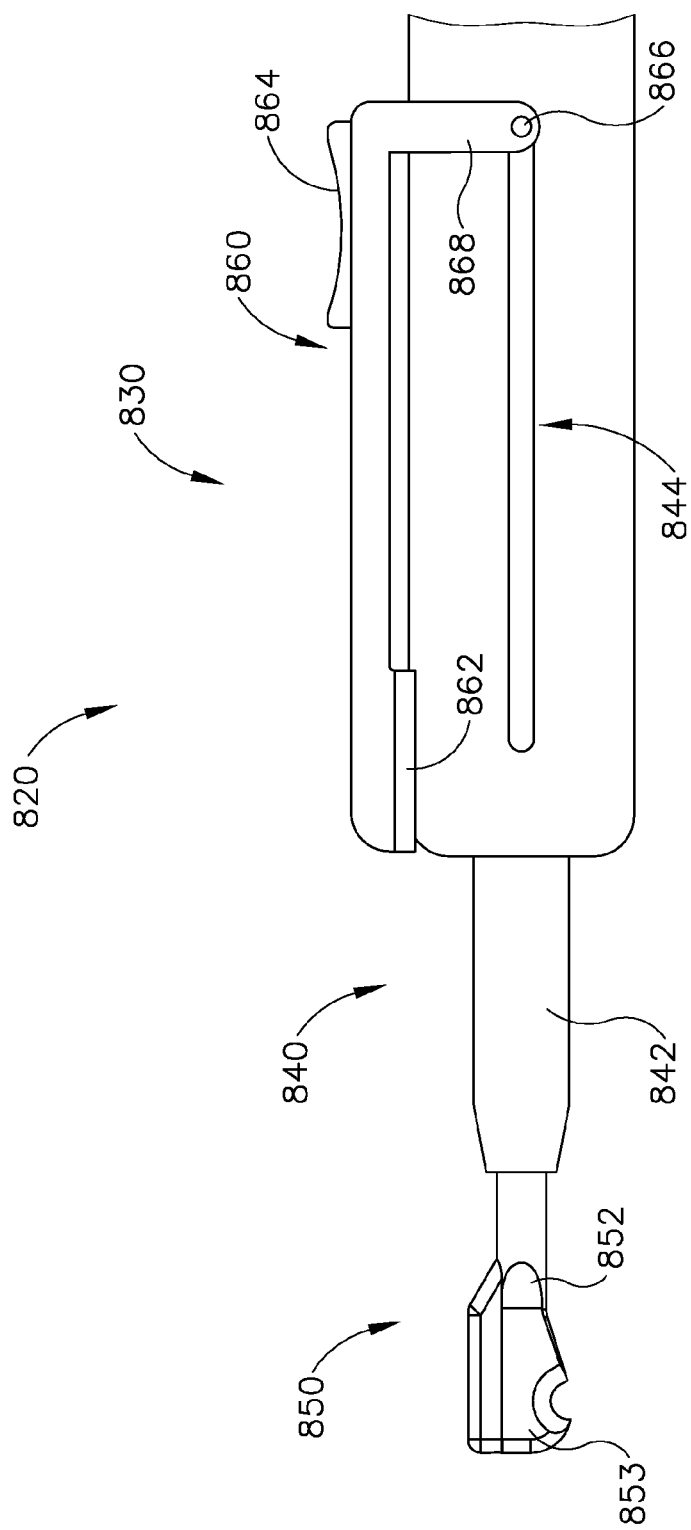
FIG. 23A depicts a side elevational view of a distal end of yet another exemplary alternative surgical instrument having a slidable clamp arm in a proximal position.
Figure 23B:
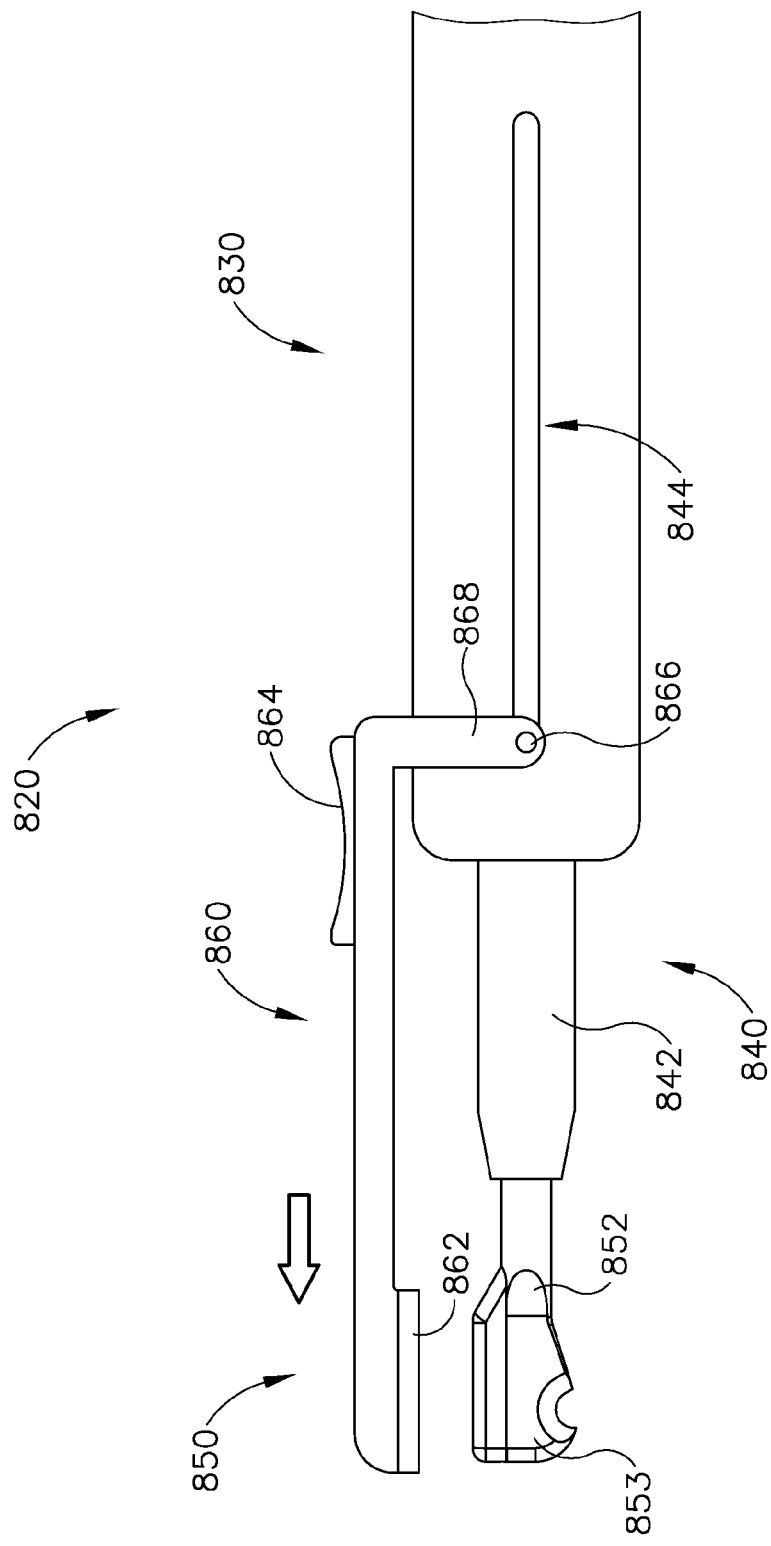
FIG. 23B depicts a side elevational view of the distal end of the instrument of FIG. 23A with the clamp arm longitudinally translated into a distal position.
Figure 23C:
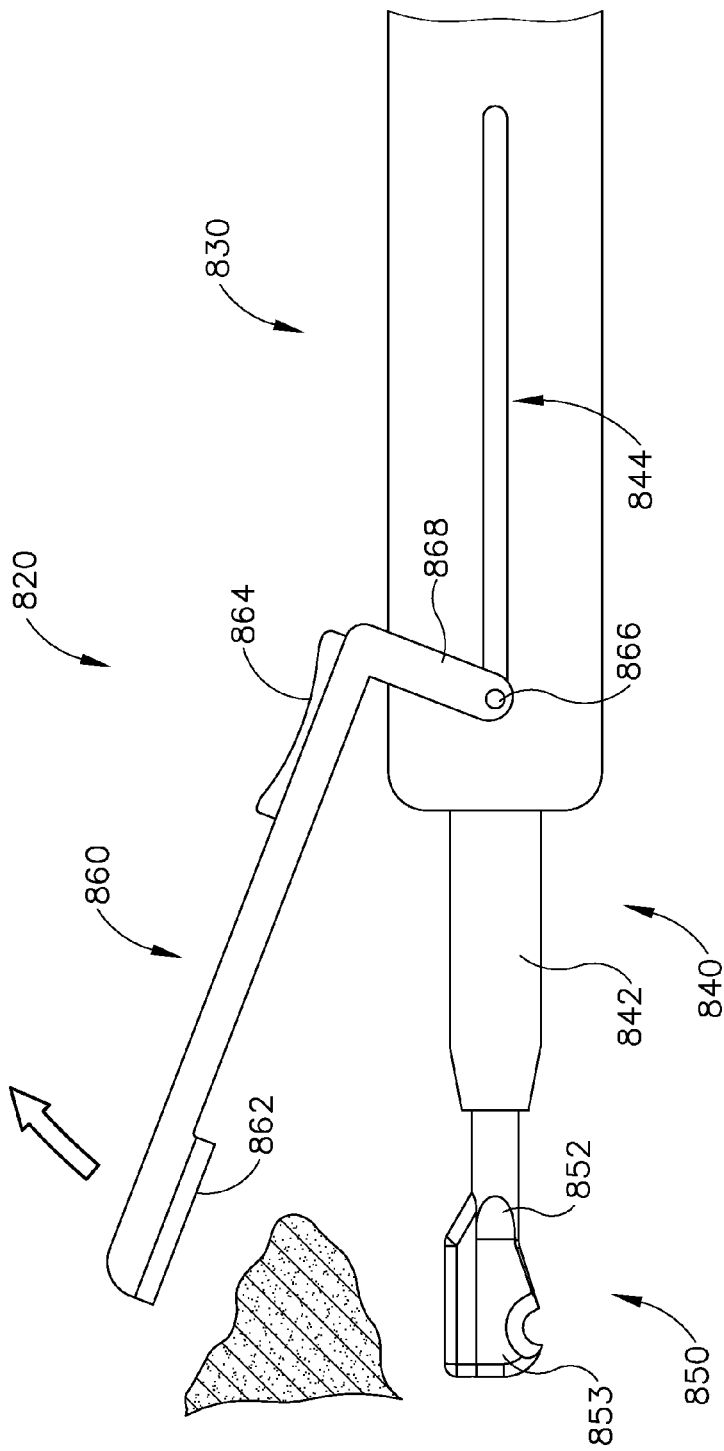
FIG. 23C depicts a side elevational view of the distal end of the instrument of FIG. 23A with the clamp arm in the distal position and rotated into an open position.
Figure 23D:
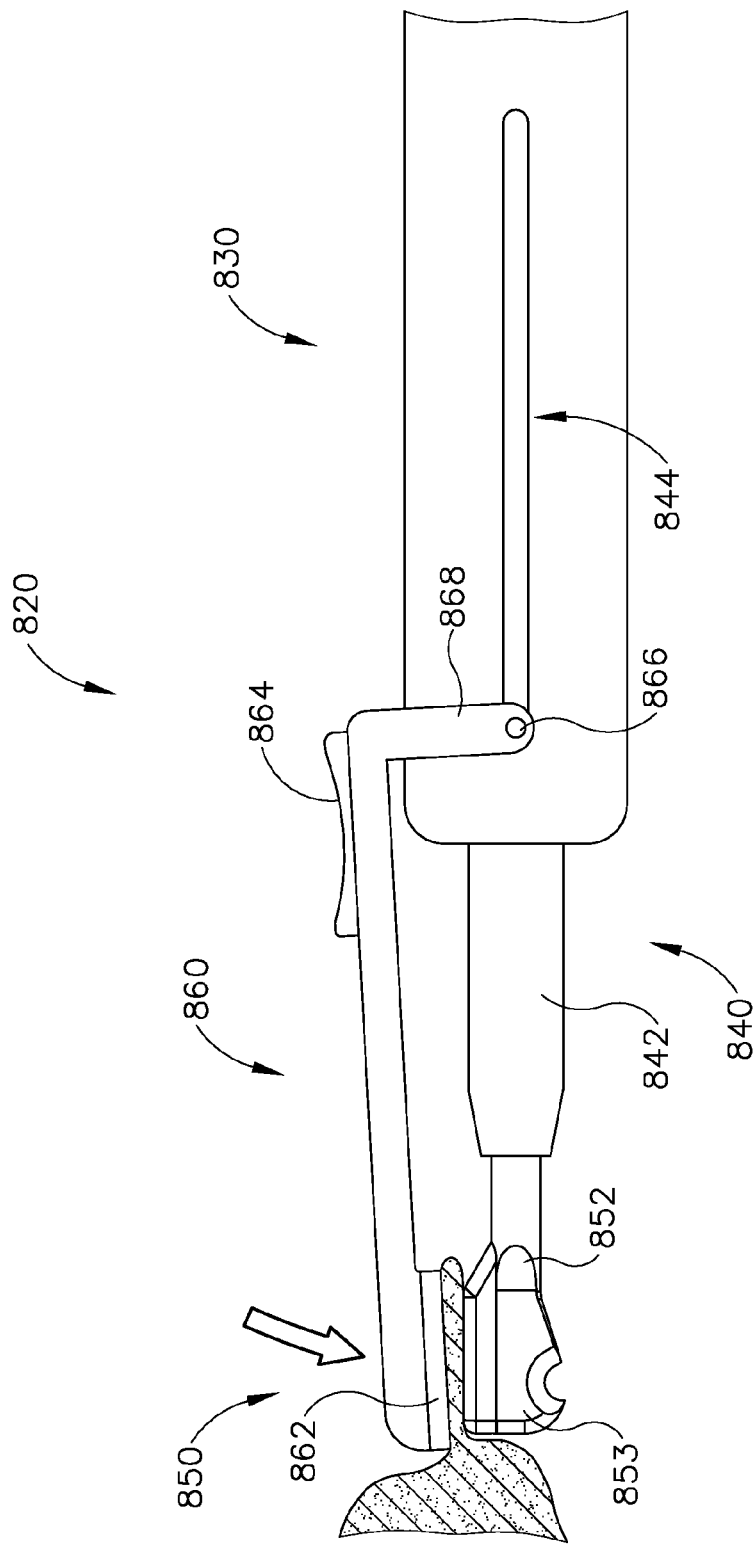
FIG. 23D depicts a side elevational view of the distal end of the instrument of FIG. 23A with the clamp arm in the distal position and rotated into a closed position.
Figure 24:
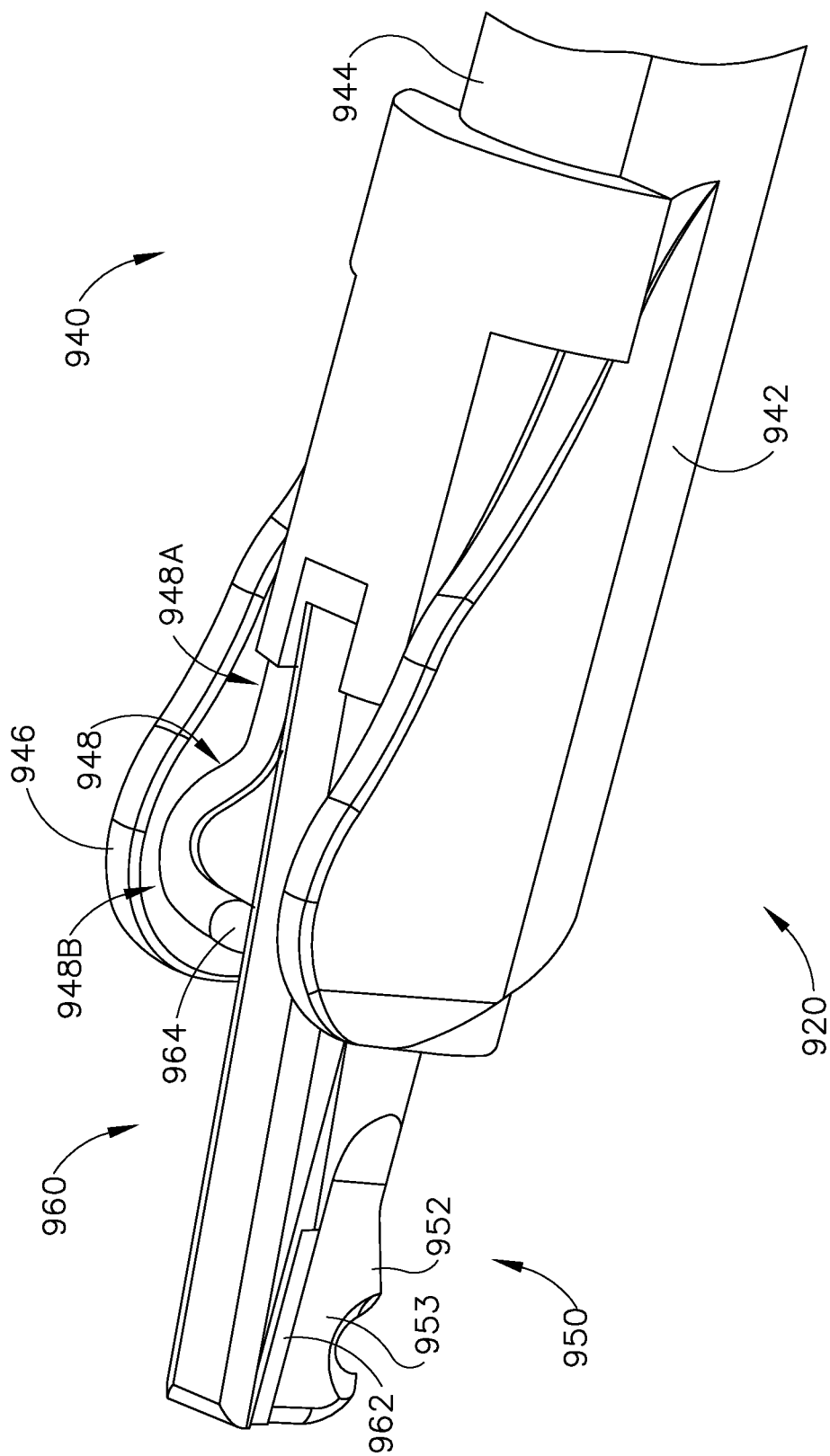
FIG. 24 depicts a perspective view of a distal end of yet another exemplary alternative surgical instrument having a slidable clamp arm in a distal position.

FIG. 23A shows clamp arm (860) in the "inoperative position." In the "inoperative position," clamp arm (860) rests atop handle assembly (830), adjacent to a top surface of handle assembly (830) and proximally of shaft assembly (840) and end effector (850). FIG. 23B shows clamp arm (860) translated distally within slot (844) via slider actuator (864) into the "operative position." In the "operative position," clamp pad (862) of clamp arm (860) is positioned directly above an ultrasonic blade (852) of end effector (850). With clamp arm (860) in the "operative position," a vertical gap exists between a bottom surface of clamp pad (862) and blade (852). Tissue may be positioned within this gap. Additionally, an operator may pivot clamp arm (860) upwardly about pin (866) to provide a larger gap between the bottom surface of clamp pad (860) and blade (852) into which tissue may be positioned as shown in FIG. 23C. For instance, the operator may use his or her thumb to pivot clamp arm (860) upwardly via slider actuator (864). The operator may then pivot clamp arm (860) downwardly about pin (866) so as to capture the tissue between the bottom surface of clamp pad (862) and blade (852) as shown in FIG. 23D. For instance, the operator may use his or her thumb to pivot clamp arm (860) downwardly via slider actuator (864). The operator may further urge clamp arm (860) toward shaft assembly (840) to compress tissue between clamp pad (862) and ultrasonic blade (852).

Blade (852) of the present example comprises a hook-shaped feature (853) which opens away from clamp pad (862). Hook-shaped feature (853) of blade (852) comprises a flat top surface or edge for compression of tissue between blade (852) and clamp pad (862). A bend and throat of hook-shaped feature (853) of blade (852), on the other hand, is thin such that the bend and throat of hook-shaped feature (853) may be used for cutting tissue without the assistance of clamp pad (862). Furthermore, hook-shaped feature (853) may be used to catch hold of and manipulate tissue. It should be understood, however, that blade (852) may have any other suitable shape, including but not limited to any other ultrasonic blade shapes shown or described herein and/or shown or described in any of the references cited herein.

In an exemplary use, the operator may readily transition instrument (820) between two modes of operation by translating clamp arm (860) between the operative position and the inoperative position. For instance, the operator may perform at least part of a surgical procedure with clamp arm (860) in the inoperative position, such that the operator uses ultrasonic blade (852) like a scalpel. The operator may thus grip and use instrument (820) in a manner similar to a grip and use of instrument (120) when clamp arm (860) is in the inoperative position. Within the same surgical procedure (or in a different surgical procedure), the operator may translate clamp arm (860) to the operative position, then compress tissue between clamp pad (862) and ultrasonic blade (852) as described above. The operator may transition between these two modes as many times as desired within a given surgical procedure. Other suitable ways in which instrument (820) may be used will be apparent to those of ordinary skill in the art in view of the teachings herein.

G. Exemplary Ultrasonic Scalpel with Slidable-Camming Clamp Arm

FIGS. 24-26F illustrate yet another exemplary alternative ultrasonic surgical instrument (920) configured to be used as a scalpel. Instrument (920) may be used in conjunction with ultrasonic surgical system (10) which includes ultrasonic transducer (26) coupled with ultrasonic generator (12) via cable (14). Instrument (920) of this example comprises a handle assembly (not shown), a shaft assembly (940), and an end effector (950). Instrument (920) is configured to operate substantially similar to instrument (120) discussed above except for the differences discussed below. In particular, instrument (920) may be used to cut tissue and seal or weld tissue (e.g., a blood vessel, etc.) substantially simultaneously. Unlike instrument (120) discussed above, however, instrument (920) of the present example comprises a retractable clamp arm (960). As will be discussed in more detail below, clamp arm (960) is configured to be translated and pivoted between an "inoperative position" (FIG. 26A), when a user does not wish to use clamp arm (960), and an "operative position" (FIGS. 26D-26F), when the user desires to use clamp arm (960).

Figure 25:
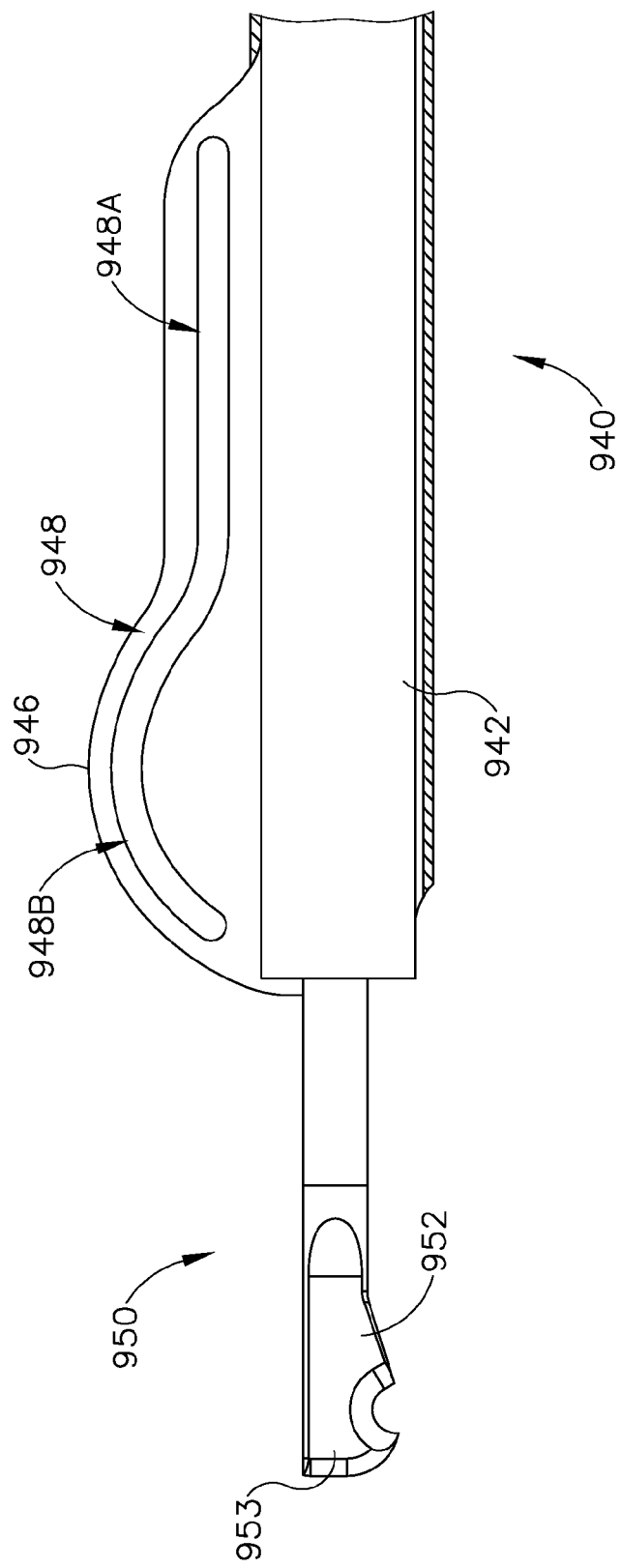
FIG. 25 depicts a cross-sectional side elevational view of a shaft assembly of the instrument of FIG. 24, with the clamp arm omitted.
Figure 26A:
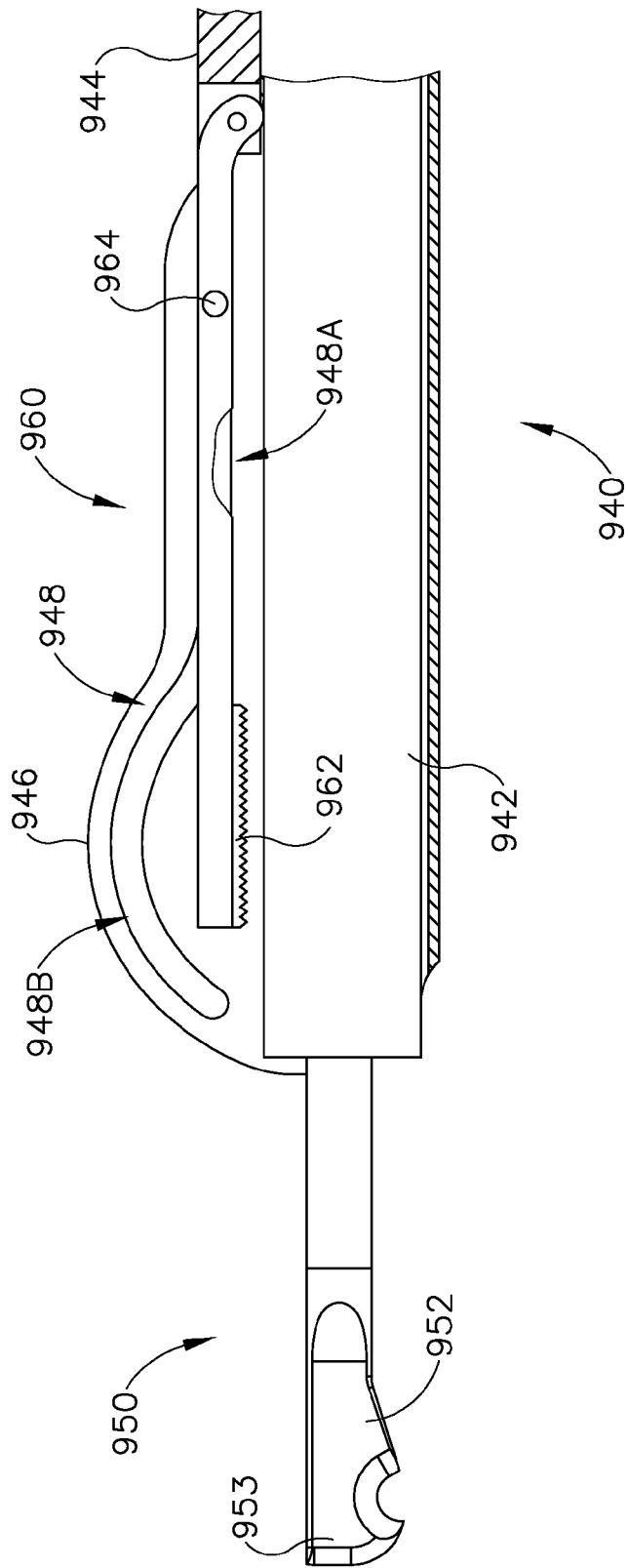
FIG. 26A depicts a cross-sectional side elevational view of the instrument of FIG. 24 with the clamp arm in a proximal position.

Clamp arm (960) comprises a clamp pad (962). In some versions, clamp pad (962) comprises polytetrafluoroethylene (PTFE). Alternatively, clamp pad (962) may comprise any other suitable material(s) as will be apparent to those of ordinary skill in the art in view of the teachings herein. Shaft assembly (940) comprises a translatable rod (944) and a pair of projections (946). A proximal end of clamp arm (960) is pivotably coupled to a distal end of rod (944) by a pin (#) such that clamp arm (960) is operable to pivot about the distal end of rod (944) at pin (#) and such that translation of rod (944) relative to shaft assembly (940) causes concurrent translation of clamp arm (960) relative to shaft assembly (940). Projections (946) extend upwardly from opposing side surfaces of an exterior surface of a distal end of an outer sheath (942) of shaft assembly (940). Each projection (946) comprises a slot (948) formed in an interior surface of each projection (946) such that slots (948) open toward one another. Slots (948) are shaped identically to each other. As best seen in FIG. 25, each slot (948) comprises a substantially straight, horizontal proximal portion (948A) and a bowed distal portion (948B). Clamp arm (960) is disposed between projections (946) of shaft assembly (940). Clamp arm (960) is slidably and pivotably coupled within slots (948) via a pair of pins (964), which extend outwardly from opposing side surfaces of clamp arm (960) such that clamp arm (960) is translatable and pivotable within slots (948) between the "inoperative position" (FIG. 26A) and the "operative position" (FIGS. 26D-26F). As will be discussed in more detail below, in the "inoperative position," clamp arm (960) is configured to rest atop outer sheath (942) of shaft assembly (940), adjacent to a top surface of outer sheath (942) and proximally of end effector (950).

FIG. 26A shows clamp arm (960) in the "inoperative position." In the "inoperative position," pins (964) are disposed within a proximal portion of substantially horizontal proximal portions (948A) of slots (948) such that clamp arm (960) rests atop outer sheath (942) of shaft assembly (940), adjacent to the top surface of outer sheath (942), proximally of end effector (950). In addition, clamp pad (962) is positioned between projections (946), such that clamp pad (962) is shielded by projections (946), when clamp arm (960) is in the "inoperative position."

Figure 26B:
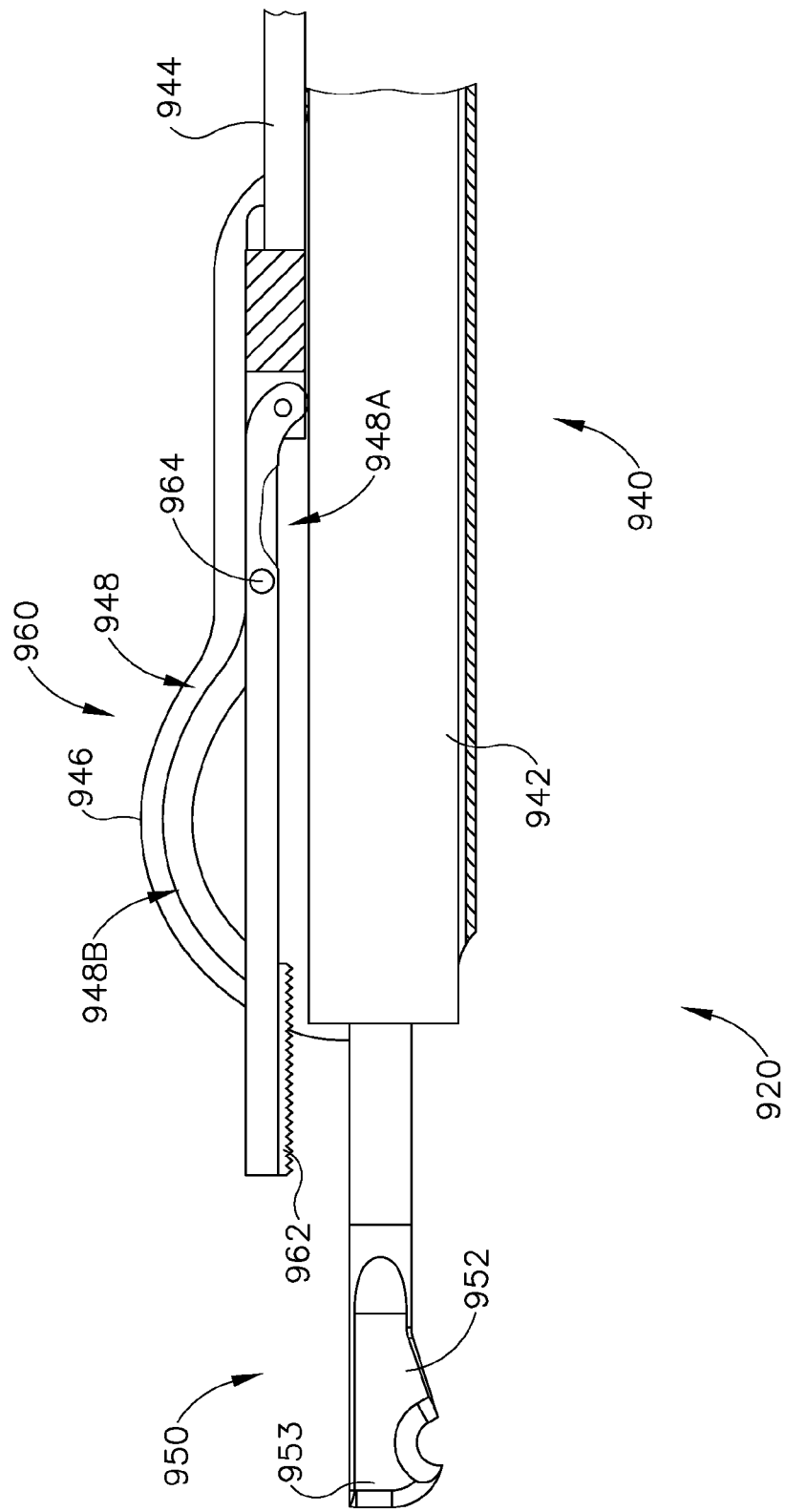
FIG. 26B depicts a cross-sectional side elevational view of the instrument of FIG. 24 with the clamp arm longitudinally translated into a first intermediate position.
Figure 26C:
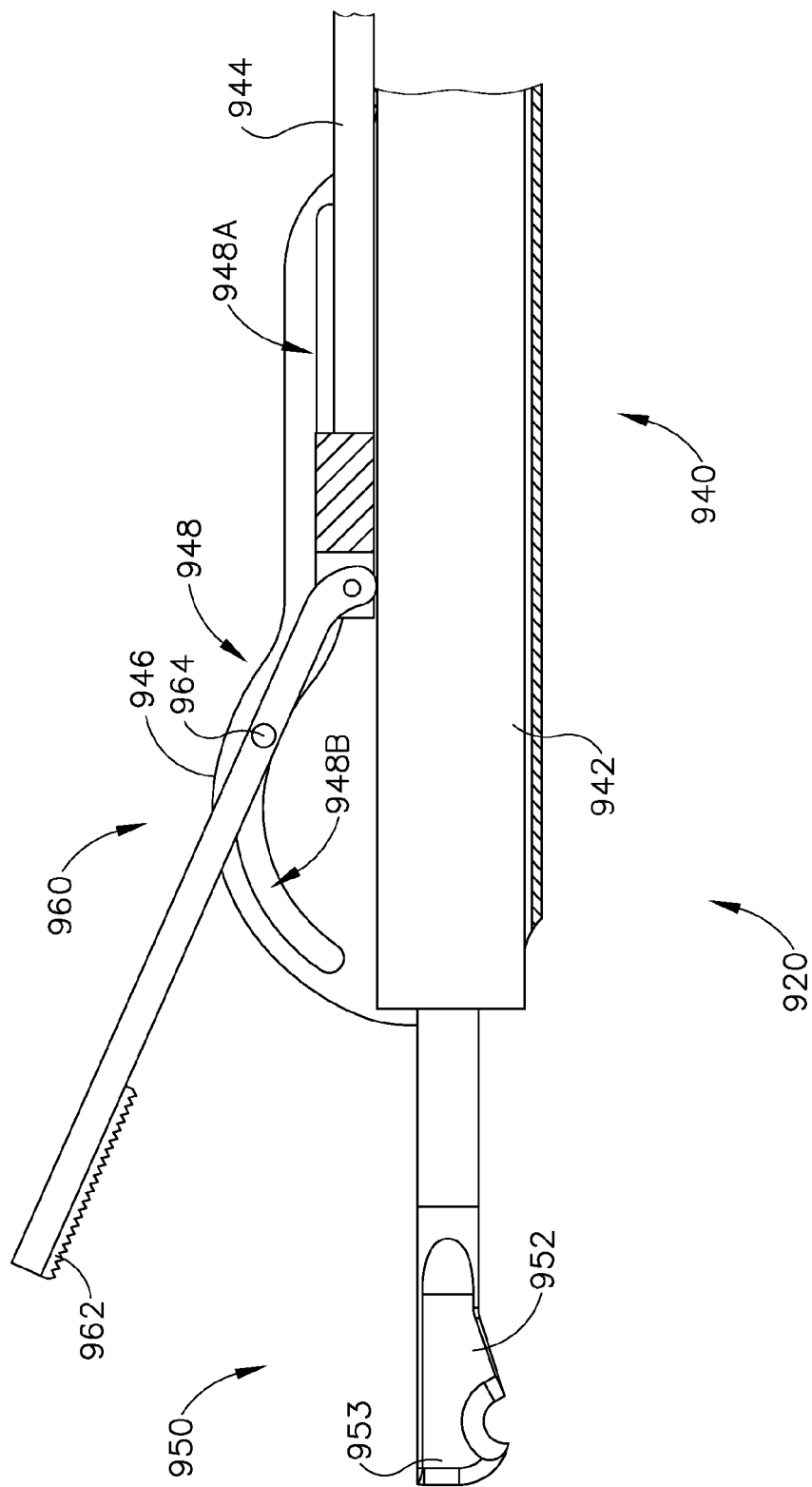
FIG. 26C depicts a cross-sectional side elevational view of the instrument of FIG. 24 with the clamp arm longitudinally translated and rotated into a second intermediate position.
Figure 26F:
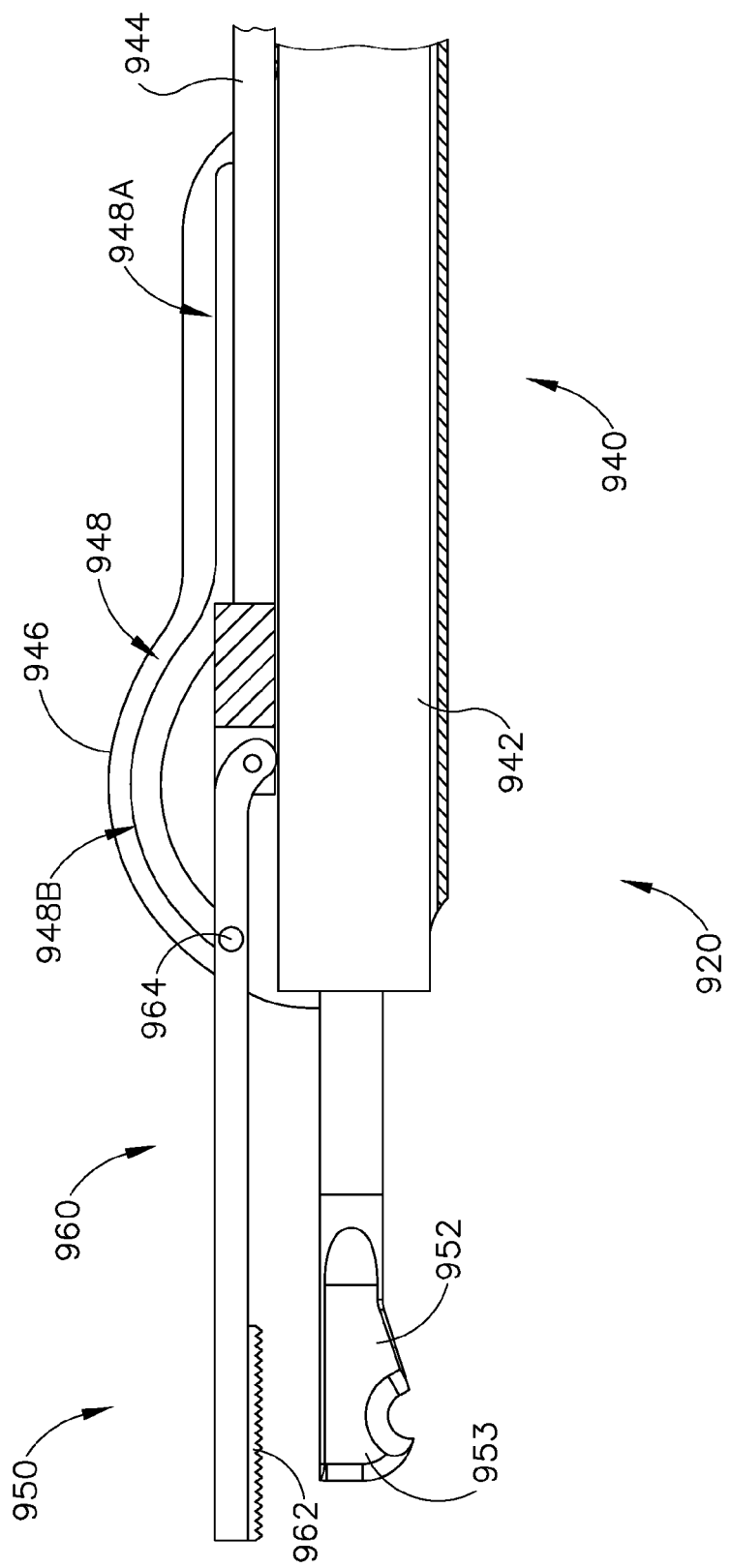
FIG. 26F depicts a cross-sectional side elevational view of the instrument of FIG. 24 with the clamp arm longitudinally translated and rotated into the distal position.

FIG. 26B shows clamp arm (960) translated distally within slots (948) via rod (944) into a first intermediate position. In this position, pins (964) are disposed within a distal portion of substantially horizontal proximal portions (948A) of slots (948) such that clamp arm (960) remains atop outer sheath (942) of shaft assembly (940), adjacent to the top surface of outer sheath (942), substantially proximally of end effector (950). FIG. 26C shows clamp arm (960) translated further distally within slots (948) via rod (944) into a second intermediate position. In this position, pins (964) are disposed within a proximal portion of bowed distal portion (948B) of slots (948). Engagement between pins (964) of clamp arm (960) and bowed distal portion (948B) of slots (948) causes clamp arm (960) to pivot upwardly about pin (#). FIG. 26D shows clamp arm (960) translated still further distally within slots (948) via rod (944) into the "operative position." In this position, pins (964) are disposed within an intermediate/apex portion of bowed distal portion (948B) of slots (948). Engagement between pins (964) of clamp arm (960) and bowed distal portion (948B) of slots (948) causes clamp arm (960) to pivot further upwardly about pin (#) into an open position. With clamp arm (960) in the open position, a gap exists between a bottom surface of clamp pad (962) and an ultrasonic blade (952) of end effector (950). Tissue may be positioned within this gap.

FIGS. 26E and 26F show clamp arm (960) translated still further distally within slots (948) via rod (944). In these positions, pins (964) are disposed within a distal portion of bowed distal portion (948B) of slots (948). Engagement between pins (964) of clamp arm (960) and bowed distal portion (948B) of slots (948) causes clamp arm (960) to pivot downwardly about the distal end of rod (944) into a closed position as rod (944) is translated distally so as to capture and compress the tissue between the bottom surface of clamp pad (962) and blade (952).

As with blade (852) discussed above, blade (952) of the present example comprises a hook-shaped feature (953) which opens away from clamp pad (962). Hook-shaped feature (953) of blade (952) comprises a flat top surface or edge for compression of tissue between blade (952) and clamp pad (962). A bend and throat of hook-shaped feature (953) of blade (952), on the other hand, is thin such that the bend and throat of hook-shaped feature (953) may be used for cutting tissue without the assistance of clamp pad (962). Furthermore, hook-shaped feature (953) may be used to catch hold of and manipulate tissue. It should be understood, however, that blade (952) may have any other suitable shape, including but not limited to any other ultrasonic blade shapes shown or described herein and/or shown or described in any of the references cited herein.

It should therefore be understood that rod (944) may be actuated through a first range of distal motion to transition clamp arm (960) from the inoperative position to an operative position; and then through a second range of distal motion to transition clamp arm (960) from an open operative configuration to a closed operative configuration relative to blade (952). In other words, once clamp arm (960) reaches the stage shown in FIG. 26D, clamp arm (960) may be regarded as being in an operative position. It should also be understood that the operator may reciprocate rod (944) longitudinally between the position shown in FIG. 26D and the position shown in FIG. 26F to repeatedly open and close clamp arm (960) relative to blade (952). Various suitable features that may be used to drive rod (944) longitudinally will be apparent to those of ordinary skill in the art in view of the teachings herein.

In an exemplary use, the operator may readily transition instrument (920) between two modes of operation by translating clamp arm (960) between the operative position and the inoperative position. For instance, the operator may perform at least part of a surgical procedure with clamp arm (960) in the inoperative position, such that the operator uses ultrasonic blade (952) like a scalpel. The operator may thus grip and use instrument (920) in a manner similar to a grip and use of instrument (120) when clamp arm (960) is in the inoperative position. Within the same surgical procedure (or in a different surgical procedure), the operator may translate clamp arm (960) to the operative position, then compress tissue between clamp pad (962) and ultrasonic blade (952) as described above. The operator may transition between these two modes as many times as desired within a given surgical procedure. Other suitable ways in which instrument (920) may be used will be apparent to those of ordinary skill in the art in view of the teachings herein.

H. Exemplary Ultrasonic Scalpel with Ramp-Guided Clamp Arm

FIGS. 27A-27D illustrate yet another exemplary alternative ultrasonic surgical instrument (1020) configured to be used as a scalpel. Instrument (1020) may be used in conjunction with ultrasonic surgical system (10) which includes ultrasonic transducer (26) coupled with ultrasonic generator (12) via cable (14). Instrument (1020) of this example comprises a handle assembly (not shown), a shaft assembly (1040), and an end effector (1050). Instrument (1020) is configured to operate substantially similar to instrument (120) discussed above except for the differences discussed below. In particular, instrument (1020) may be used to cut tissue and seal or weld tissue (e.g., a blood vessel, etc.) substantially simultaneously. Unlike instrument (120) discussed above, however, instrument (1020) of the present example comprises a retractable clamp arm (1060). As will be discussed in more detail below, clamp arm (1060) is configured to be translated and pivoted between an "inoperative position" (FIG. 27A), when a user does not wish to use clamp arm (1060), and an "operative position" (FIGS. 27C-27D), when the user desires to use clamp arm (1060).

Clamp arm (1060) comprises a clamp pad (1062), a proximal arm (1063), and a lateral arm (1064). In some versions, clamp pad (1062) comprises polytetrafluoroethylene (PTFE). Alternatively, clamp pad (1062) may comprise any other suitable material(s) as will be apparent to those of ordinary skill in the art in view of the teachings herein. Shaft assembly (1040) comprises an outer sheath (1042) and a translatable tube (1044). Translatable tube (1044) is slidably disposed about outer sheath (1042) such that translatable tube (1044) is longitudinally translatable about outer sheath (1042) relative to outer sheath (1042). A distal end of translatable tube (1044) comprises an arcuate slot (1046). Proximal arm (1063) of clamp arm (1060) is slidably and pivotably coupled within arcuate slot (1046) of translatable tube (1044) via a pin (1068) such that clamp arm (1060) is operable to pivot about the distal end of translatable tube (1044) and such that translation of translatable tube (1044) causes concurrent translation of clamp arm (1060). Outer sheath (1042) comprises an elongate slot (1048) and a ramped projection (1043) formed in a distal end of outer sheath (1042). Slot (1048) extends along a path that is parallel to the longitudinal axis of shaft assembly (1040). Lateral arm (1064) of clamp arm (1060) is slidably and pivotably coupled within slot (1048) via a pin (1066) of shaft assembly (1040) such that clamp arm (1060) is longitudinally translatable and pivotable between the "inoperative position" (FIG. 27A) and the "operative position" (FIGS. 27C-27D).

Figure 27A:
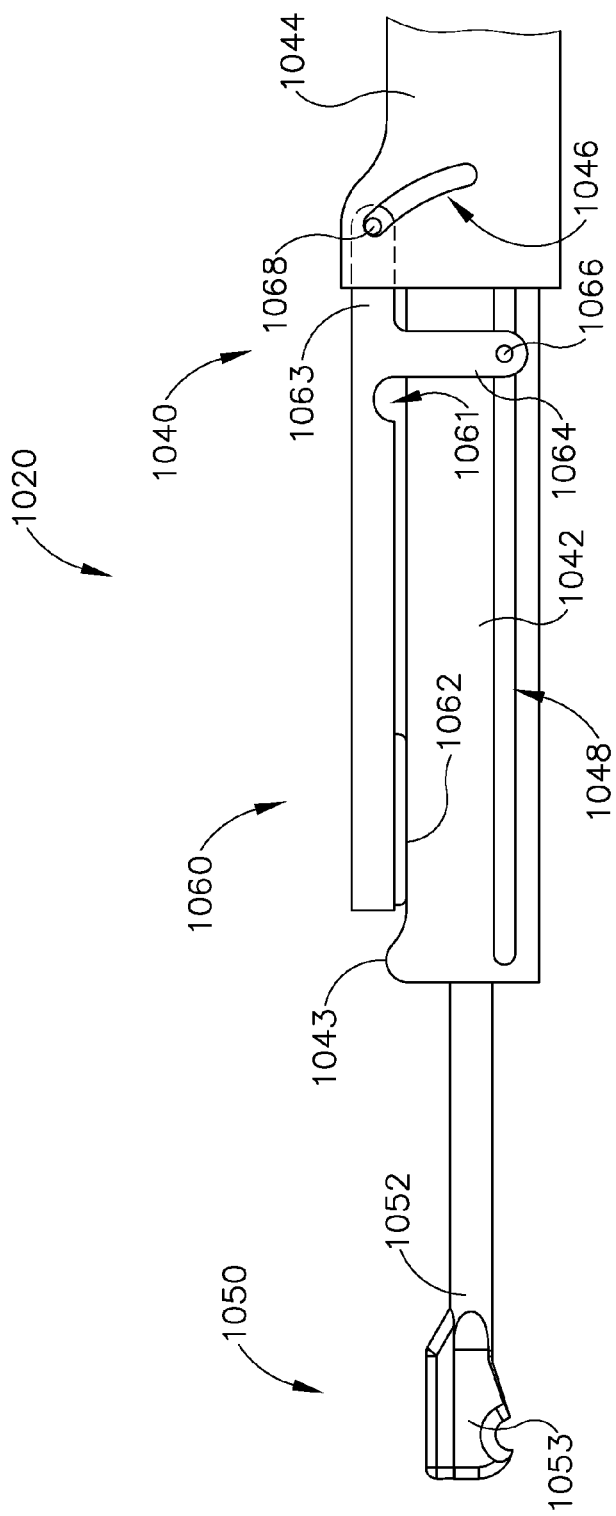
FIG. 27A depicts a side elevational view of a distal end of yet another exemplary alternative surgical instrument having a slidable clamp arm in a proximal position.
Figure 27B:
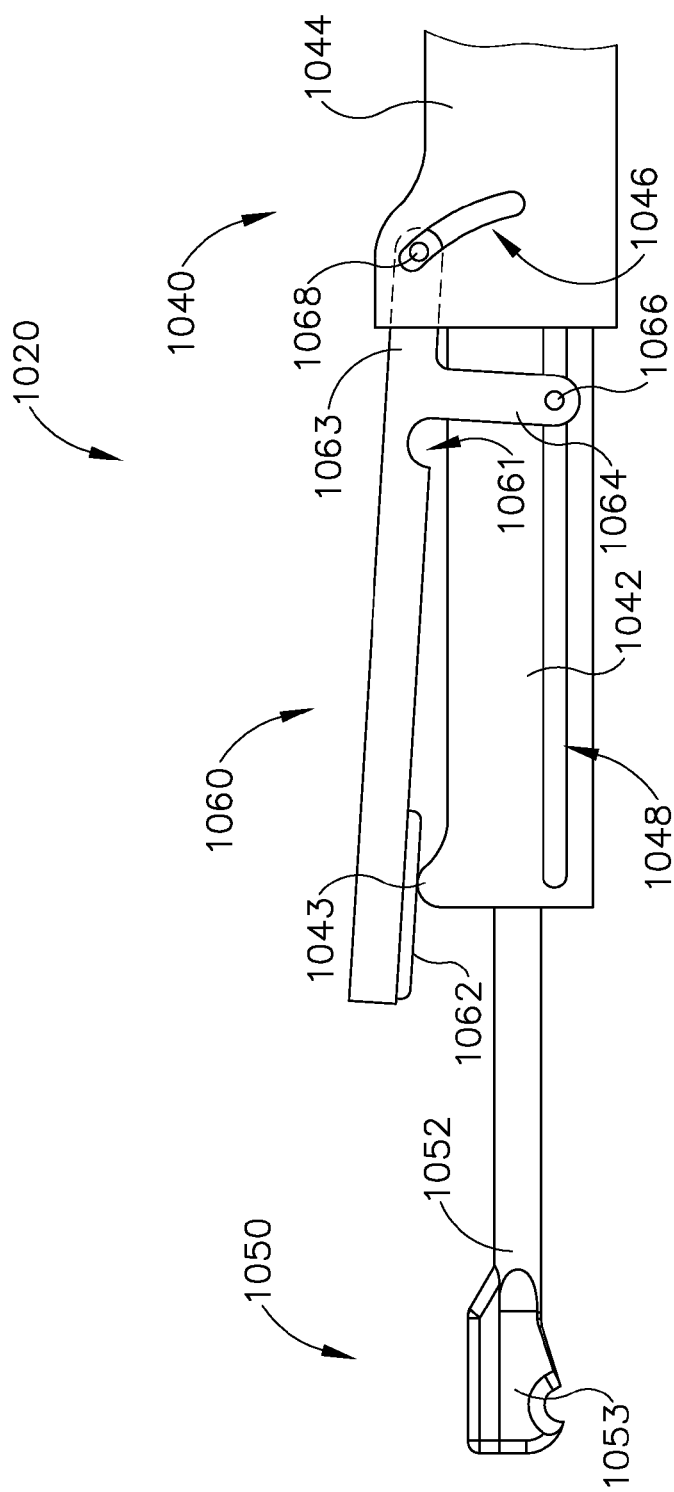
FIG. 27B depicts a side elevational view of the instrument of FIG. 27A with the clamp arm longitudinally translated and rotated into a first intermediate position.
Figure 27C:
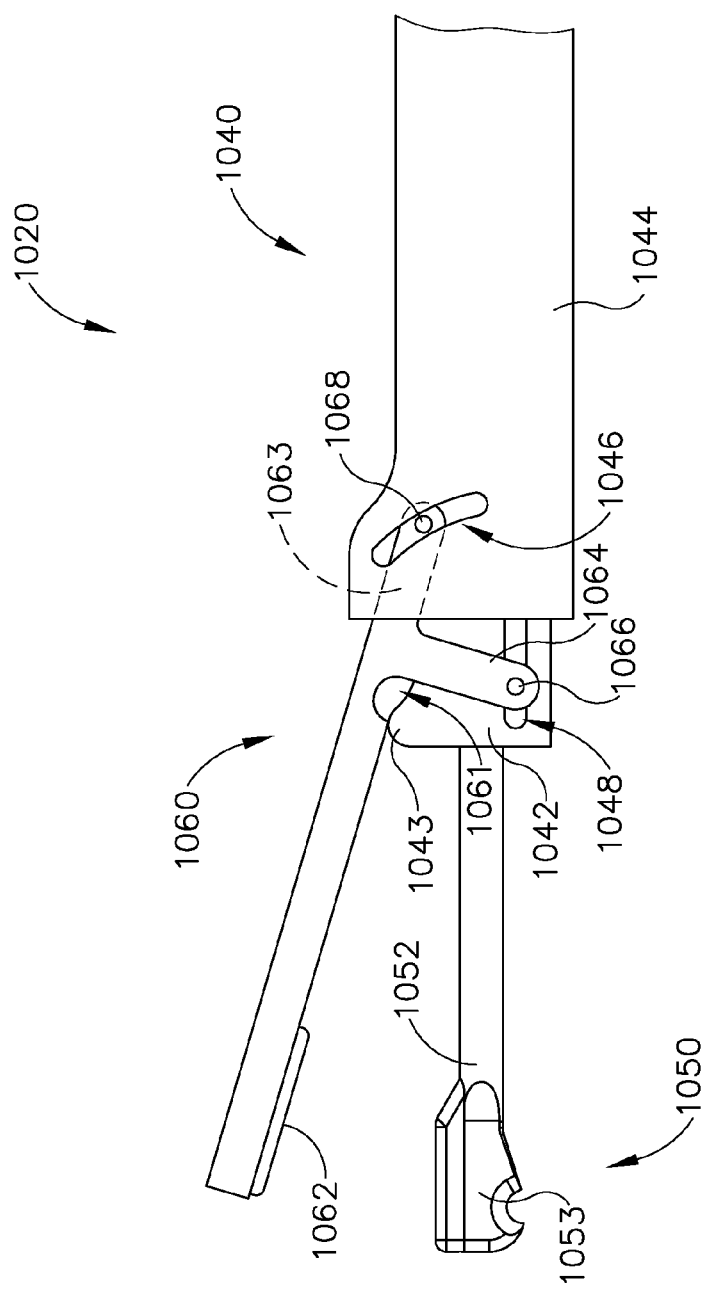
FIG. 27C depicts a side elevational view of the instrument of FIG. 27A with the clamp arm longitudinally translated and rotated into a second intermediate position.

FIG. 27A shows clamp arm (1060) in the "inoperative position." In the "inoperative position," pin (1066) of clamp arm (1060) is disposed within a proximal portion of substantially horizontal slot (1048), and pin (1068) is disposed within a top portion of arcuate slot (1046), such that clamp arm (1060) rests atop outer sheath (1042) of shaft assembly (1040), adjacent to the top surface of outer sheath (1042), proximally of ramp (1043) and end effector (1050). FIG. 27B shows clamp arm (1060) translated distally within slot (1048) via translatable tube (1044) into a first intermediate position. In this position, a distal end of a bottom surface of clamp arm (1060) engages ramp (1043) so as to cause clamp arm (1060) to pivot upwardly about pin (1066) within slot (1048). Ramp (1043) thus acts as a cam. As clamp arm (1060) pivots upwardly about pin (1066), pin (1068) of proximal arm (1063) slides downwardly within arcuate slot (1064). FIG. 27C shows clamp arm (1060) translated further distally within slot (1048) via translatable tube (1044) into a second intermediate position. In this position, an intermediate portion of the bottom surface of clamp arm (1060) engages ramp (1043) so as to cause clamp arm (1060) to pivot further upwardly about pin (1066) within slot (1048) in an open position. As clamp arm (1060) pivots further upwardly about pin (1066), pin (1068) of proximal arm (1063) slides further downwardly within arcuate slot (1064). With clamp arm (1060) in the open position, a gap exists between a bottom surface of clamp pad (1062) and an ultrasonic blade (1052) of end effector (1050). Tissue may be positioned within this gap.

Figure 27D:
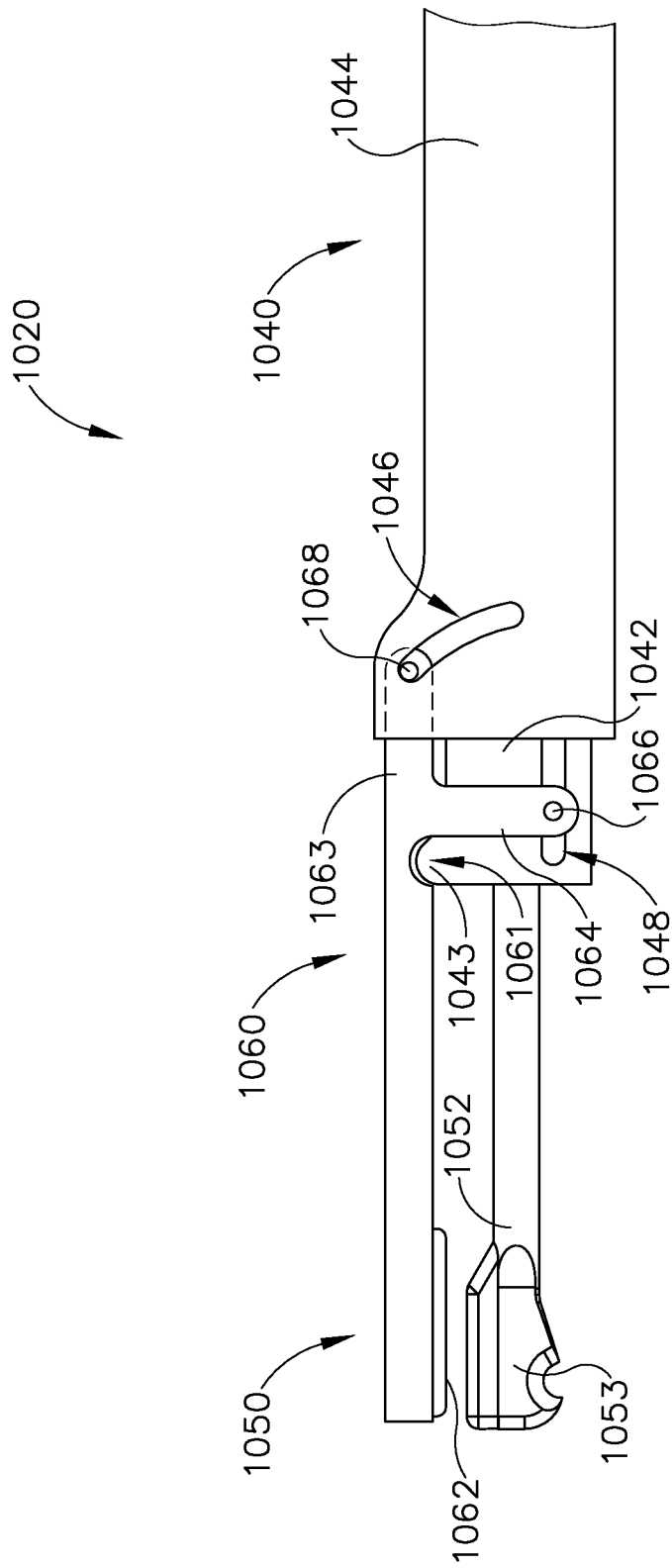
FIG. 27D depicts a side elevational view of the instrument of FIG. 27A with the clamp arm longitudinally translated and rotated into a distal position.

FIG. 27D shows clamp arm (1060) translated still further distally within slot (1048) via translatable tube (1044) into the "operative position." In this position, a recess (1061) formed in the bottom surface of clamp arm (1060) receives ramp (1043) so as to cause clamp arm (1060) to pivot downwardly about pin (1066) within slot (1048) into a closed position, thereby enabling capture and compression of tissue between the bottom surface of clamp pad (1062) and blade (1052). As clamp arm (1060) pivots downwardly about pin (1066), pin (1068) of proximal arm (1063) slides upwardly within arcuate slot (1064).

As with blades (852, 952) discussed above, blade (1052) of the present example comprises a hook-shaped feature (1053) which opens away from clamp pad (1062). Hook-shaped feature (1053) of blade (1052) comprises a flat top surface or edge for compression of tissue between blade (1052) and clamp pad (1062). A bend and throat of hook-shaped feature (1053) of blade (1052), on the other hand, is thin such that the bend and throat of hook-shaped feature (1053) may be used for cutting tissue without the assistance of clamp pad (1062). Furthermore, hook-shaped feature (1053) may be used to catch hold of and manipulate tissue. It should be understood, however, that blade (1052) may have any other suitable shape, including but not limited to any other ultrasonic blade shapes shown or described herein and/or shown or described in any of the references cited herein.

It should therefore be understood that tube (1044) may be actuated through a first range of distal motion to transition clamp arm (1060) from the inoperative position to an operative position; and then through a second range of distal motion to transition clamp arm (1060) from an open operative configuration to a closed operative configuration relative to blade (1052). In other words, once clamp arm (1060) reaches the stage shown in FIG. 27C, clamp arm (1060) may be regarded as being in an operative position. It should also be understood that the operator may reciprocate tube (1044) longitudinally between the position shown in FIG. 27C and the position shown in FIG. 27D to repeatedly open and close clamp arm (1060) relative to blade (1052). Various suitable features that may be used to drive tube (1044) longitudinally will be apparent to those of ordinary skill in the art in view of the teachings herein.

In an exemplary use, the operator may readily transition instrument (1020) between two modes of operation by translating clamp arm (1060) between the operative position and the inoperative position. For instance, the operator may perform at least part of a surgical procedure with clamp arm (1060) in the inoperative position, such that the operator uses ultrasonic blade (1052) like a scalpel. The operator may thus grip and use instrument (1020) in a manner similar to a grip and use of instrument (120) when clamp arm (1060) is in the inoperative position. Within the same surgical procedure (or in a different surgical procedure), the operator may translate clamp arm (1060) to the operative position, then compress tissue between clamp pad (1062) and ultrasonic blade (1052) as described above. The operator may transition between these two modes as many times as desired within a given surgical procedure. Other suitable ways in which instrument (1020) may be used will be apparent to those of ordinary skill in the art in view of the teachings herein.

Figure 28A:
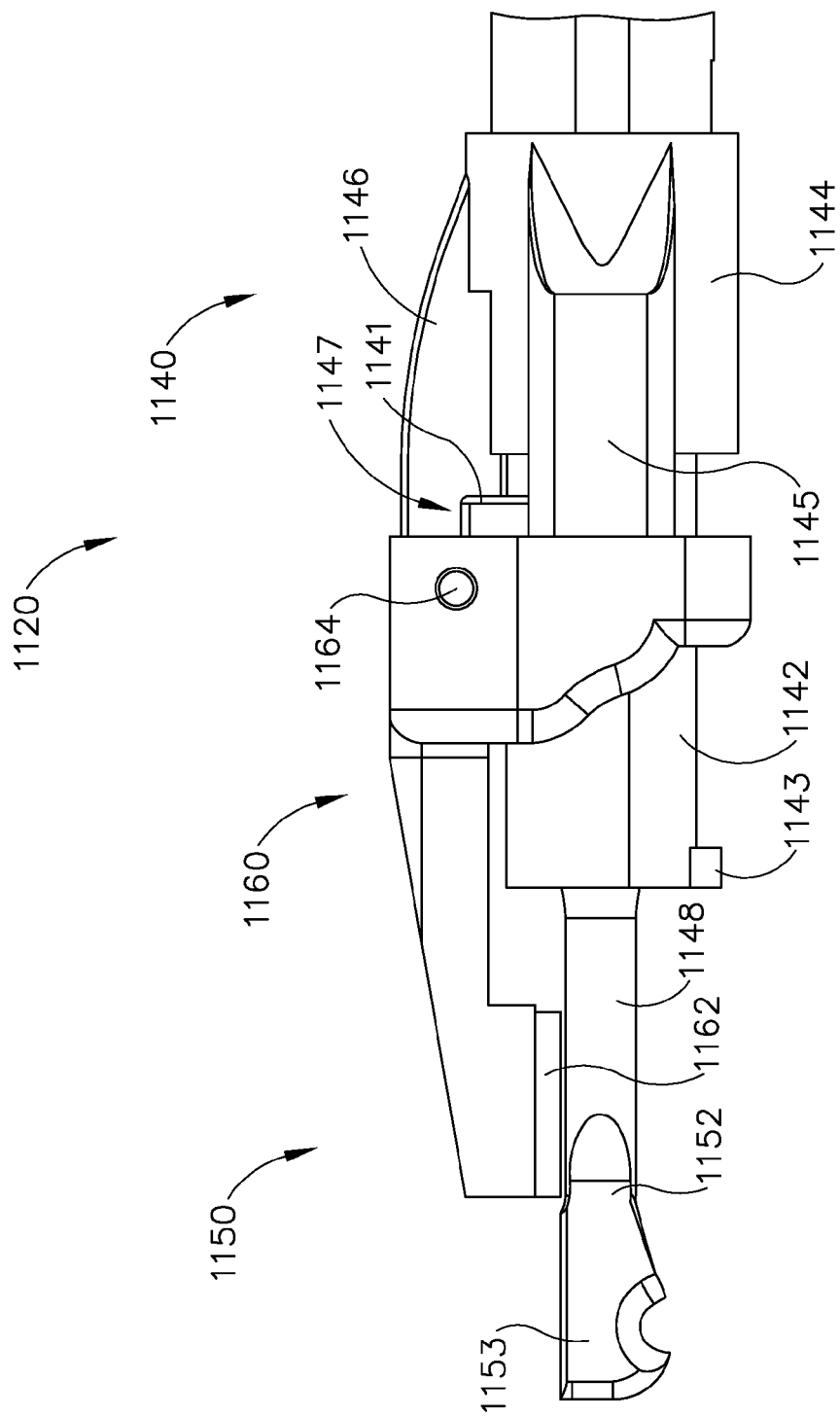
FIG. 28A depicts a side elevational view of a distal end of yet another exemplary alternative surgical instrument having a slidable clamp arm in a proximal position.
Figure 28B:
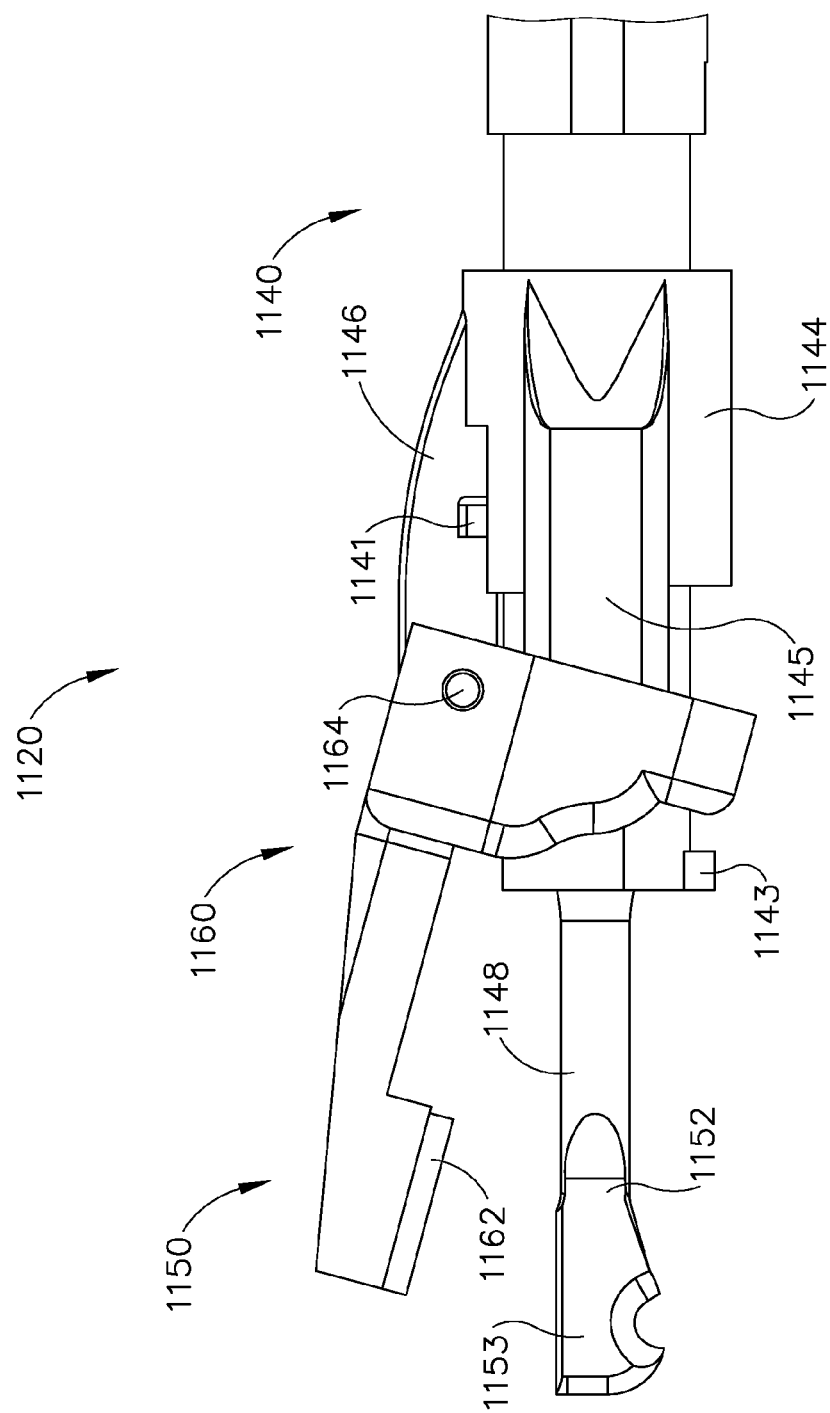
FIG. 28B depicts a side elevational view of the instrument of FIG. 28A with the clamp arm longitudinally translated and rotated into an intermediate position.
Figure 28C:
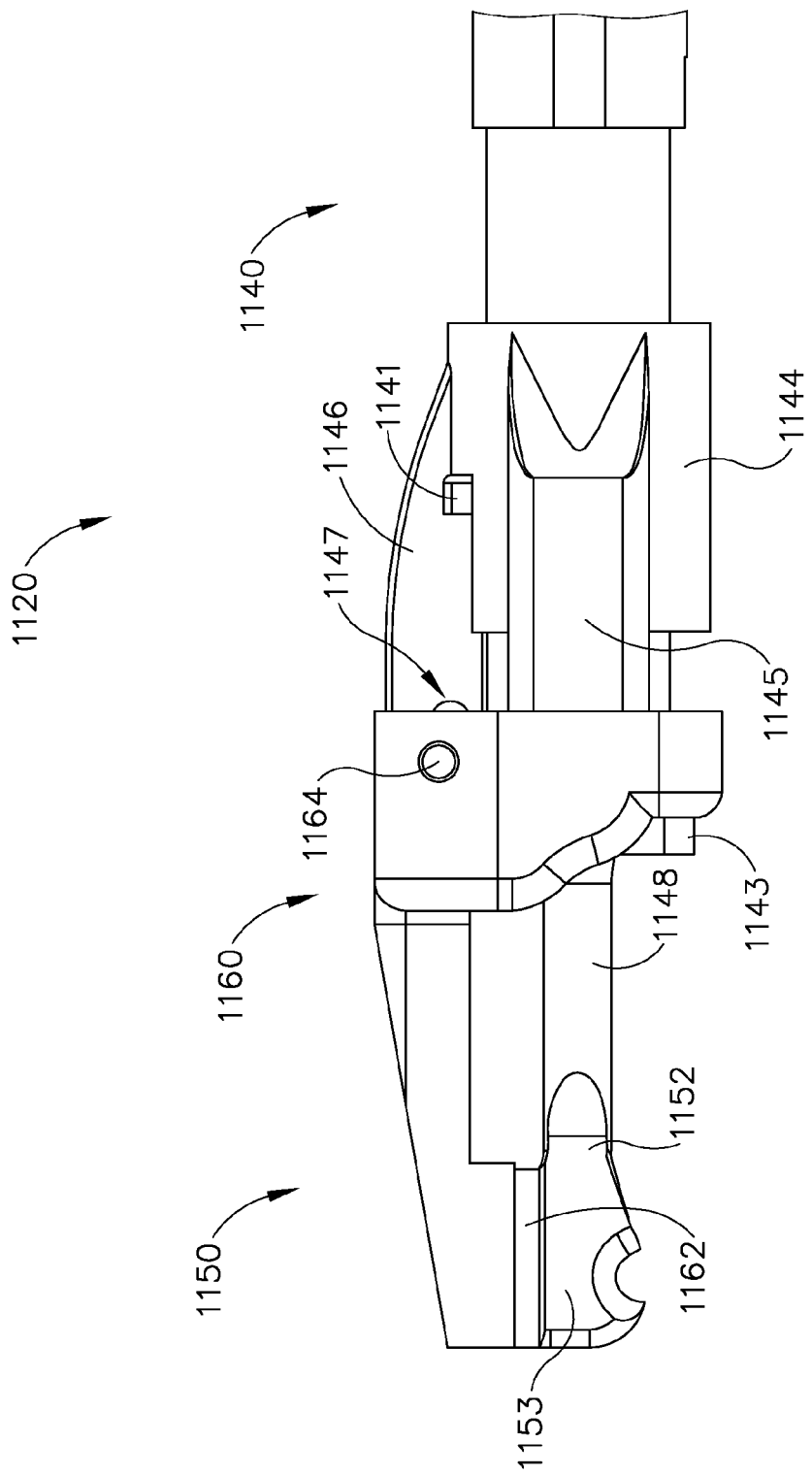
FIG. 28C depicts a side elevational view of the instrument of FIG. 28A with the clamp arm longitudinally translated and rotated into a distal position.

I. Exemplary Ultrasonic Scalpel with Clamp Arm Having Offset Translatable Guide Members FIGS. 28A-28C illustrate yet another exemplary alternative ultrasonic surgical instrument (1120) configured to be used as a scalpel. Instrument (1120) may be used in conjunction with ultrasonic surgical system (10) which includes ultrasonic transducer (26) coupled with ultrasonic generator (12) via cable (14). Instrument (1120) of this example comprises a handle assembly (not shown), a shaft assembly (1140), and an end effector (1150). Instrument (1120) is configured to operate substantially similar to instrument (120) discussed above except for the differences discussed below. In particular, instrument (1120) may be used to cut tissue and seal or weld tissue (e.g., a blood vessel, etc.) substantially simultaneously. Unlike instrument (120) discussed above, however, instrument (1120) of the present example comprises a retractable clamp arm (1160). As will be discussed in more detail below, clamp arm (1160) is configured to be translated and pivoted between an "inoperative position" (FIG. 28A), when a user does not wish to use clamp arm (1160), and an "operative position" (FIGS. 28B-28C), when the user desires to use clamp arm (1160).

Clamp arm (1160) comprises a clamp pad (1162). In some versions, clamp pad (1162) comprises polytetrafluoroethylene (PTFE). Alternatively, clamp pad (1162) may comprise any other suitable material(s) as will be apparent to those of ordinary skill in the art in view of the teachings herein. Shaft assembly (1140) comprises an outer sheath (1142) and a translatable tube (1144). Shaft assembly (1140) further comprises an upper projection (1141) extending from a top surface of outer sheath (1142) and a lower projection (1143) extending from a bottom surface of outer sheath (1142). As will be discussed in more detail below, projections (1141, 1143) are configured to engage clamp arm (1160) to drive clamp arm (1160) into a closed position as shown in FIGS. 28A and 28C. A proximal end of clamp arm (1160) is slidably and pivotably disposed about outer sheath (1142) of shaft assembly (1140). Translatable tube (1144) is slidably disposed about outer sheath (1142) such that translatable tube (1144) is longitudinally translatable about outer sheath (1142) relative to outer sheath (1142). A bottom portion of the proximal end of clamp arm (1160) is pivotably coupled to a lower distal arm (1145) of translatable tube (1144) such that clamp arm (1160) is operable to pivot about the distal end of translatable tube (1144) and such that translation of translatable tube (1144) causes concurrent translation or pivoting of clamp arm (1160). A top portion of the proximal end of clamp arm (1160) is slidably and pivotably coupled within an arcuate slot (1147) of an upper distal arm (1146) via a pin (1164) such that clamp arm (1160) is further operable to pivot about the distal end of translatable rod (1146). As will be discussed in more detail below, clamp arm (1160) is biased toward an open position shown in FIG. 28B by a resilient member (not shown). By way of example only, the resilient member may comprise a torsion spring, a leaf spring, a coil spring, and/or any other suitable kind of resilient member(s).

FIG. 28A shows clamp arm (1160) in the "inoperative position." In the "inoperative position," clamp arm (1160) is drawn proximally such that a proximal face of clamp arm (1160) engages upper projection (1141) of outer sheath (1142). This engagement between clamp arm (1160) and upper projection (1141) causes clamp arm (1160) to overcome the bias of clamp arm (1160) toward the open position, thereby driving clamp arm (1160) into the closed position and holding clamp arm (1160) in the closed position. In the closed position, clamp pad (1162) is positioned adjacent to the top surface of an ultrasonic waveguide (1148), proximal to an ultrasonic blade (1152) of end effector (1150). FIG. 28B shows clamp arm (1160) translated distally via translation of translatable tube (1144). In this position, clamp arm (1160) no longer engages upper projection (1141), such that clamp arm (1160) is driven into the open position by the resilient member (not shown). With clamp arm (1160) in the open position, a gap exists between a bottom surface of clamp pad (1162) and an ultrasonic blade (1152) of end effector (1150). Tissue may be positioned within this gap. FIG. 28C shows clamp arm (1160) translated further distally via translation of translatable tube (1144). In this position, a distal face of clamp arm (1160) engages lower projection (1143) of outer sheath (1142). This engagement between clamp arm (1160) and lower projection (1143) causes clamp arm (1160) to overcome the bias of clamp arm (1160) toward the open position so as to cause clamp arm (1160) to pivot downwardly about distal arm (1145) into a closed position, thereby capturing and compressing the tissue between the bottom surface of clamp pad (1162) and blade (1152).

As with blades (852, 952, 1052) discussed above, blade (1152) of the present example comprises a hook-shaped feature (1153) which opens away from clamp pad (1162). Hook-shaped feature (1153) of blade (1152) comprises a flat top surface or edge for compression of tissue between blade (1152) and clamp pad (1162). A bend and throat of hook-shaped feature (1153) of blade (1152), on the other hand, is thin such that the bend and throat of hook-shaped feature (1153) may be used for cutting tissue without the assistance of clamp pad (1162). Furthermore, hook-shaped feature (1153) may be used to catch hold of and manipulate tissue. It should be understood, however, that blade (1152) may have any other suitable shape, including but not limited to any other ultrasonic blade shapes shown or described herein and/or shown or described in any of the references cited herein.

In view of the foregoing, tube (1144) may be actuated through a first range of distal motion to transition clamp arm (1160) from the inoperative position to an operative position; and then through a second range of distal motion to transition clamp arm (1160) from an open configuration to a closed configuration relative to blade (1152). In other words, once clamp arm (1160) reaches the stage shown in FIG. 28B, clamp arm (1160) may be regarded as being in an operative position. It should also be understood that the operator may reciprocate tube (1144) longitudinally between the position shown in FIG. 28B and the position shown in FIG. 28C to repeatedly open and close clamp arm (1160) relative to blade (1152). Various suitable features that may be used to drive tube (1144) longitudinally will be apparent to those of ordinary skill in the art in view of the teachings herein.

In an exemplary use, the operator may readily transition instrument (1120) between two modes of operation by translating clamp arm (1160) between the operative position and the inoperative position. For instance, the operator may perform at least part of a surgical procedure with clamp arm (1160) in the inoperative position, such that the operator uses ultrasonic blade (1152) like a scalpel. The operator may thus grip and use instrument (1120) in a manner similar to a grip and use of instrument (120) when clamp arm (1160) is in the inoperative position. Within the same surgical procedure (or in a different surgical procedure), the operator may translate clamp arm (1160) to the operative position, then compress tissue between clamp pad (1162) and ultrasonic blade (1152) as described above. The operator may transition between these two modes as many times as desired within a given surgical procedure. Other suitable ways in which instrument (1120) may be used will be apparent to those of ordinary skill in the art in view of the teachings herein.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
   (a) a shaft assembly, wherein the shaft assembly defines a longitudinal axis, wherein the shaft assembly comprises an acoustic waveguide, wherein the acoustic waveguide is configured to communicate acoustically with an ultrasonic transducer;
   (b) an ultrasonic blade, wherein the ultrasonic blade is in acoustic communication with the acoustic waveguide such that the ultrasonic transducer is operable to drive the ultrasonic blade to vibrate ultrasonically via the acoustic waveguide; and
   (c) a clamp arm, wherein the clamp arm comprises a proximal portion and a distal portion separated by a pivot axis positioned therebetween, wherein the distal portion includes a clamp pad, wherein the proximal and distal portions are configured to pivot about the pivot axis such that the clamp pad is configured to pivot toward and away from the ultrasonic blade wherein the proximal portion of the clamp arm is pivotable about the pivot axis toward a proximal portion of the shaft assembly as the clamp pad pivots toward the ultrasonic blade, wherein the clamp arm is moveable between an inoperative position and an operative position, wherein the proximal and distal portions of the clamp arm and the pivot axis are configured to translate along a straight path parallel to the longitudinal axis as the clamp arm moves between the inoperative position and the operative position, wherein the clamp pad in the inoperative position is positioned proximally of the ultrasonic blade, wherein the clamp pad in the operative position is positioned lateral to the ultrasonic blade.

2. The ultrasonic instrument of claim 1, wherein when in the operative position the clamp pad is pivotable toward and away from the ultrasonic blade.

3. The ultrasonic instrument of claim 1, further comprising a body, wherein the body comprises at least one slot, wherein the clamp arm comprises a pivot pin defining the pivot axis, wherein the pivot pin is configured to translate within the slot between the inoperative position and the operative position.

4. The ultrasonic instrument of claim 3, wherein the at least one slot is shaped so as to cause rotation of the clamp arm about the ultrasonic instrument as the clamp aim is translated between the inoperative position and the operative position.

5. The ultrasonic instrument of claim 3, wherein the at least one slot is shaped so as to cause pivoting of the clamp arm toward or away from the ultrasonic instrument as the clamp arm is translated between the inoperative position and the operative position.

6. The ultrasonic instrument of claim 5, wherein the at least one slot comprises at least one bow-shaped portion and at least one substantially straight portion.

7. The ultrasonic instrument of claim 6, wherein the at least one slot further comprises at least one circle-shaped portion.

8. The ultrasonic instrument of claim 3, wherein the at least one slot comprises a pair of slots formed in the body.

9. The ultrasonic instrument of claim 3, wherein the at least one slot comprises a pair of slots formed in the shaft assembly.

10. The ultrasonic instrument of claim 1, wherein the ultrasonic blade is further operable to deliver RF energy, wherein the clamp pad further comprises an RF return electrode.

11. The ultrasonic instrument of claim 1, wherein the clamp arm is pivotably coupled to a first translatable member, wherein the first translatable member is configured to translate longitudinally relative to the shaft assembly to thereby cause pivoting of the clamp arm or movement of the clamp arm between the inoperative position and the operative position.

12. The ultrasonic instrument of claim 11, wherein the clamp arm is further pivotably coupled to a second translatable member, wherein the first translatable member and the second translatable member are configured to constantly and simultaneously translate longitudinally relative to the shaft assembly to thereby cause movement of the clamp arm between the inoperative position and the operative position.

13. The ultrasonic instrument of claim 12, further comprising a body, wherein the body comprises a handle assembly.

14. An ultrasonic instrument comprising:
(a) a body including an ultrasonic transducer;
(b) a shaft assembly, wherein the shaft assembly defines a longitudinal axis extending between a proximal end and a distal end, wherein the shaft assembly comprises an acoustic waveguide, wherein the acoustic waveguide is in acoustic communication with the ultrasonic transducer;
(c) an ultrasonic blade, wherein the ultrasonic blade is in acoustic communication with the acoustic waveguide such that the ultrasonic transducer is operable to drive the ultrasonic blade to vibrate ultrasonically via the acoustic waveguide; and
(d) a clamp arm, wherein the clamp arm comprises a clamp pad and an actuator, wherein the actuator and the clamp pad are pivotably and slidably coupled to the body, wherein the actuator is rotatable toward the proximal end of the shaft assembly to thereby rotate the clamp toward the ultrasonic blade, wherein the clamp pad is configured to be separately pivotable and translatable between an inoperative position and an operative position along the body, wherein the clamp pad in the inoperative position is positioned proximal to the ultrasonic blade, wherein the clamp pad in the operative position is positioned lateral to the ultrasonic blade.

15. The ultrasonic instrument of claim 14, further comprising at least one slot, wherein the clamp arm is translatable relative to the at least one slot between the inoperative position and the operative position.

16. The ultrasonic instrument of claim 15, wherein the at least one slot comprises a plurality of slots formed at least partially within the shaft assembly, wherein the clamp arm is coupled to the shaft assembly with a plurality of members configured to translate within the slots.

17. A method of performing a surgical procedure on tissue using an ultrasonic instrument, the ultrasonic instrument comprising a body configured to receive an ultrasonic transducer, the ultrasonic instrument further comprising a shaft assembly comprising an acoustic waveguide in acoustic communication with the ultrasonic transducer, the ultrasonic instrument further comprising an ultrasonic blade in acoustic communication with the acoustic waveguide, the ultrasonic instrument further comprising a retractable clamp arm comprising a clamp pad extending distally relative to a pivot point, the retractable clamp arm further comprising an actuator extending proximally relative to the pivot point, the method comprising the steps of:
(a) translating the actuator, the pivot point, and the clamp pad distally relative to the body, relative to the shaft assembly, and relative to the ultrasonic blade, from an inoperative position to an operative position, wherein the clamp pad is positioned proximal to the ultrasonic blade when the clamp pad is in the inoperative position, wherein the clamp pad is positioned lateral to the ultrasonic blade when the clamp pad is in the operative position;
(b) positioning tissue between the clamp pad and the ultrasonic blade;
(c) pivoting the actuator toward the body to thereby pivot the clamp pad toward the ultrasonic blade so as to capture the tissue between the clamp pad and the ultrasonic blade; and
(d) translating the actuator, the pivot point, and the clamp pad proximally relative to the body, relative to the shaft assembly, and relative to the ultrasonic blade, from the operative position to the inoperative position.

* * * * *